US009949874B2

(12) United States Patent
Contiliano et al.

(10) Patent No.: US 9,949,874 B2
(45) Date of Patent: Apr. 24, 2018

(54) THERAPEUTIC AGENT DELIVERY DEVICE WITH CONVERGENT LUMEN

(71) Applicant: Janssen Biotech, Inc., Horsham, PA (US)

(72) Inventors: Joseph H. Contiliano, Stewartsville, NJ (US); Thomas E. Meyer, Cincinnati, OH (US); Daniel J. Abbott, Maple Valley, WA (US); Michael F. Keane, Downingtown, PA (US); Allen C. Ho, Lower Gwynedd, PA (US); Mark C. Tsai, Chalfont, PA (US); Isaac J. Khan, Bridgewater, NJ (US)

(73) Assignee: Janssen Biotech, Inc., Horsham, PA (US)

( * ) Notice: Subject to any disclaimer, the term of this patent is extended or adjusted under 35 U.S.C. 154(b) by 172 days.

(21) Appl. No.: 14/726,786

(22) Filed: Jun. 1, 2015

(65) Prior Publication Data

US 2015/0351958 A1    Dec. 10, 2015

Related U.S. Application Data

(60) Provisional application No. 62/008,745, filed on Jun. 6, 2014.

(51) Int. Cl.
*A61F 9/00* (2006.01)
*A61M 25/06* (2006.01)

(52) U.S. Cl.
CPC .......... *A61F 9/0008* (2013.01); *A61F 9/0017* (2013.01); *A61M 25/065* (2013.01);
(Continued)

(58) Field of Classification Search
CPC .... A61F 9/0008; A61F 9/0017; A61F 9/0026; A61F 9/00736; A61M 25/0662; A61M 25/065; A61M 2025/0681
(Continued)

(56) References Cited

U.S. PATENT DOCUMENTS 4,585,435 A * 4/1986 Vaillancourt ....... A61M 5/1408
604/126
5,314,411 A * 5/1994 Bierman ............... A61M 25/02
604/174

(Continued)

FOREIGN PATENT DOCUMENTS

| EP | 2 500 002 A1 | 9/2012 |
| WO | WO 2010/132751 A1 | 11/2010 |
| WO | WO 2015/187611 A1 | 12/2015 |

OTHER PUBLICATIONS

International Search Report and Written Opinion dated Oct. 13, 2015 for Application No. PCT/US2015/033657, 13 pgs.
(Continued)

*Primary Examiner* — Emily Schmidt
*Assistant Examiner* — Amber Stiles
(74) *Attorney, Agent, or Firm* — Frost Brown Todd LLC

(57) ABSTRACT

An apparatus has a first fluid conduit, a second fluid conduit, a connector member, an first tubular member, a second tubular member, and an inner cannula. The connector member has first and second passageways in which the first and second fluid conduits are positioned, respectively. A portion of the second tubular member is positioned within the lumen of the first tubular member. A proximal portion of the inner cannula is fixedly secured within the lumen of the first tubular member. The inner cannula lumen is in fluid communication with the first and second fluid conduits via the lumen of the first tubular member and the lumen of the second tubular member. The inner cannula may be inserted into the subretinal space of a human eye to deliver a leading bleb of fluid and then deliver a therapeutic agent, without having to withdraw the inner cannula from the subretinal space between the acts of delivering the leading bleb delivering the therapeutic agent.

15 Claims, 52 Drawing Sheets

(52) U.S. Cl.
CPC ....... *A61M 25/0662* (2013.01); *A61F 9/0026* (2013.01); *A61M 2025/0681* (2013.01)

(58) Field of Classification Search
USPC .................................. 604/506, 518, 521, 82
See application file for complete search history.

(56) References Cited

U.S. PATENT DOCUMENTS

| | | |
|---|---|---|
| 5,419,777 A | 5/1995 | Hofling |
| 5,464,395 A | 11/1995 | Faxon et al. |
| 7,413,734 B2 | 8/2008 | Mistry et al. |
| 2005/0143363 A1 | 6/2005 | De Juan et al. |
| 2010/0217231 A1* | 8/2010 | Ilan .................. A61B 17/00491 604/506 |
| 2015/0223977 A1 | 8/2015 | Oberkircher et al. |

OTHER PUBLICATIONS

International Preliminary Report on Patentability dated Dec. 6, 2016 for Application No. PCT/US2015/033657, 8 pgs.
U.S. Appl. No. 62/008,745, filed Jun. 6, 2014.

* cited by examiner

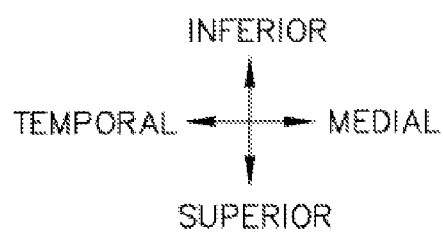
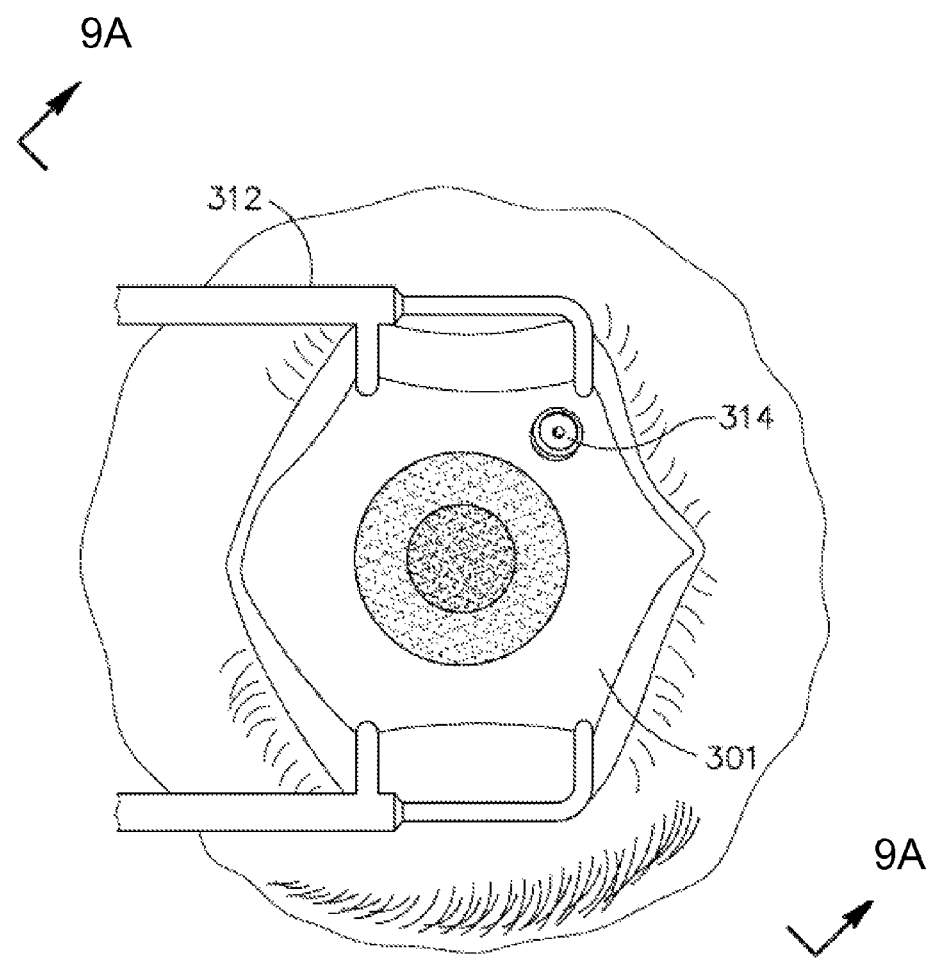
Fig 8A

US 9,949,874 B2

THERAPEUTIC AGENT DELIVERY DEVICE WITH CONVERGENT LUMEN

PRIORITY

This application claims priority to U.S. Provisional Patent Application No. 62/008,745, entitled "Convergent Lumen Delivery Device and Method of Using for Delivery of Bioactive Agents (Transvitreal)," filed Jun. 6, 2014, the disclosure of which is incorporated by reference herein.

JOINT RESEARCH STATEMENT

Subject matter disclosed in this application was developed and the claimed invention was made by, or on behalf of, one or more parties to a joint research agreement that was in effect on or before the effective filing date of the claimed invention. The claimed invention was made as a result of activities undertaken within the scope of the joint research agreement. The parties to the joint research agreement include Ethicon Endo-Surgery, Inc. and Janssen Research & Development, LLC.

BACKGROUND

The human eye comprises several layers. The white outer layer is the sclera, which surrounds the choroid layer. The retina is interior to the choroid layer. The sclera contains collagen and elastic fiber, providing protection to the choroid and retina. The choroid layer includes vasculature providing oxygen and nourishment to the retina. The retina comprises light sensitive tissue, including rods and cones. The macula is located at the center of the retina at the back of the eye, generally centered on an axis passing through the centers of the lens and cornea of the eye (i.e., the optic axis). The macula provides central vision, particularly through cone cells.

Macular degeneration is a medical condition that affects the macula, such that people suffering from macular degeneration may experience lost or degraded central vision while retaining some degree of peripheral vision. Macular degeneration may be caused by various factors such as age (also known as "AMD") and genetics. Macular degeneration may occur in a "dry" (nonexudative) form, where cellular debris known as drusen accumulates between the retina and the choroid, resulting in an area of geographic atrophy. Macular degeneration may also occur in a "wet" (exudative) form, where blood vessels grow up from the choroid behind the retina. Even though people having macular degeneration may retain some degree of peripheral vision, the loss of central vision may have a significant negative impact on the quality of life. Moreover, the quality of the remaining peripheral vision may be degraded and in some cases may disappear as well. It may therefore be desirable to provide treatment for macular degeneration in order to prevent or reverse the loss of vision caused by macular degeneration. In some cases it may be desirable to provide such treatment in a highly localized fashion, such as by delivering a therapeutic substance in the subretinal layer (under the neurosensory layer of the retina and above the retinal pigment epithelium) directly adjacent to the area of geographic atrophy, near the macula. However, since the macula is at the back of the eye and underneath the delicate layer of the retina, it may be difficult to access the macula in a practical fashion.

While a variety of surgical methods and instruments have been made and used to treat an eye, it is believed that no one prior to the inventors has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 8A depicts a top plan view of an eye of a patient, with surrounding structures of the eye immobilized and a chandelier installed;

Figure 1:
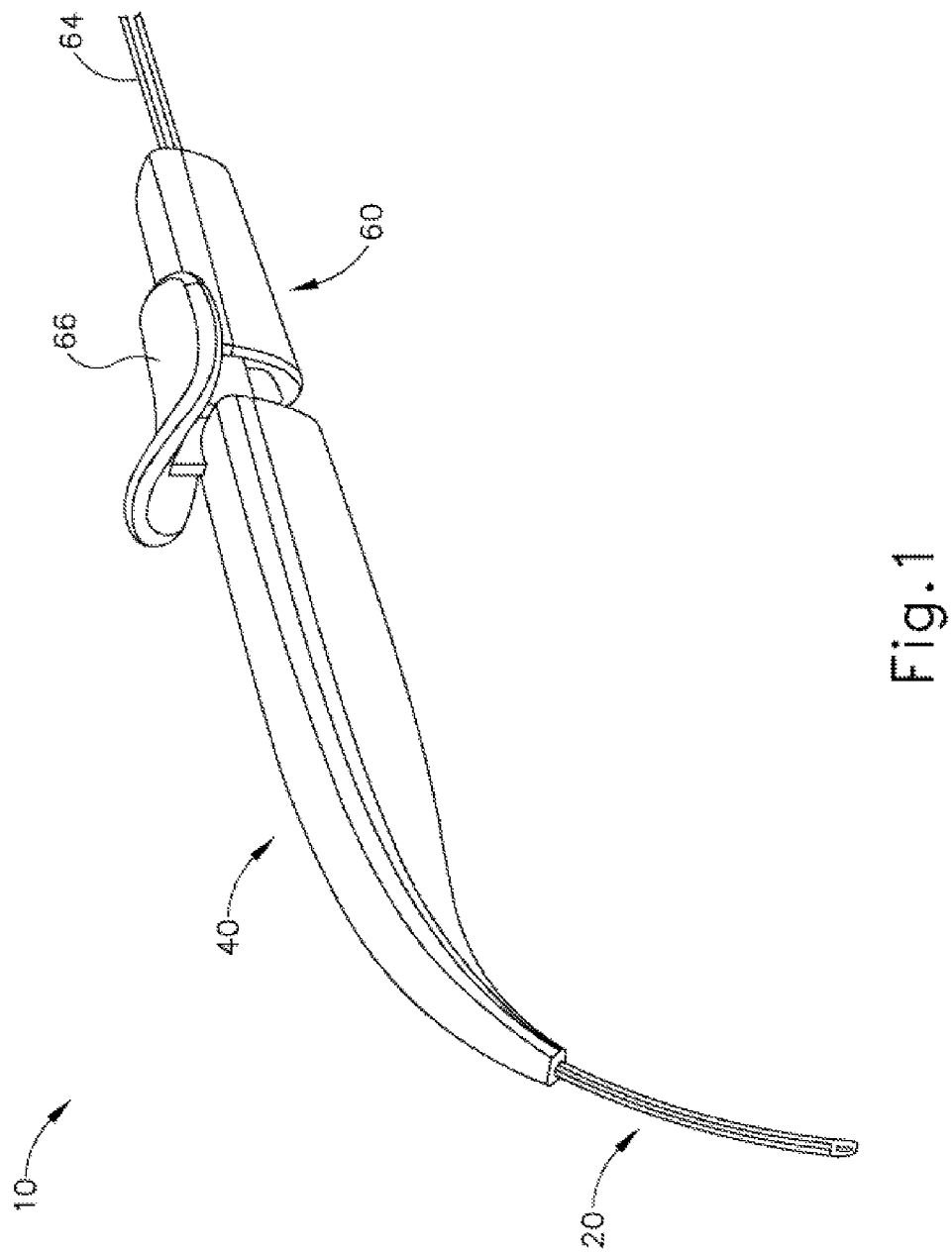
FIG. 1 depicts a perspective view of an exemplary instrument for subretinal administration of a therapeutic agent from a suprachoroidal approach.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

For clarity of disclosure, the terms "proximal" and "distal" are defined herein relative to a surgeon or other operator grasping a surgical instrument having a distal surgical end effector. The term "proximal" refers the position of an element closer to the surgeon or other operator and the term "distal" refers to the position of an element closer to the surgical end effector of the surgical instrument and further away from the surgeon or other operator.

I. Exemplary Therapeutic Agent Delivery Instrument with Slider Needle Actuation Feature FIGS. 1-4 show an exemplary instrument (10) that is configured for use in a procedure for the subretinal administration of a therapeutic agent to an eye of a patient from a suprachoroidal approach. Instrument (10) comprises a flexible cannula (20), a body (40), and a slidable actuation assembly (60). Cannula (20) extends distally from body (40) and has a generally rectangular cross section. Cannula (20) is generally configured to support a needle (30) that is slidable within cannula (20), as will be described in greater detail below.

In the present example, cannula (20) comprises a flexible material such as Polyether block amide (PEBA), which may be manufactured under the trade name PEBAX. Of course, any other suitable material or combination of materials may be used. Also in the present example, cannula (20) has a cross-sectional profile dimension of approximately 2.0 mm by 0.8 mm, with a length of approximately 80 mm. Alternatively, any other suitable dimensions may be used.

As will be described in greater detail below, cannula (20) is flexible enough to conform to specific structures and contours of the patient's eye, yet cannula (20) has sufficient column strength to permit advancement of cannula (20) between the sclera and choroid of patient's eye without buckling. Several factors may contribute to suitable flexibility of cannula (20). For instance, the durometer of the material used to construct cannula (20) at least partially characterizes the flexibility of cannula (20). By way of example only, the material that is used to form cannula (20) may have a shore hardness of approximately 27D, approximately 33D, approximately 42D, approximately 46D, or any other suitable shore hardness. It should be understood that the shore hardness may fall within the range of approximately 27D to approximately 46D; or more particularly within the range of approximately 33D to approximately 46D; or more particularly within the range of approximately 40D to approximately 45D. The particular cross-sectional shape of cannula (20) may also at least partially characterize the flexibility of cannula (20). Additionally, the stiffness of needle (30) disposed within cannula (20) may at least partially characterize the flexibility of cannula (20).

In the present example, the flexibility of cannula (20) may be quantified by calculating a bending stiffness for cannula (20). Bending stiffness is calculated by the product of the elastic modulus and the area moment of inertia. By way of example only, one exemplary material that may be used to form cannula (20) may have a shore hardness of D27, an elastic modulus (E) of $1.2 \times 10^7$ N/m$^2$, and an area moment of inertia ($I_x$) of $5.52 \times 10^{-14}$ m$^4$, providing a calculated bending stiffness about the x-axis at $0.7 \times 10^{-6}$ Nm$^2$. Another exemplary material that may be used to form cannula (20) may have a shore hardness of D33, an elastic modulus (E) of $2.1 \times 10^7$ N/m$^2$, and an area moment of inertia ($I_x$) of $5.52 \times 10^{-14}$ m$^4$, providing a calculated bending stiffness about the x-axis at $1.2 \times 10^{-6}$ Nm$^2$. Another exemplary material that may be used to form cannula (20) may have a shore hardness of D42, an elastic modulus (E) of $7.7 \times 10^7$ N/m$^2$, and an area moment of inertia ($I_x$) of $5.52 \times 10^{-14}$ m$^4$, providing a calculated bending stiffness about the x-axis at $4.3 \times 10^{-6}$ Nm$^2$. Another exemplary material that may be used to form cannula (20) may have a shore hardness of D46, an elastic modulus (E) of $17.0 \times 10^7$ N/m$^2$, and an area moment of inertia ($I_x$) of $5.52 \times 10^{-14}$ m$^4$, providing a calculated bending stiffness about the x-axis at $9.4 \times 10^{-6}$ Nm$^2$. Thus, by way of example only, the bending stiffness of cannula (20) may fall within the range of approximately $0.7 \times 10^{-6}$ Nm$^2$ to approximately $9.4 \times 10^{-6}$ Nm$^2$; or more particularly within the range of approximately $1.2 \times 10^{-6}$ Nm$^2$ to approximately $9.4 \times 10^{-6}$ Nm$^2$; or more particularly within the range of approximately $2.0 \times 10^{-6}$ Nm$^2$ to approximately $7.5 \times 10^{-6}$ Nm$^2$; or more particularly within the range of approximately $2.0 \times 10^{-6}$ Nm$^2$ to approximately $6.0 \times 10^{-6}$ Nm$^2$; or more particularly within the range of approximately $3.0 \times 10^{-6}$ Nm$^2$ to approximately $5.0 \times 10^{-6}$ Nm$^2$; or more particularly within the range of approximately $4.0 \times 10^{-6}$ Nm$^2$ to approximately $5.0 \times 10^{-6}$ Nm$^2$.

In the present example, the flexibility of cannula (20) may also be quantified by the following formula:

$$\delta = \frac{FL^3}{48EI} \quad (1)$$

In the above equation, bending stiffness (EI) is calculated experimentally by deflecting cannula (20) having a fixed span (L) a set distance to yield a predetermined amount of deflection ($\delta$). The amount of force (F) required for such a deflection may then be recorded. For instance, when using such a method cannula (20) may have a span of 0.06 m and may be deflected for a given distance. By way of example only, one exemplary material that may be used to form cannula (20) may require a force of 0.0188 N to achieve a deflection of 0.0155 m, providing a calculated bending stiffness about the x-axis of $5.5 \times 10^{-6}$ Nm$^2$. In another exemplary material that may be used to form cannula (20) may require a force of 0.0205 N to achieve a deflection of 0.0135 m, providing a calculated bending stiffness about the x-axis of $6.8 \times 10^{-6}$ Nm$^2$. In still another exemplary material that may be used to form cannula (20) may require a force of 0.0199 N to achieve a deflection of 0.0099 m, providing a calculated bending stiffness about the x-axis of $9.1 \times 10^{-6}$ Nm$^2$. In yet another exemplary material that may be used to form cannula (20) may require a force of 0.0241 N to achieve a deflection of 0.0061 m, providing a calculated bending stiffness about the x-axis of $1.8 \times 10^{-6}$ Nm$^2$. In yet another exemplary material that may be used to form cannula (20) may require a force of 0.0190 N to achieve a deflection 0.0081 m, providing a calculated bending stiffness about the x-axis of $1.0 \times 10^{-6}$ Nm$^2$. In yet another exemplary material that may be used to form cannula (20) may require a force of 0.0215 N to achieve a deflection of 0.0114 m, providing a calculated bending stiffness about the x-axis of $8.4 \times 10^{-6}$ Nm$^2$. In yet another exemplary material that may be used to form cannula (20) may require a force of 0.0193 N to achieve a deflection of 0.0170 m, providing a calculated bending stiffness about the x-axis of $5.1 \times 10^{-6}$ Nm$^2$. In yet another exemplary material that may be used to form cannula (20) may require a force of 0.0224 N to achieve a deflection of 0.0152 m, providing a calculated bending stiffness about the x-axis of $6.6 \times 10^{-6}$ Nm$^2$. In yet another exemplary material that may be used to form cannula (20) may require a force of 0.0183 N to achieve a deflection of 0.0119 m, providing a calculated bending stiffness about the x-axis of $6.9 \times 10^{-6}$ Nm$^2$. In yet another exemplary material that may be used to form cannula (20) may require a force of 0.0233 N to achieve a deflection of 0.0147 m, providing a calculated bending stiffness about the x-axis of $7.1 \times 10^{-6}$ Nm$^2$. In yet another exemplary material that may be used to form cannula (20) may require a force of 0.0192 N to achieve a deflection of 0.0122, providing a calculated bending stiffness about the x-axis of $7.1 \times 10^{-6}$ Nm$^2$. In yet another exemplary material that may be used to form cannula (20) may require a force of 0.0201 N to achieve a deflection of 0.0201, providing a calculated bending stiffness about the x-axis of $4.5 \times 10^{-6}$ Nm$^2$. Thus, by way of example only, the bending stiffness of cannula (20) may fall within the range of approximately $1.0 \times 10^{-6}$ Nm² to approximately $9.1 \times 10^{-6}$ Nm². It should be understood that in other examples, the bending stiffness of cannula may fall within the range of approximately $0.7 \times 10^{-6}$ Nm² to approximately $11.1 \times 10^{-6}$ Nm²; or more particularly within the range of approximately $2.0 \times 10^{-6}$ Nm² to approximately $6.0 \times 10^{-6}$ Nm².

Needle (30) may have a bending stiffness that differs from the bending stiffness of cannula (20). By way of example only, needle (30) may be formed of a nitinol material that has an elastic modulus (E) of $7.9 \times 10^{10}$ N/m², and an area moment of inertia $(I_x)$ of $2.12 \times 10^{-17}$ m⁴, providing a calculated bending stiffness about the x-axis at $1.7 \times 10^{-6}$ Nm². By way of further example only, the bending stiffness of needle (30) may fall within the range of approximately $0.5 \times 10^{-6}$ Nm² to approximately $2.5 \times 10^{-6}$ Nm²; or more particularly within the range of approximately $0.75 \times 10^{-6}$ Nm² to approximately $2.0 \times 10^{-6}$ Nm²; or more particularly within the range of approximately $1.25 \times 10^{-6}$ Nm² to approximately $1.75 \times 10^{-6}$ Nm².

Figure 5:
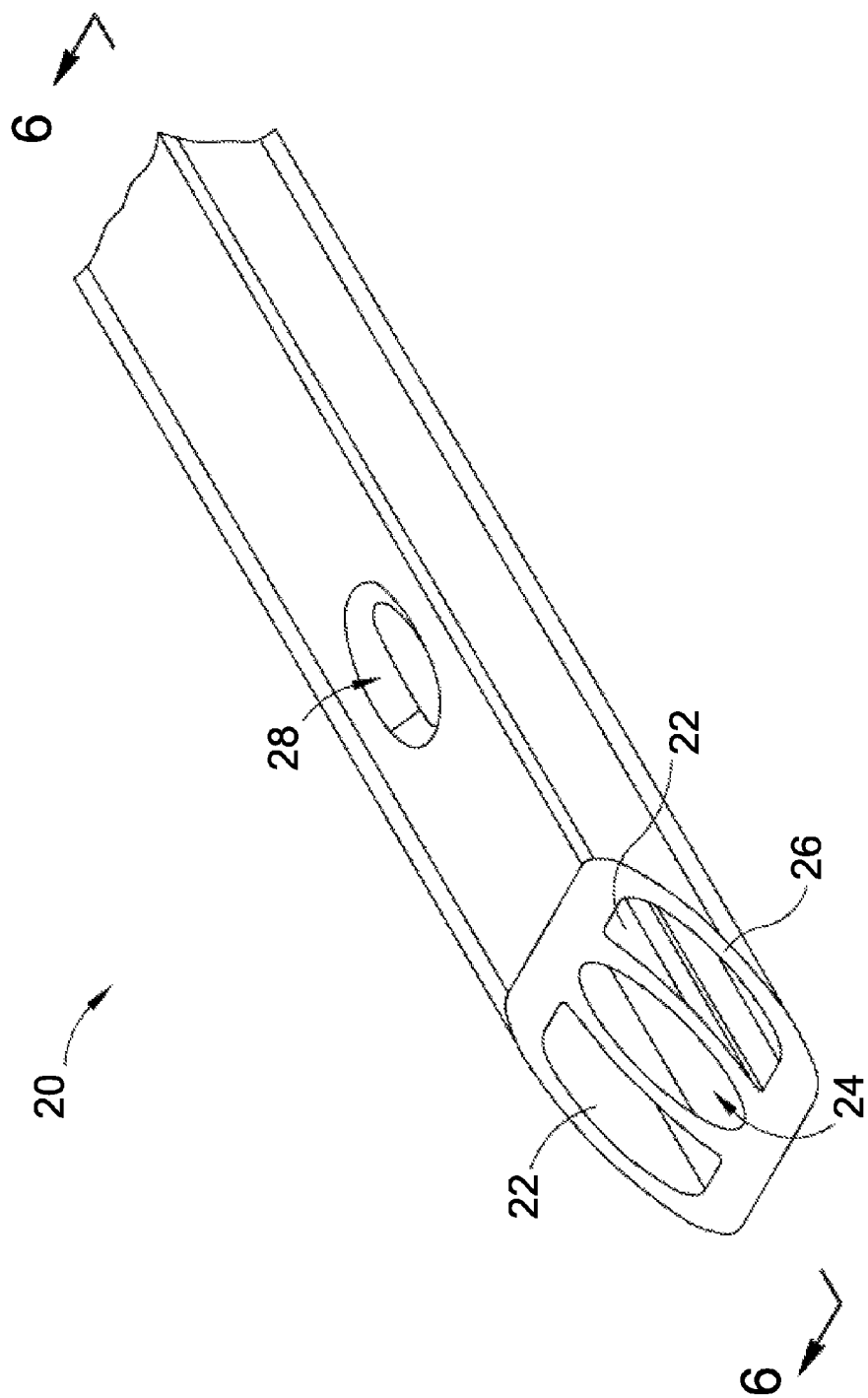
FIG. 5 depicts a perspective view of the distal end of an exemplary cannula that may be incorporated into the instrument of FIG. 1.
Figure 6:
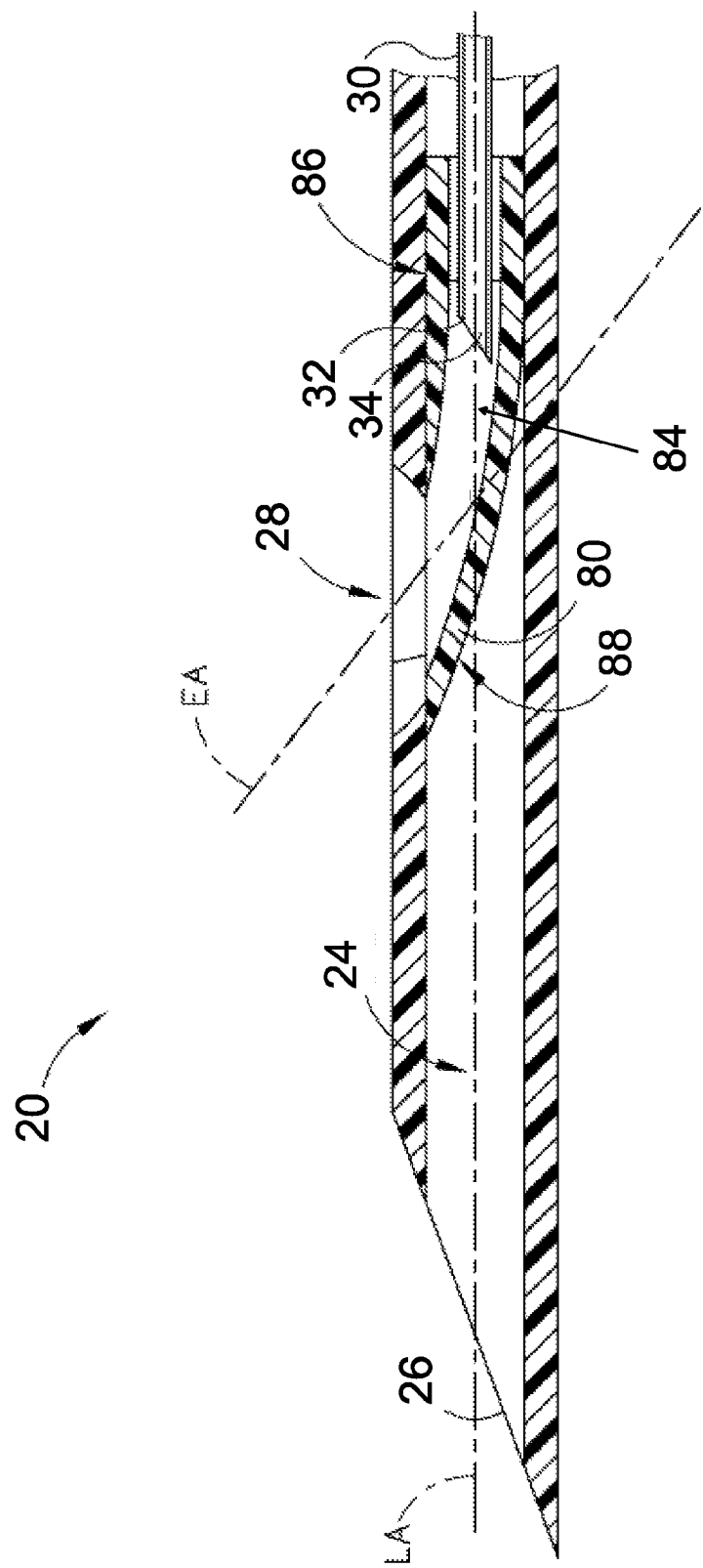
FIG. 6 depicts a cross-sectional view of the cannula of FIG. 5, with the cross-section taken along line 6-6 of FIG. 5.

As can be seen in FIGS. 5 and 6, cannula (20) comprises two side lumens (22) and a single central lumen (24) extending longitudinally through cannula (20) and terminating at an atraumatic, beveled distal end (26). A beveled lateral opening (28) is located proximal to beveled distal end (26). Side lumens (22) contribute to the flexibility of cannula (20). Although lumens (22, 24) are shown as being open at beveled distal end (26), it should be understood that in some examples, side lumens (22, 24) may be optionally closed at beveled distal end (26). As will be described in greater detail below, central lumen (24) is configured to receive needle (30) and a needle guide (80). In some versions, an optical fiber (not shown) is also disposed in central lumen (24) alongside needle (30). Such an optical fiber may be used to provide illumination and/or optical feedback.

Beveled distal end (26) is generally beveled to provide separation between the sclera and choroid layers to enable cannula (20) to be advanced between such layers while not inflicting trauma to the sclera or choroid layers. In the present example, beveled distal end (26) is beveled at an angle of approximately 15° relative to the longitudinal axis of cannula (20) in the present example. In other examples, beveled distal end (26) may have a bevel angle within the range of approximately 5° to approximately 50°; or more particularly within the range of approximately 5° to approximately 40°; or more particularly within the range of approximately 10° to approximately 30°; or more particularly within the range of approximately 10° to approximately 20°.

A needle guide (80) is disposed within lumen (24) such that the distal end of needle guide (80) abuts beveled lateral opening (28). Needle guide (80) is generally configured to direct needle (30) upwardly along an exit axis (EA) that is obliquely oriented relative to the longitudinal axis (LA) of cannula (20) through beveled opening (28) of cannula (20). Needle guide (80) may be formed of plastic, stainless steel, and/or any other suitable biocompatible material(s). The shape of needle guide (80) is configured for insertion into central lumen (24). In the present example, needle guide (80) is secured within central lumen (24) by a press or interference fit, although in other examples, adhesives and/or mechanical locking mechanisms may be used to secure needle guide (80).

As can best be seen in FIG. 6, needle guide (80) defines an internal lumen (84) that is configured to slidably receive needle (30). In particular, internal lumen (84) includes a generally straight proximal portion (86) and a curved distal portion (88). Straight proximal portion (86) corresponds to the longitudinal axis (LA) of cannula (20), while curved distal portion (88) curves upwardly away from the longitudinal axis of cannula (20). Curved distal portion (88) of the present example is curved to direct needle (30) along an exit axis (EA) that extends distally from cannula (20) at an angle of approximately 7° to approximately 9° relative to the longitudinal axis (LA) of cannula (20). It should be understood that such an angle may be desirable to deflect needle (30) in a direction to ensure penetration of needle into the choroid (306) and to minimize the possibility of needle (30) continuing beneath the choroid (306) through the suprachoroidal space (as opposed to penetrating through the choroid (306)) and the possibility of retinal perforation. By way of further example only, curved distal portion (88) may urge needle (30) to exit cannula (20) along an exit axis (EA) that is oriented at an angle within the range of approximately 5° to approximately 30° relative to the longitudinal axis (LA) of cannula (20); or more particularly within the range of approximately 5° to approximately 20° relative to the longitudinal axis (LA) of cannula (20); or more particularly within the range of approximately 5° to approximately 10° relative to the longitudinal axis (LA) of cannula (20).

Needle (30) is in the form of an inner cannula that has a sharp distal end (32) and defines an internal lumen (34). Distal end (32) of the present example has a lancet configuration. In some other versions, distal end (32) has a tri-bevel configuration or any other configuration as described in U.S. patent application Ser. No. 14/619,256, entitled "Method and Apparatus for Suprachoroidal Administration of Therapeutic Agent," filed Feb. 11, 2015, published as U.S. Pub. No. 2015/0223977 on Aug. 13, 2015, the disclosure of which is incorporated by reference herein. Still other suitable forms that distal end (32) may take will be apparent to those of ordinary skill in the art in view of the teachings herein. Needle (30) of the present example comprises a nitinol hypodermic needle that is sized to deliver the therapeutic agent while being small enough to create self sealing wounds as needle (30) penetrates tissue structures of the patient's eye, as will be described in greater detail below. By way of example only, needle (30) may be 35 gauge with a 100 µm inner diameter, although other suitable sizes may be used. For instance, the outer diameter of needle (30) may fall within the range of 27 gauge to 45 gauge; or more particularly within the range of 30 gauge to 42 gauge; or more particularly within the range of 32 gauge to 39 gauge. As another merely illustrative example, the inner diameter of needle (30) may fall within the range of approximately 50 µm to approximately 200 µm; or more particularly within the range of approximately 50 µm to approximately 150 µm; or more particularly within the range of approximately 75 µm to approximately 125 µm.

Referring back to FIGS. 1-2, body (40) is generally shaped as an elongate rectangle with a curved distal end. The particular shape of body (40) that is shown is configured to be grasped by an operator. Alternatively, body (40) may be mounted on a support device or robotic arm for ease of positioning instrument (10), as described in U.S. patent application Ser. No. 14/619,256, entitled "Method and Apparatus for Suprachoroidal Administration of Therapeutic Agent," filed Feb. 11, 2015, published as U.S. Pub. No. 2015/0223997 on Aug. 13, 2015, the disclosure of which is incorporated by reference herein.

Actuation assembly (60) includes an actuation member (62) and a locking member (66). Locking member (66) is removably attachable to body engagement portion (50), between body (40) and actuation member (62). As will be described in greater detail below, locking member (66) fills a space between body (40) and actuation member (62) to prevent actuation member (62) from being advanced distally relative to body (40). However, locking member (66) can be removed to selectively permit actuation member (62) to be advanced distally relative to body (40).

Figure 2:
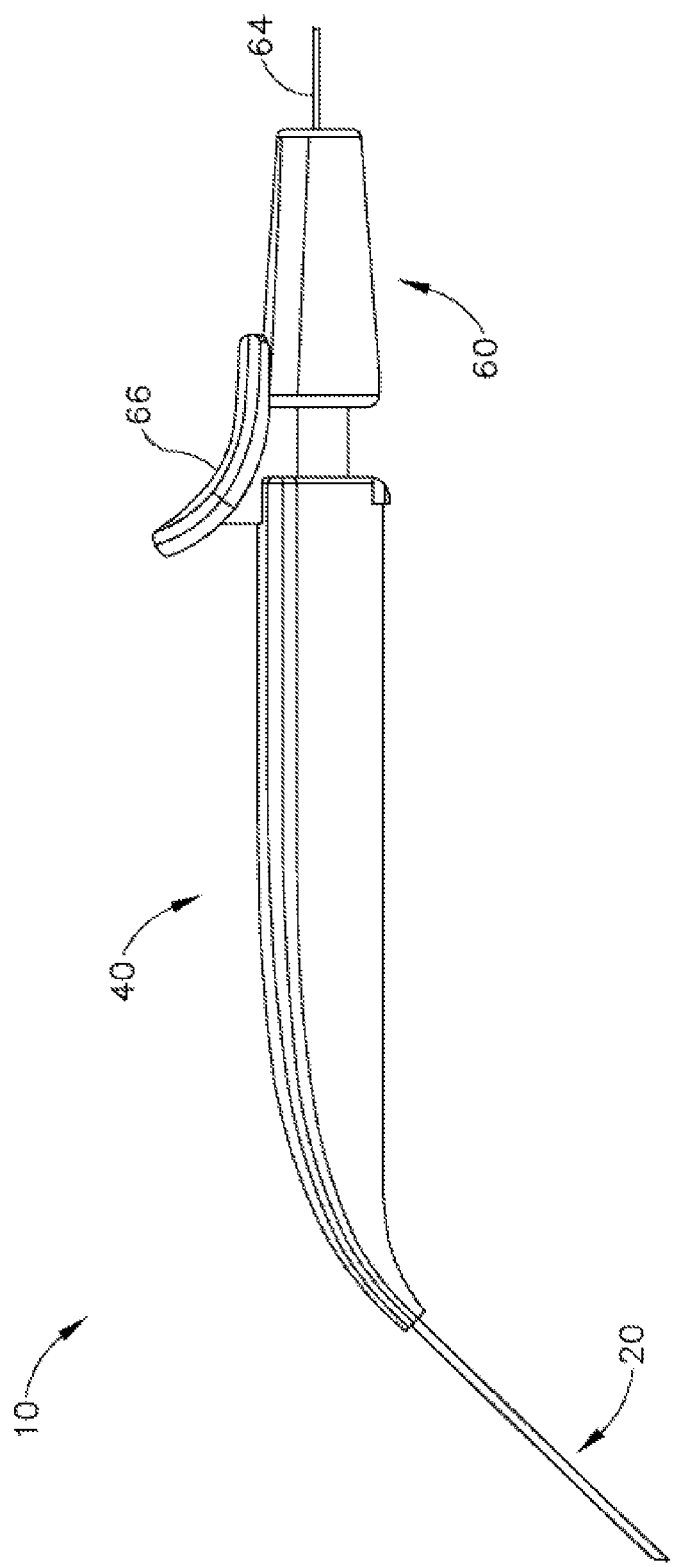
FIG. 2 depicts a side elevational view of the instrument of FIG. 1.
Figure 3:
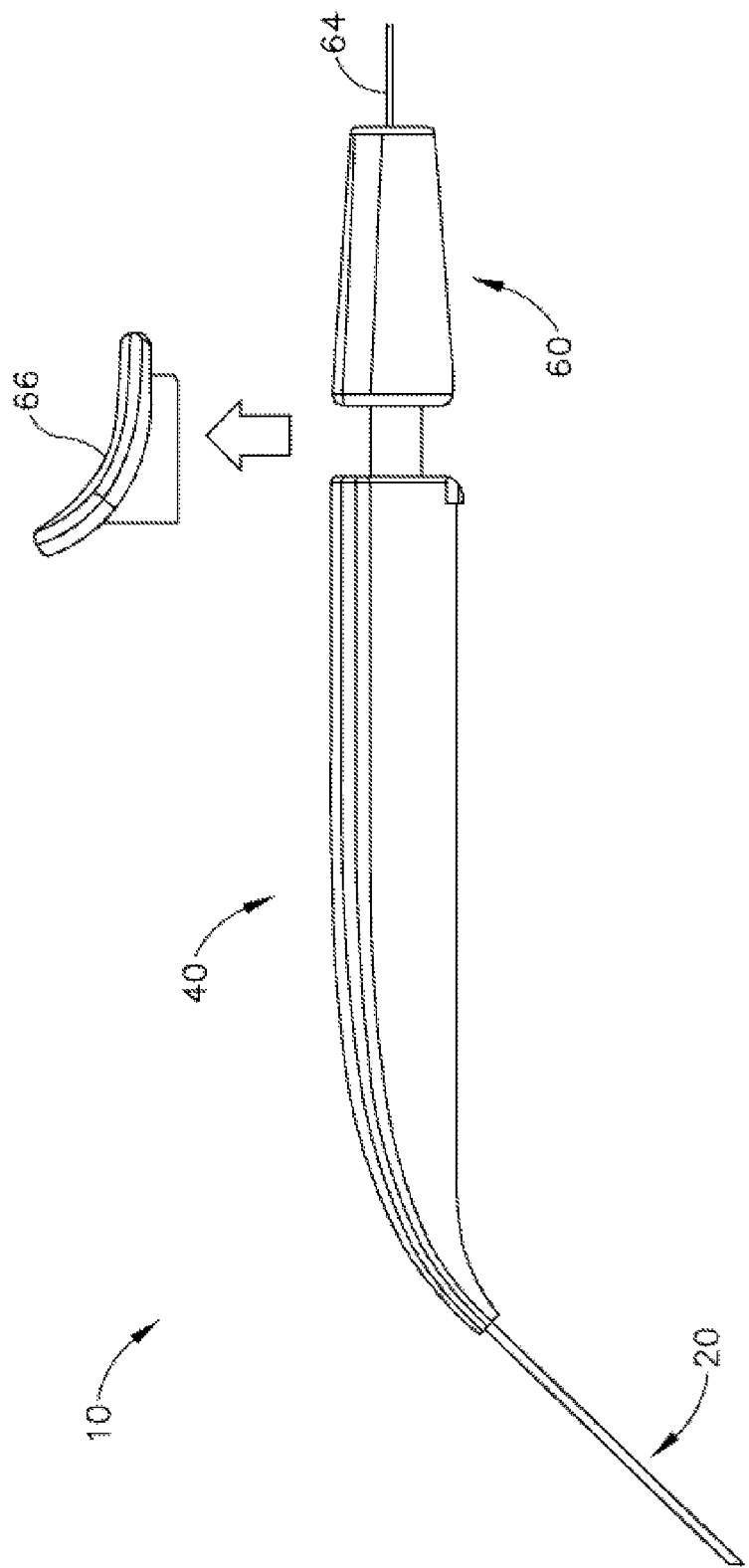
FIG. 3 depicts another side elevational view of the instrument of FIG. 1, with a locking member removed.
Figure 4:
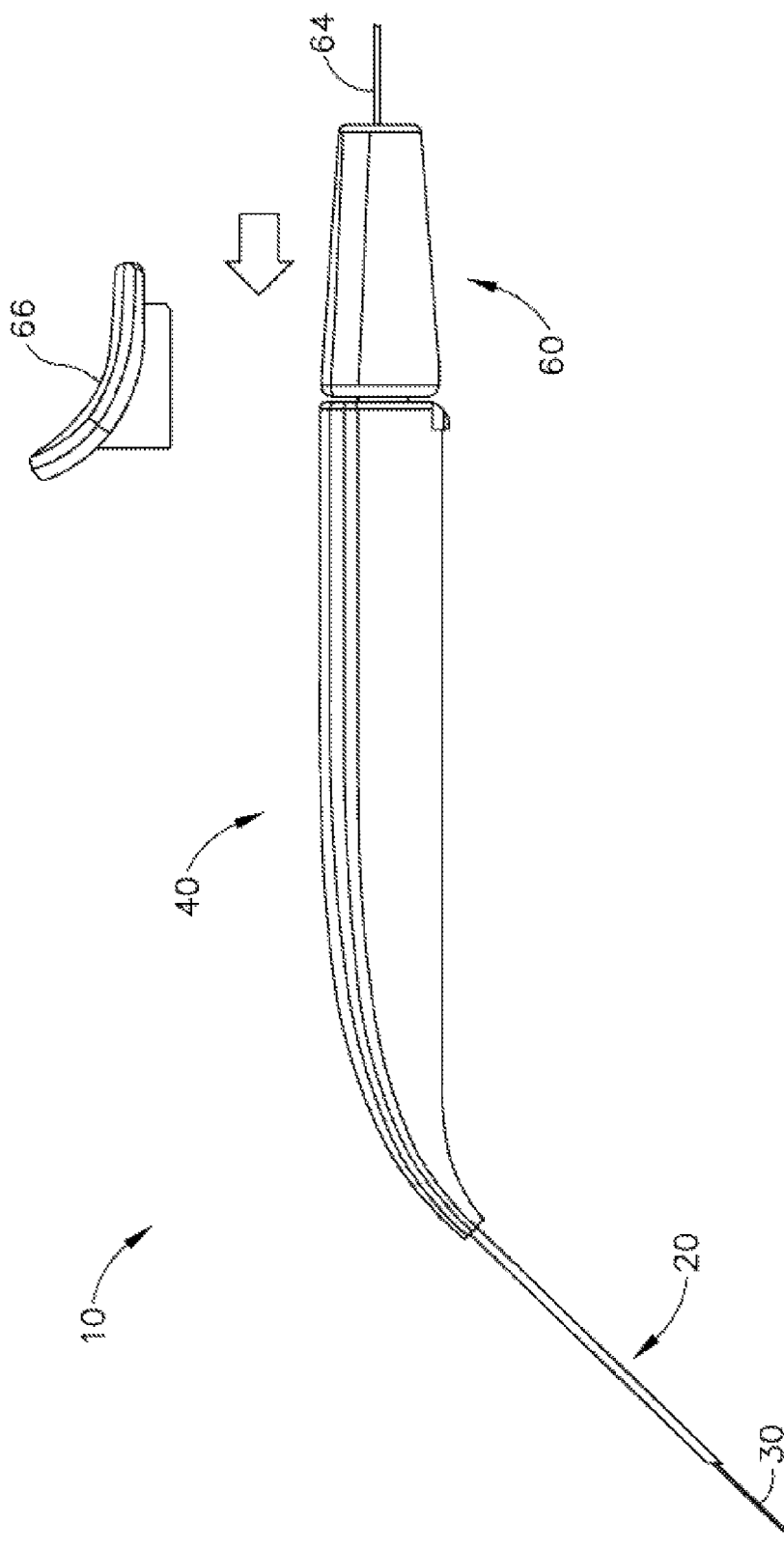
FIG. 4 depicts another side elevational view of the instrument of FIG. 1, with an actuation member advanced distally to extend the needle distally from the cannula.

FIGS. 2-4 show an exemplary actuation of instrument (10). In particular, as can be seen in FIG. 2, needle (30) is initially retracted into cannula (20) and locking member (66) is positioned between body (40) and actuation member (62), thereby preventing advancement of actuation member (62). With instrument (10) in this configuration, cannula (20) may be positioned within an eye of a patient as will be described in greater detail below.

Once cannula (20) is positioned within an eye of a patient, an operator may desire to advance needle (30) relative to cannula (20). To advance needle (30), an operator may first remove locking member (66) by pulling locking member (66) away from instrument (10), as can be seen in FIG. 3. Once locking member (66) is removed, actuation member (62) may be moved or translated relative to body (40) to advance needle (30) relative to cannula (20) as described in U.S. patent application Ser. No. 14/619,256, entitled "Method and Apparatus for Suprachoroidal Administration of Therapeutic Agent," filed Feb. 11, 2015, published as U.S. Pub. No. 2015/0223977 on Aug. 13, 2015, the disclosure of which is incorporated by reference herein. Actuation member (62) of the present example is only configured to translate needle (30) and not rotate needle (30). In other examples, it may be desirable to rotate needle (30). Accordingly, alternative examples may include features in actuation member (62) to rotate and translate needle (30).

In the present example, advancement of actuation member (62) into contact with body (40) as shown in FIG. 4 corresponds to advancement of needle (30) to a position relative to cannula (20) to a predetermined amount of penetration within an eye of a patient. In other words, instrument (10) is configured such that an operator only has to advance actuation member (62) into contact with body (40) to properly position needle (30) within an eye of a patient. In some examples, the predetermined amount of advancement of needle (30) relative to cannula (20) is between approximately 0.25 mm to approximately 10 mm; or more particularly within the range of approximately 0.1 mm to approximately 10 mm; or more particularly within the range of approximately 2 mm to approximately 6 mm; or more particularly to approximately 4 mm. In other examples, contact between actuation member (62) and body (40) may have no particular significance besides the maximum advancement of needle (30) relative to cannula (20). Instead, instrument (10) may be equipped with certain tactile feedback features to indicate to an operator when needle (30) has been advanced to certain predetermined distances relative to cannula (20). Accordingly, an operator may determine the desired depth of penetration of needle (30) into a patient's eye based on direct visualization of indicia on instrument and/or based on tactile feedback from instrument (10). Of course, such tactile feedback features may be combined with the present example, as will be apparent to those of ordinary skill in the art in view of the teachings herein.

II. Exemplary Suture Measurement Template

Figure 7:
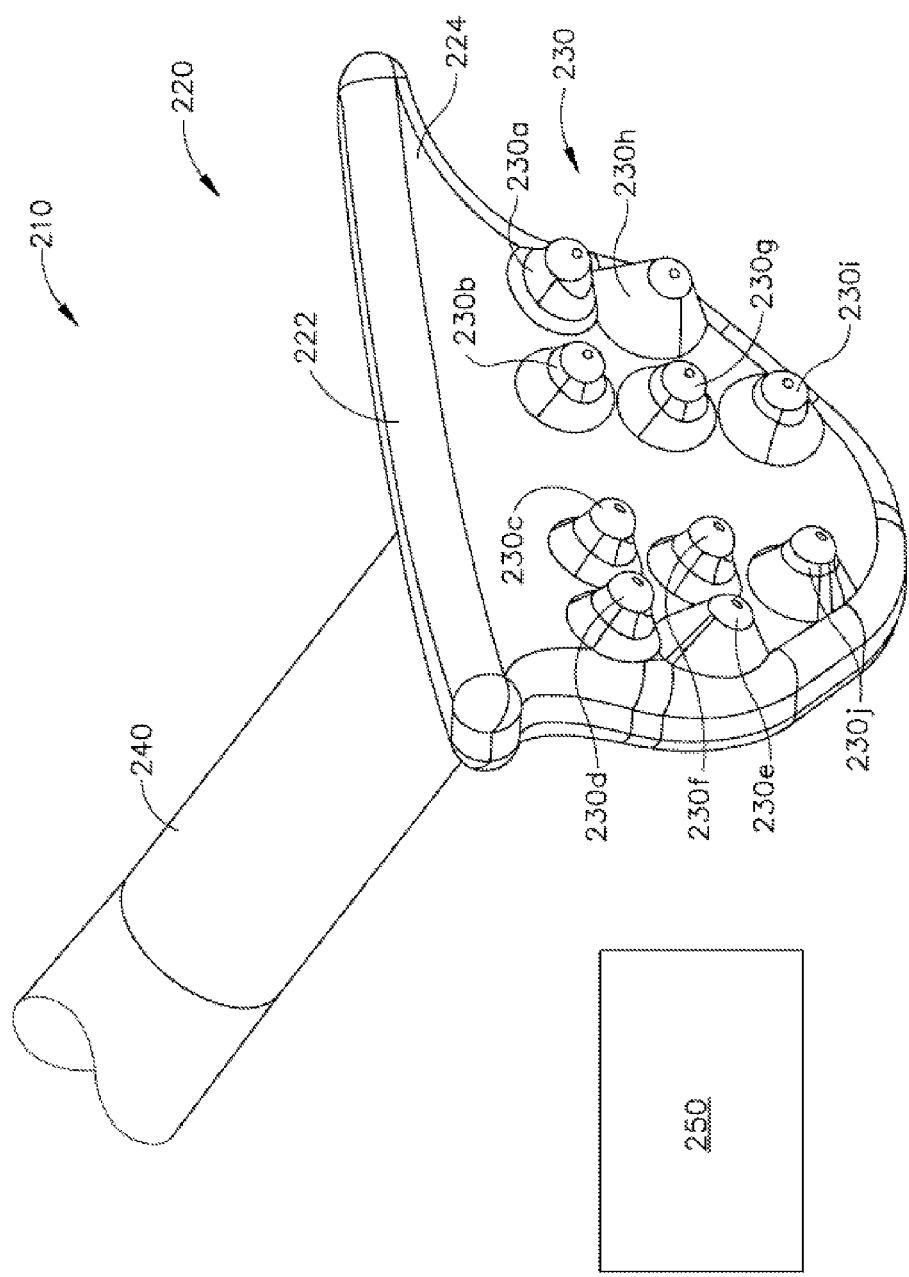
FIG. 7 depicts a perspective view of an exemplary suture measurement template for use in an exemplary method for the subretinal administration of a therapeutic agent from a suprachoroidal approach.

FIG. 7 shows an exemplary suture measurement template (210) that may be used in a procedure providing subretinal administration of a therapeutic agent from a suprachoroidal approach, as will be described in greater detail below. Generally, template (210) is configured to be pressed against an eye of a patient to stamp a particular pattern of pigment onto the patient's eye. It should be understood that reference herein to pressing template (210) against an eye of a patent may include, but is not necessarily limited to, pressing template (210) directly against the sclera (304) surface (e.g., after the conjunctiva has been taken down or otherwise displaced). Template (210) comprises a rigid body (220) and a rigid shaft (240). As will be described in greater detail below, body (220) is generally contoured to correspond to the curvature of a patient's eye such that body (220) may be pressed or placed onto at least a portion of the patient's eye. Body (220) comprises an upper guide portion (222) and a plurality of protrusions (230) extending distally from an eye face (224) of body (220).

Upper guide portion (222) is generally semi-circular in shape and is disposed at the top of body (220). The semi-circular shape of upper guide portion (222) has a radius that corresponds to the curvature of the limbus of a patient's eye. In other words, upper guide portion (222) curves proximally along a first radius corresponding to a radius of curvature of a patient's eyeball; and downwardly (toward the longitudinal axis of shaft (240)) along a second radius corresponding to a radius of curvature of the limbus of the patient's eye. As will be described in greater detail below, upper guide portion (222) may be used to properly locate template (210) relative to the limbus of the patient's eye. Accordingly, any pigmentation that may be deposited onto a patient's eye by template may be positioned relative to the limbus of the patient's eye.

Protrusions (230) are spaced a predetermined distance from upper guide portion (222). In particular, protrusions (230) form a pattern that may correspond to relevant marks for use during the method described below. Protrusions (230) of the present example comprise four suture loop protrusions (230a-230h) and two sclerotomy protrusions (230i, 230j). Suture loop protrusions (230a-320h) and sclerotomy protrusions (230i, 230j) extend outwardly from body (220) an equal distance such that protrusions (230) collectively maintain the curvature defined by body (220). In other words, the tips of protrusions (230a-230j) all lie along a curved plane that is defined by a radius of curvature complementing the radius of curvature of the patient's eyeball. The tips of protrusions (230a-230j) are rounded and atraumatic such that protrusions (230a-230j) may be pressed against the eye without damaging the sclera or other portions of the patient's eye.

Shaft (240) extends proximally from body (220). Shaft (240) is configured to permit an operator to grasp template (210) and manipulate body (220). In the present example, shaft (240) is integral with body (220). In other examples, shaft (240) may be selectively attachable to body by a mechanical fastening means such as a threaded coupling or a mechanical snap fit, etc. In some versions, an operator may be presented with a kit comprising a shaft (240) and a plurality of bodies (220). The bodies (220) may have different curvatures to correspond with different eyeballs having different radii of curvature. The operator may thus select an appropriate body (220) from the kit based on the anatomy of the particular patient before the operator; and the operator may then secure the selected body (220) to the shaft (240). Although not shown, it should be understood that the proximal end of shaft (240) may additionally include a t-grip, knob, or other gripping feature to permit an operator to more readily grip shaft (240).

In an exemplary use, suture loop protrusions (232) and sclerotomy protrusions (234) each correspond to a particular portion of the method described below. In particular, prior to, or during the method described below, an operator may coat protrusions (230) with a biocompatible pigment or ink by pressing protrusions (230) onto a pigment or ink pad (250), by brushing the pigment or ink onto protrusions (230), or by otherwise applying the pigment or ink to protrusions (230). In some versions, protrusions (230) may be pre-inked before template (210) is packaged. Once protrusions (230) have received the pigment or ink, an operator may mark an eye of a patent by pressing protrusions (230) of template (210) onto the eye of the patient, as will be described in greater detail below. Once template (210) is removed from an eye of a patient, the pigment from protrusions may remain adhered to the eye to mark particular points of interest, as will be described in greater detail below.

III. Exemplary Method for Subretinal Delivery of Therapeutic Agent from a Suprachoroidal Approach FIGS. 8A-10C show an exemplary procedure for subretinal administration of a therapeutic agent from a suprachoroidal approach using instrument (10) described above. It should be understood however, that instrument (2010) of FIGS. 11-13 may be readily used in addition to or in lieu of instrument (10) in the procedure described below. By way of example only, the method described herein may be employed to treat macular degeneration and/or other ocular conditions. Although the procedure described herein is discussed in the context of the treatment of age-related macular degeneration, it should be understood that no such limitation is intended or implied. For instance, in some merely exemplary alternative procedures, the same techniques described herein may be used to treat retinitis pigmentosa, diabetic retinopathy, and/or other ocular conditions. Additionally, it should be understood that the procedure described herein may be used to treat either dry or wet age-related macular degeneration.

Figure 10A:
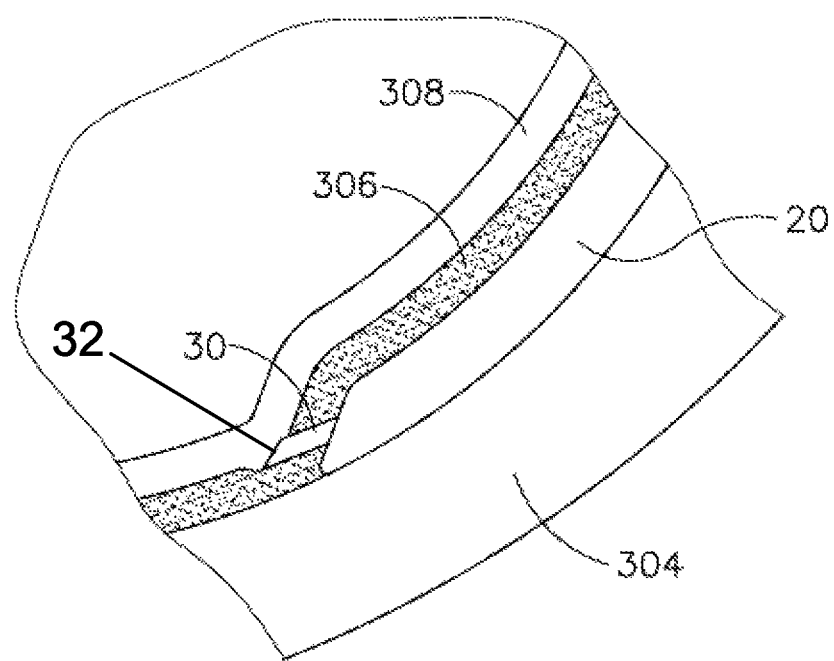
FIG. 10A depicts a detailed cross-sectional view of the eye of FIG. 8A depicted in the state shown in FIG. 9E.

As can be seen in FIG. 8A, the procedure begins by an operator immobilizing tissue surrounding a patient's eye (301) (e.g., the eyelids) using a speculum (312), and/or any other instrument suitable for immobilization. While is immobilization described herein with reference to tissue surrounding eye (301), it should be understood that eye (301) itself may remain free to move. Once the tissue surrounding eye (301) has been immobilized, an eye chandelier port (314) is inserted into eye (301) to provide intraocular illumination when the interior of eye (301) is viewed through the pupil. In the present example, eye chandelier port (314) is positioned in the inferior medial quadrant such that a superior temporal quadrant sclerotomy may be preformed. As can be seen in FIG. 10A, eye chandelier port (314) is positioned to direct light onto the interior of eye (314) to illuminate at least a portion of the retina (e.g., including at least a portion of the macula). As will be understood, such illumination corresponds to an area of eye (301) that is being targeted for delivery of therapeutic agent. In the present example, only chandelier port (314) is inserted at this stage, without yet inserting an optical fiber (315) into port (314). In some other versions, an optical fiber (315) may be inserted into chandelier port (314) at this stage. In either case, a microscope may optionally be utilized to visually inspect the eye to confirm proper positioning of eye chandelier port (314) relative to the target site. In some examples, the target region may be identified by a relative lack of retinal pigmentation. Although FIG. 8A shows a particular positioning of eye chandelier port (314), it should be understood that eye chandelier port (314) may have any other positioning as will be apparent to those of ordinary skill in the art in view of the teachings herein.

Figure 8B:
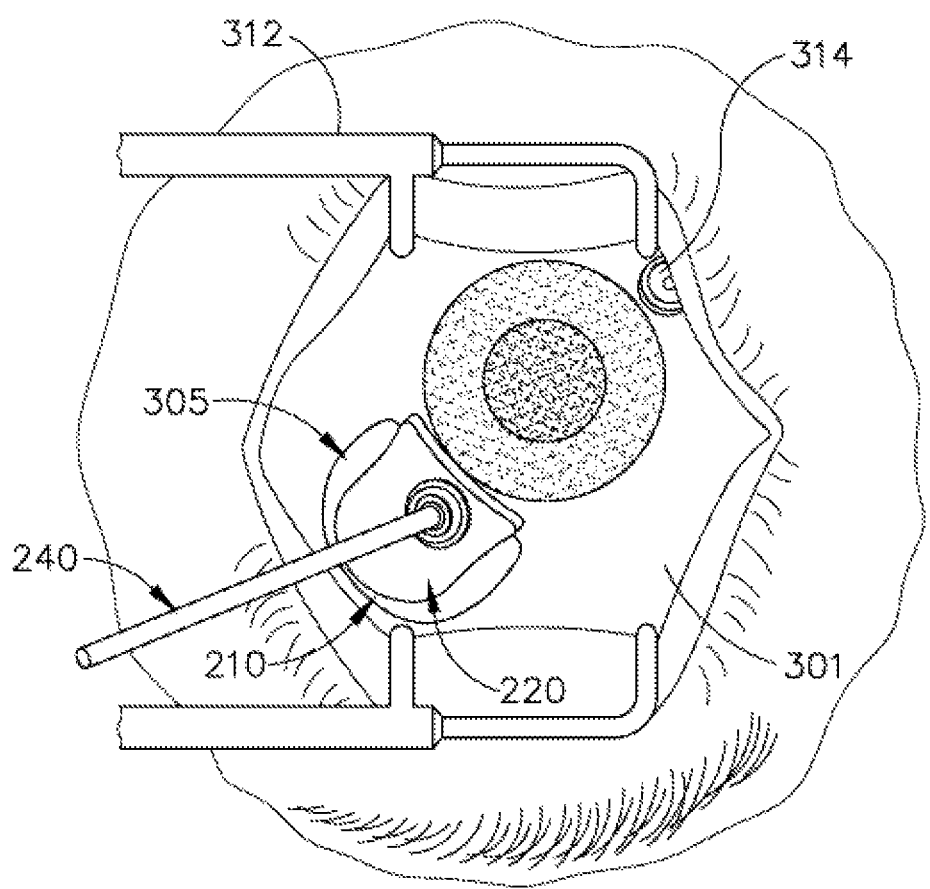
FIG. 8B depicts a top plan view of the eye of FIG. 8A, with the template of FIG. 7 disposed on the eye.
Figure 8C:
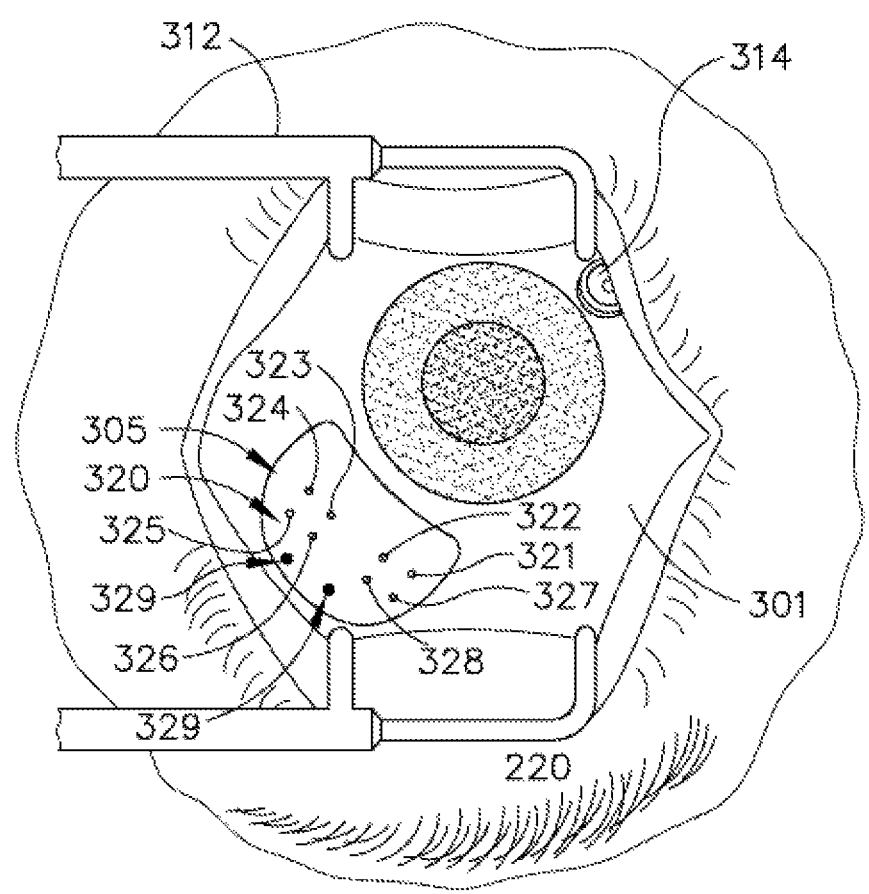
FIG. 8C depicts a top plan view of the eye of FIG. 8A, with a plurality of markers disposed on the eye.

Once eye chandelier port (314) has been positioned, the sclera (304) may be accessed by dissecting the conjunctiva by incising a flap in the conjunctiva and pulling the flap posteriorly. After such a dissection is completed, the exposed surface (305) of the sclera (304) may optionally be blanched using a cautery tool to minimize bleeding. Once conjunctiva dissection is complete, the exposed surface (305) of the sclera (304) may optionally be dried using a WECK-CEL or other suitable absorbent device. Template (210), described above, may then be used to mark eye (301). As can be seen in FIG. 8B, template (210) is positioned to align with the limbus of eye (301). An operator may apply a light force to template (210) to apply pigment to eye (301). Template (210) is then removed, leaving pigment adhered to the exposed surface (305) of the sclera (304) to provide a visual guide (320) for an operator, as can be seen in FIG. 8C. An operator may then use visual guide (320) to attach a suture loop assembly (330) and to perform a sclerotomy. Visual guide (320) comprises a set of suture loop markers (321, 322, 323, 324, 325, 326, 327) and a pair of sclerotomy markers (329).

Figure 8D:
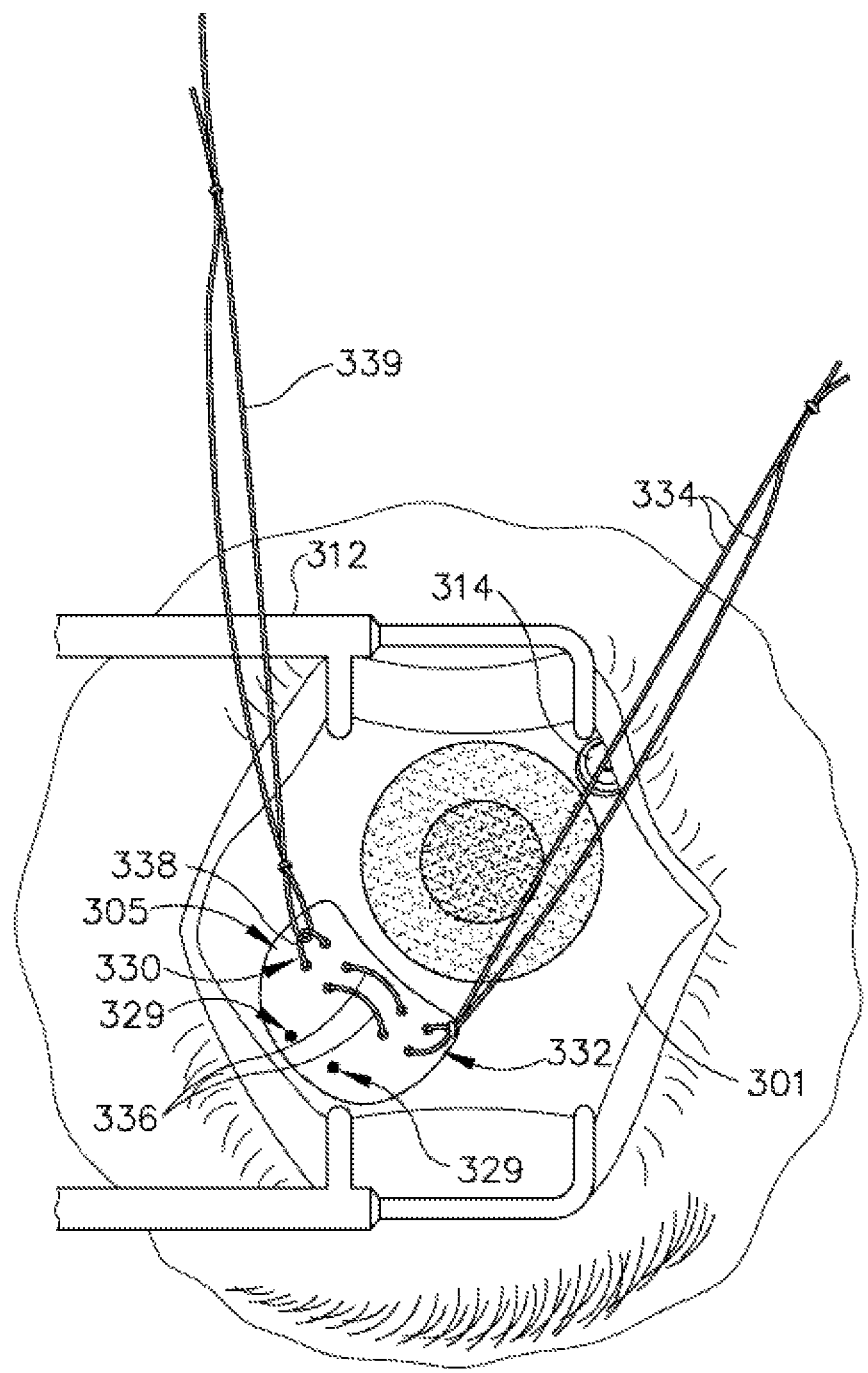
FIG. 8D depicts a top plan view of the eye of FIG. 8A, with a suture loop attached to the eye.
Figure 8E:
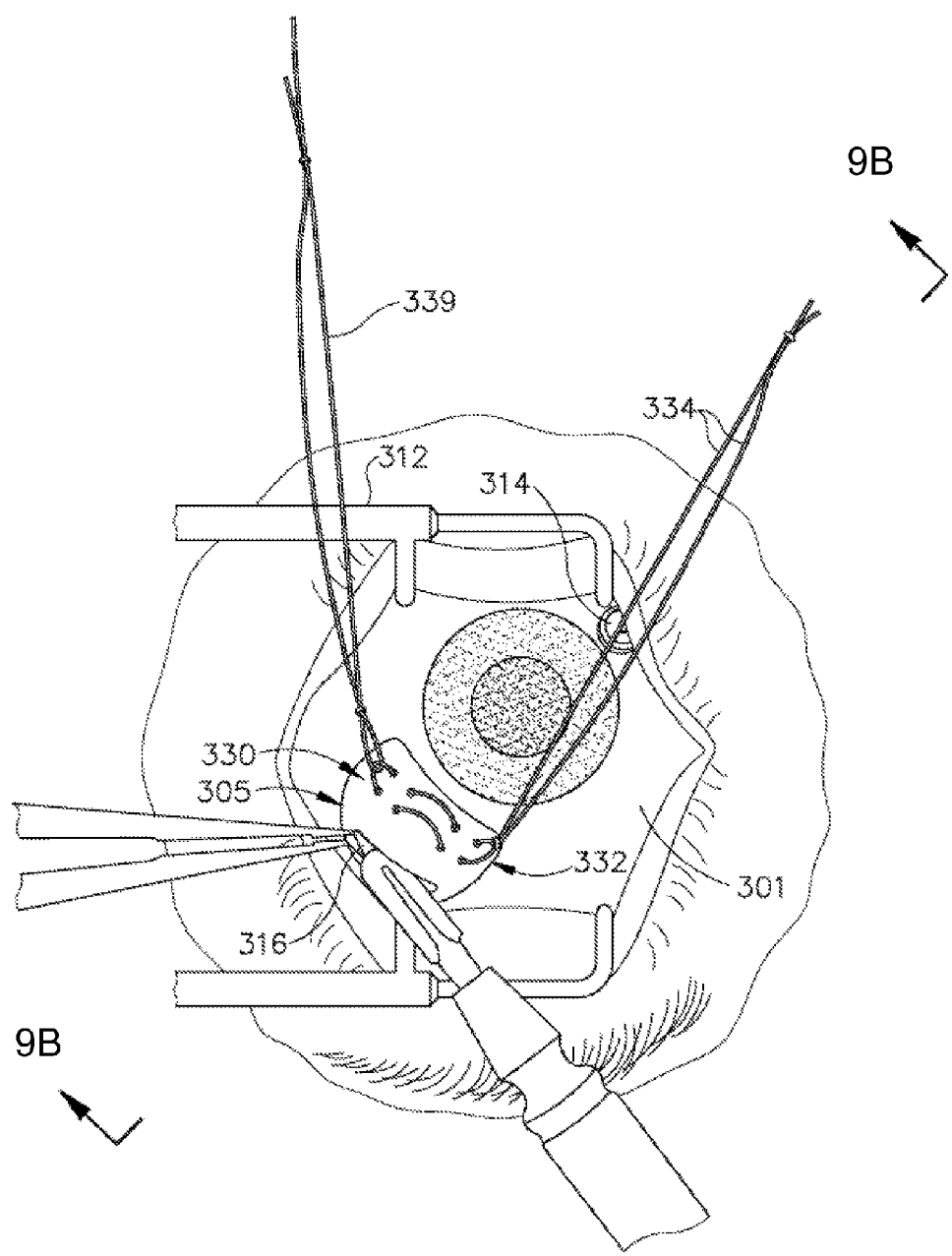
FIG. 8E depicts a top plan view of the eye of FIG. 8A, with a sclerotomy being performed.

FIG. 8D shows a completed suture loop assembly (330). As will be described in greater detail below, suture loop assembly (330) is generally configured to guide cannula (20) of instrument (10) through a sclerotomy and into eye (301). An exemplary procedure that may be employed to create the suture loop assembly (330) that is shown in FIG. 8D is described in U.S. patent application Ser. No. 14/619,256, entitled "Method and Apparatus for Suprachoroidal Administration of Therapeutic Agent," filed Feb. 11, 2015, published as U.S. Pub. No. 2015/0223977 on Aug. 13, 2015, the disclosure of which is incorporated by reference herein. Once suture loop assembly (330) has been attached to eye (301), a sclerotomy may be performed on eye (301). As seen in FIG. 8E, eye (301) is cut between sclerotomy markers (329) using a conventional scalpel (313) or other suitable cutting instrument. Although sclerotomy markers (329) are shown as comprising two discrete dots, it should be understood that in other examples, markers (329) may comprise any other type of markings such as a solid, dotted or dashed line. The sclerotomy procedure forms a small incision (316) through sclera (304) of eye (301). As can best be seen in FIG. 9B, the sclerotomy is preformed with particular care to avoid penetration of the choroid (306). Thus, the sclerotomy procedure provides access to the space between sclera (304) and choroid (306). Once incision (316) is made in eye (301), a blunt dissection may optionally be performed to locally separate sclera (304) from choroid (306). Such a dissection may be performed using a small blunt elongate instrument, as will be apparent to those of ordinary skill in the art in view of the teachings herein.

Figure 8F:
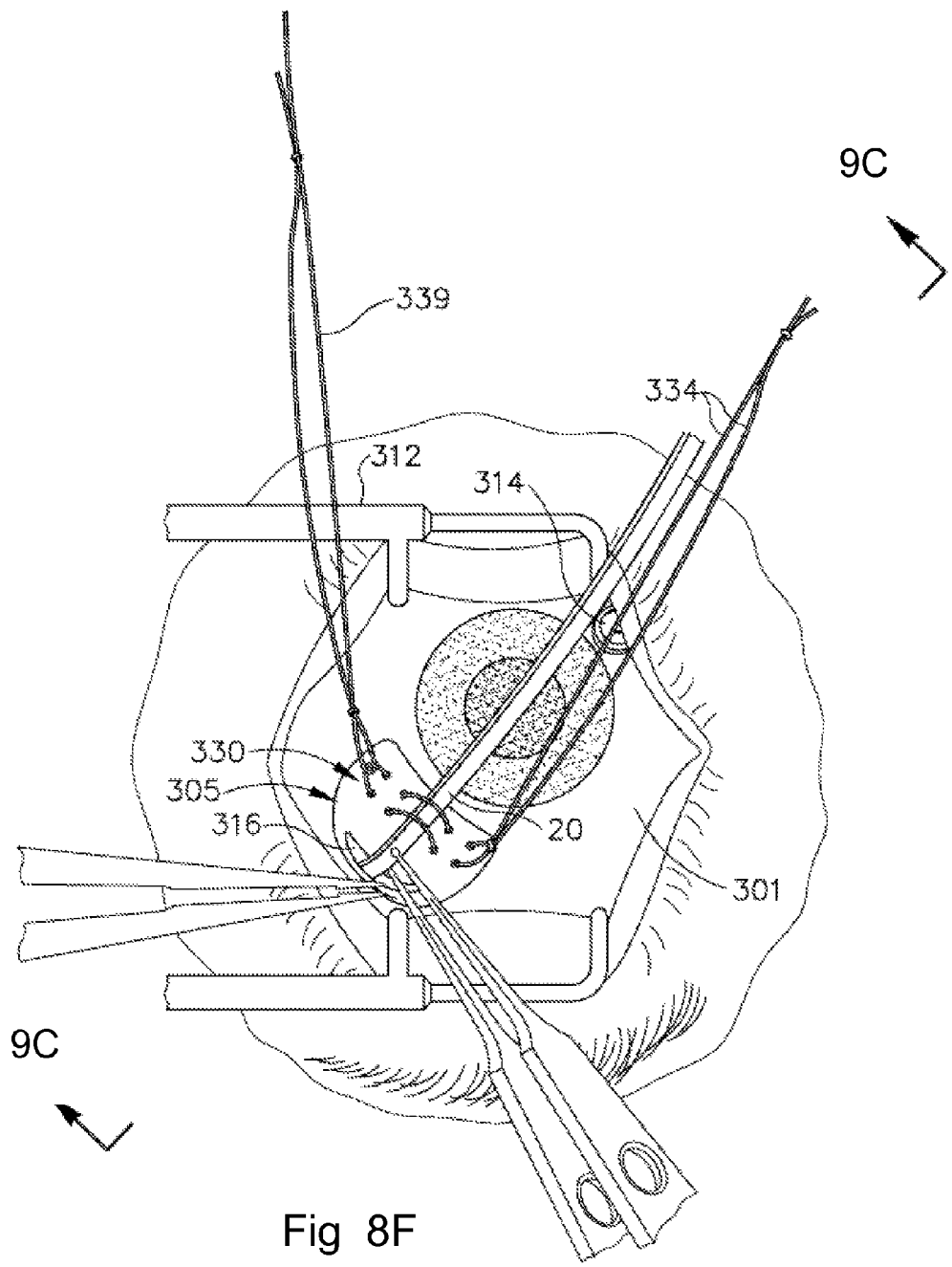
FIG. 8F depicts a top plan view of the eye of FIG. 8A, with the instrument of FIG. 1 being inserted through the sclerotomy opening and in between the sclera and choroid of the eye.

With the sclerotomy procedure performed, an operator may insert cannula (20) of instrument (10) through incision (316) and into the space between sclera (304) and choroid (306). As can be seen in FIG. 8F, cannula (20) is directed through guide loops (336) of suture loop assembly (330) and into incision (316). As described above, guide loops (336) may stabilize cannula (20). Additionally, guide loops (336) maintain cannula (20) in a generally tangential orientation relative to incision (316). Such tangential orientation may reduce trauma as cannula (20) is guided through incision (316) to stabilize cannula (20) and to prevent damage to surrounding tissue. As cannula (20) is inserted into incision (316) through guide loops (336), an operator may use forceps or other instruments to further guide cannula (20) along an atraumatic path. Of course, use of forceps or other instruments is merely optional, and may be omitted in some examples. Although not shown, it should be understood that in some examples cannula (20) may include one or more markers on the surface of cannula (20) to indicate various depths of insertion. While merely optional, such markers may be desirable to aid an operator in identifying the proper depth of insertion as cannula (20) is guided along an atraumatic path. For instance, the operator may visually observe the position of such markers in relation to guide loops (336) and/or in relation to incision (316) as an indication of the depth to which cannula (20) is inserted in eye (301). By way of example only, one such marker may correspond to an approximately 6 mm depth of insertion of cannula (20).

Once cannula (20) is at least partially inserted into eye (301), an operator may insert an optical fiber (315) into eye chandelier port (314) the fiber (315) had not yet been inserted at this stage. With eye chandelier port (314) in place and assembled with optical fiber (315), an operator may activate eye chandelier port (314) by directing light through optical fiber (315) to provide illumination of eye (301) and thereby visualize the interior of eye (301). Further adjustments to the positioning of cannula (20) may optionally be made at this point to ensure proper positioning relative to the area of geographic atrophy of retina (308). In some instances, the operator may wish to rotate the eye (301), such as by pulling on sutures (334, 339), to direct the pupil of the eye (301) toward the operator in order to optimize visualization of the interior of the eye (301) via the pupil.

Figure 8G:
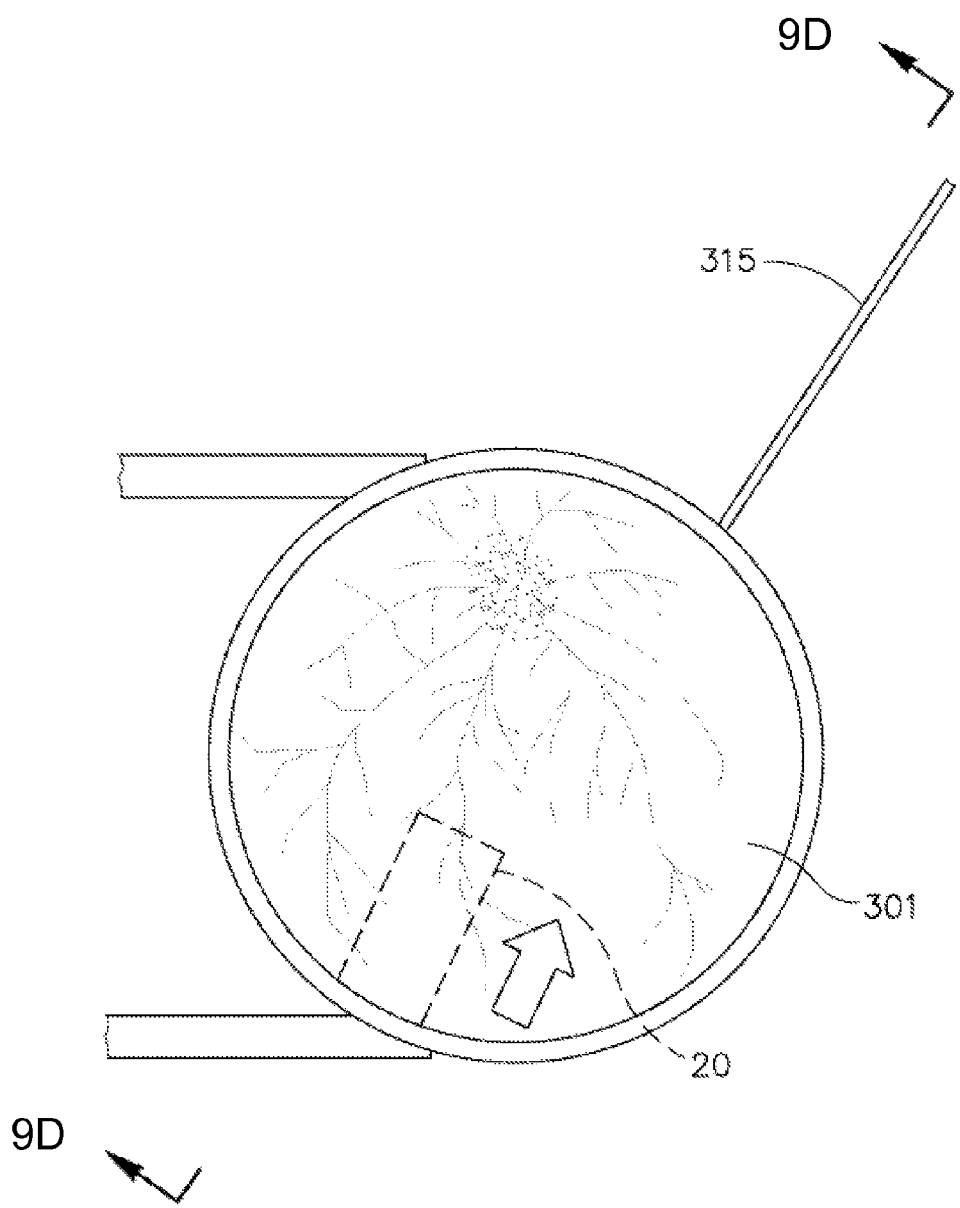
FIG. 8G depicts a top plan view of the eye of FIG. 8A, with the instrument of FIG. 1 under direct visualization at the back of the eye, between the sclera and choroid.
Figure 9A:
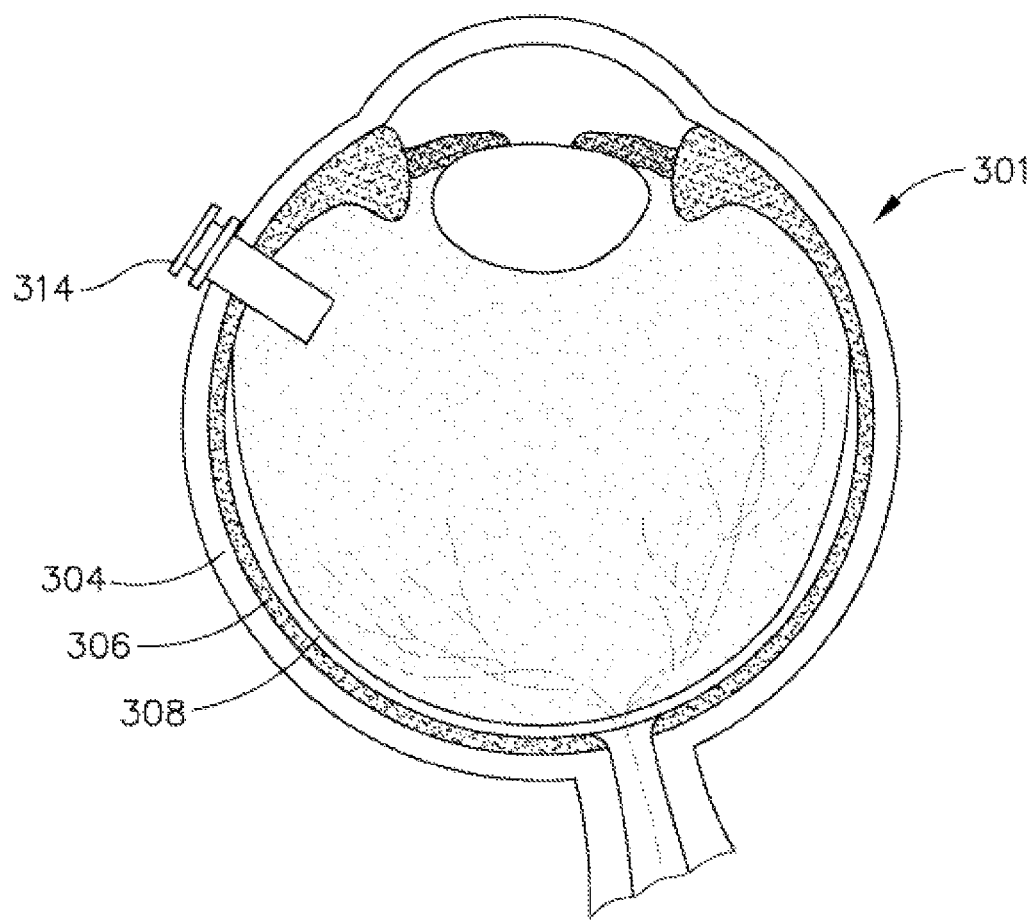
FIG. 9A depicts a cross-sectional view of the eye of FIG. 8A, with the cross-section taken along line 9A-9A of FIG. 8A.
Figure 9B:
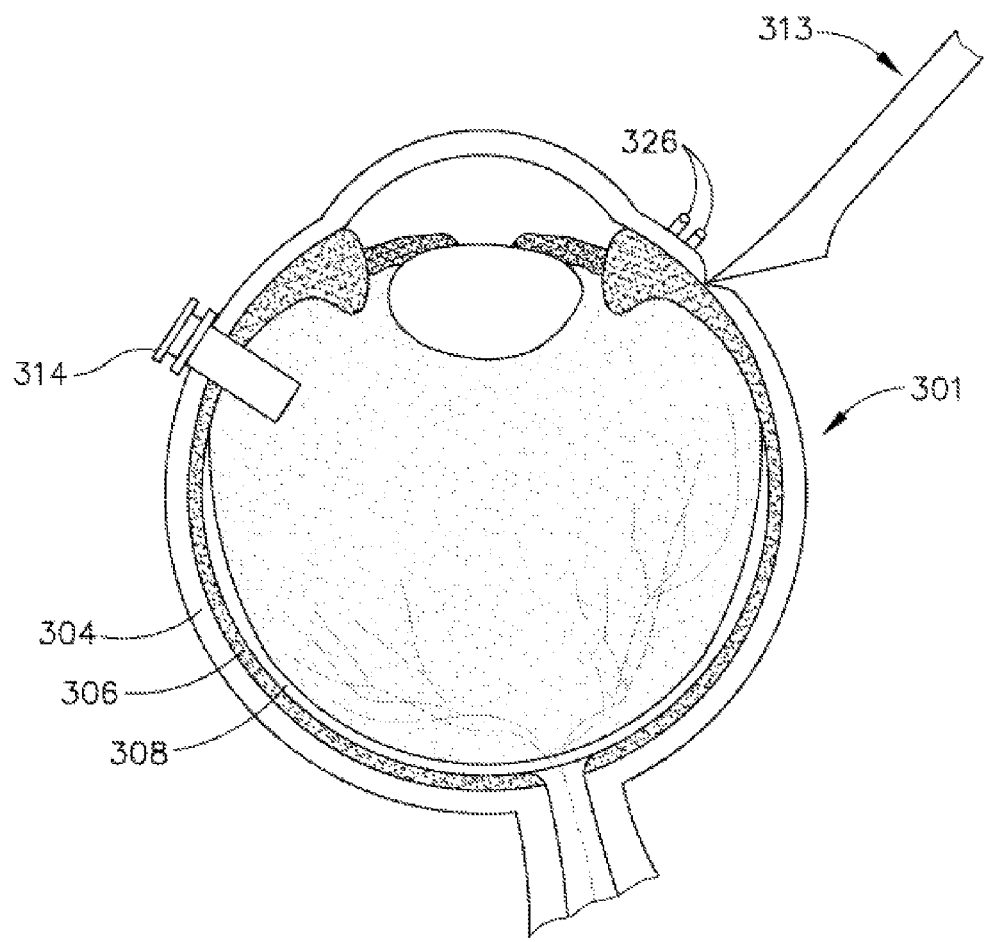
FIG. 9B depicts a cross-sectional view of the eye of FIG. 8A, with the cross-section taken along line 9B-9B of FIG. 8E.
Figure 9C:
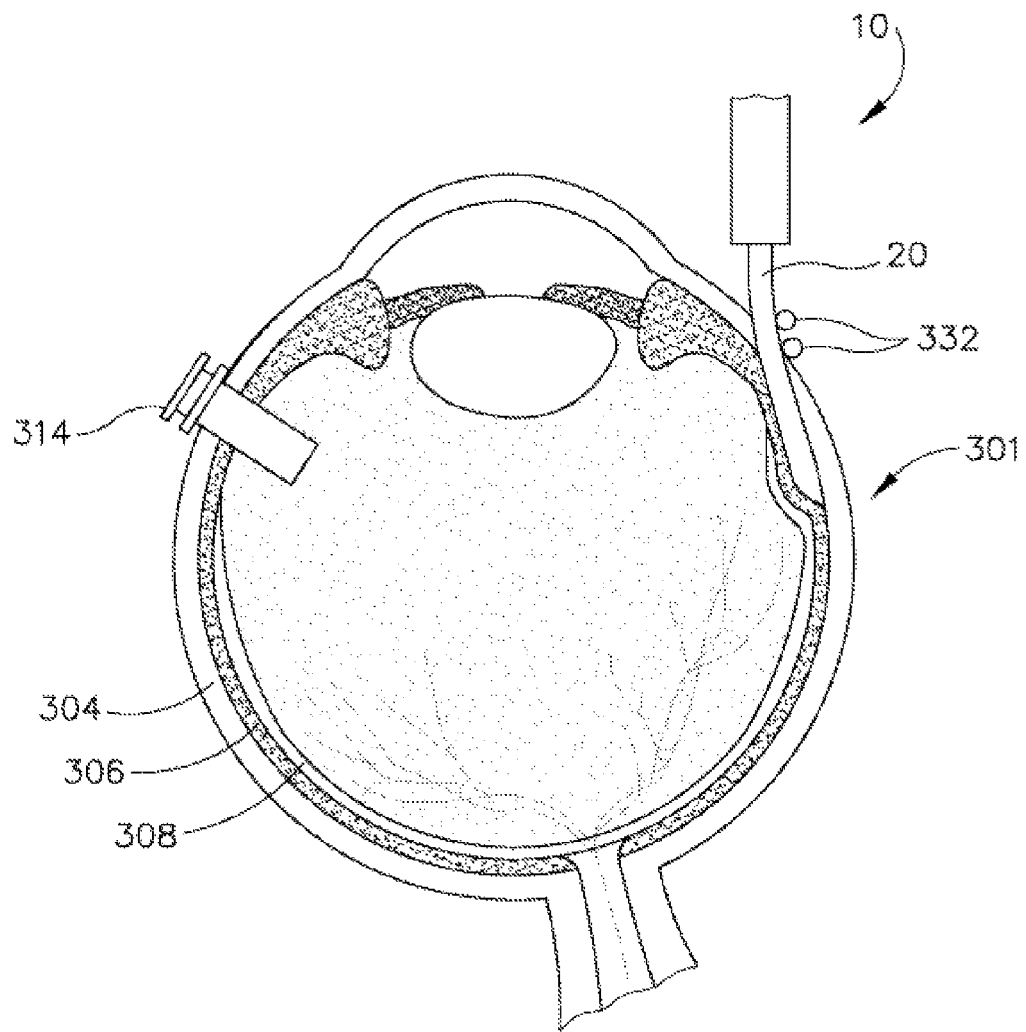
FIG. 9C depicts a cross-sectional view of the eye of FIG. 8A, with the cross-section taken along line 9C-9C of FIG. 8F.
Figure 9D:
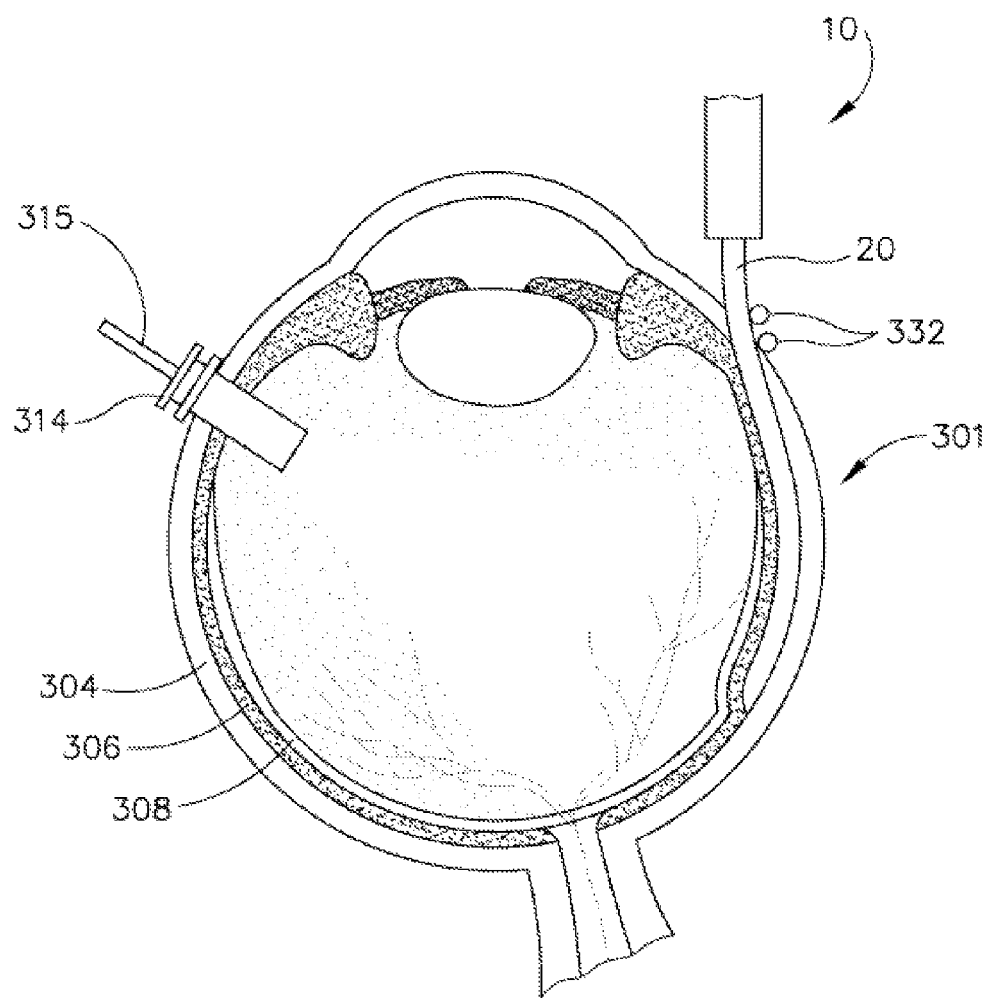
FIG. 9D depicts a cross-sectional view of the eye of FIG. 8A, with the cross-section taken along line 9D-9D of FIG. 8G.
Figure 9E:
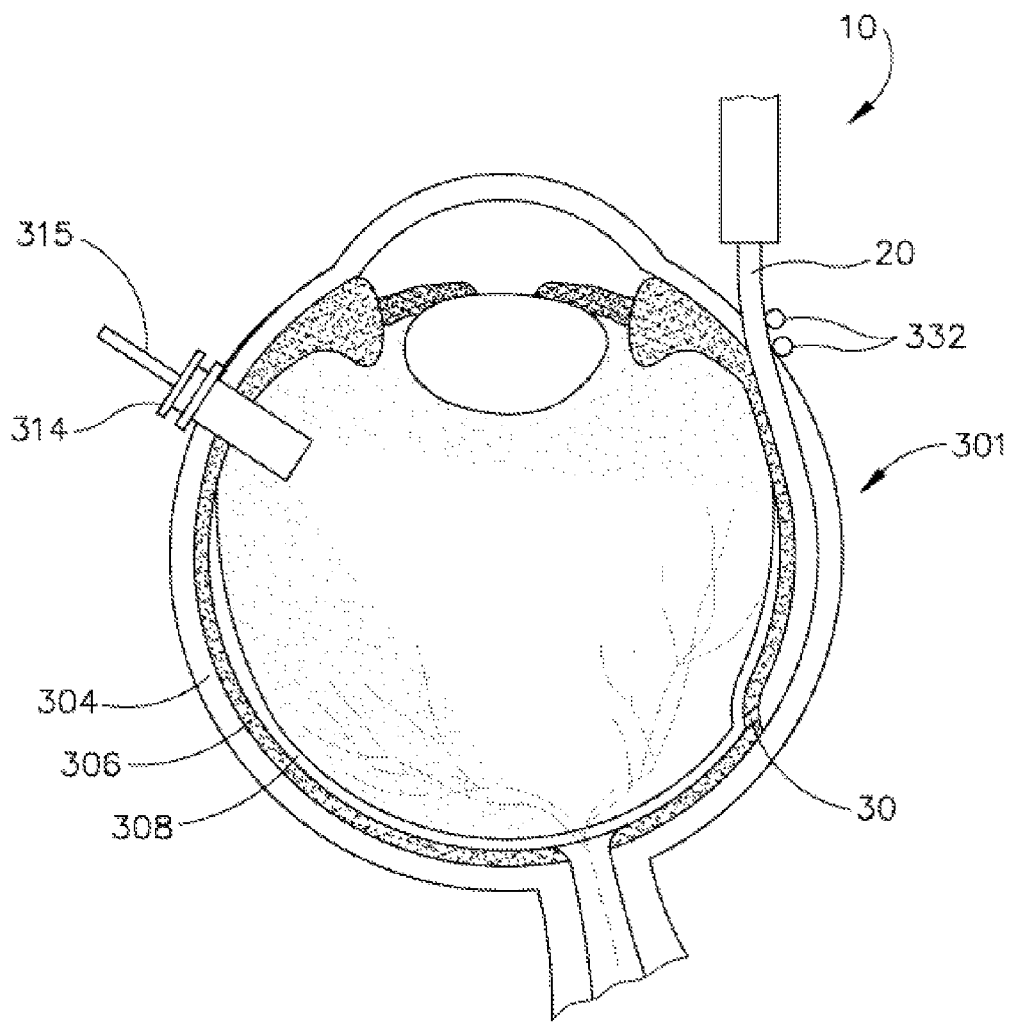
FIG. 9E depicts a cross-sectional view of the eye of FIG. 8A, with the cross-section taken along line 9E-9E of FIG. 8H.

FIGS. 8G and 9C-9D show cannula (20) as it is guided between sclera (304) and choroid (306) to the delivery site for the therapeutic agent. In the present example, the delivery site corresponds to a generally posterior region of eye (301) adjacent to an area of geographic atrophy of retina (308). In particular, the delivery site of the present example is superior to the macula, in the potential space between the neurosensory retina and the retinal pigment epithelium layer. FIG. 8G shows eye (301) under direct visualization through a microscope directed through the pupil of eye (301), with illumination provided through fiber (315) and port (314). As can be seen, cannula (20) is at least partially visible through a retina (308) and choroid (306) of eye (301). Thus, an operator may track cannula (20) as it is advanced through eye (301) from the position shown in FIG. 9C to the position shown in 9D. Such tracking may be enhanced in versions where an optical fiber (34) is used to emit visible light through the distal end of cannula (20).

Figure 8H:
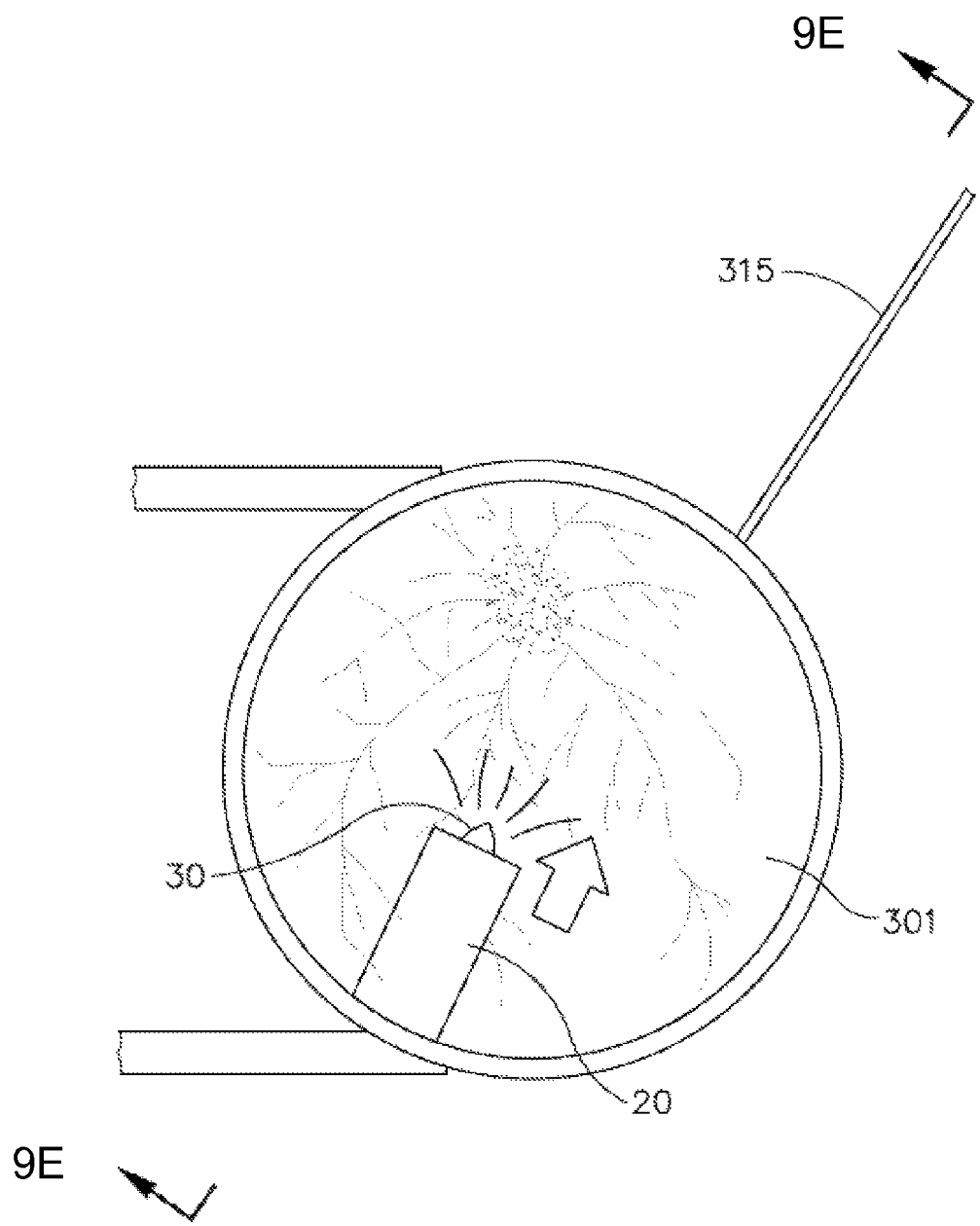
FIG. 8H depicts a top plan view of the eye of FIG. 8A, with the needle of the instrument of FIG. 1 being advanced under direct visualization at the back of the eye, pressing against the outer surface of the choroid causing the choroid to 'tent'.

Once cannula (20) has been advanced to the delivery site as shown in FIG. 9D, an operator may advance needle (30) of instrument (10) as described above with respect to FIGS. 3-4. As can be seen in FIGS. 8H-8I, 9E, and 10A, needle (30) is advanced relative to cannula (20) such that needle (30) pierces through choroid (306) without penetrating retina (308). Immediately prior to penetrating choroid (306), needle (30) may appear under direct visualization as "tenting" the surface of choroid (306), as can be seen in FIG. 8H. In other words, needle (30) may deform choroid (306) by pushing upwardly on choroid, providing an appearance similar to a tent pole deforming the roof of a tent. Such a visual phenomenon may be used by an operator to identify whether choroid (306) is about to be pierced and the location of any eventual piercing. The particular amount of needle (30) advancement sufficient to initiate "tenting" and subsequent piercing of choroid (306) may be of any suitable amount as may be determined by a number of factors such as, but not limited to, general patient anatomy, local patient anatomy, operator preference, and/or other factors. As described above, a merely exemplary range of needle (30) advancement may be between approximately 0.25 mm and approximately 10 mm; or more particularly between approximately 2 mm and approximately 6 mm.

Figure 8I:
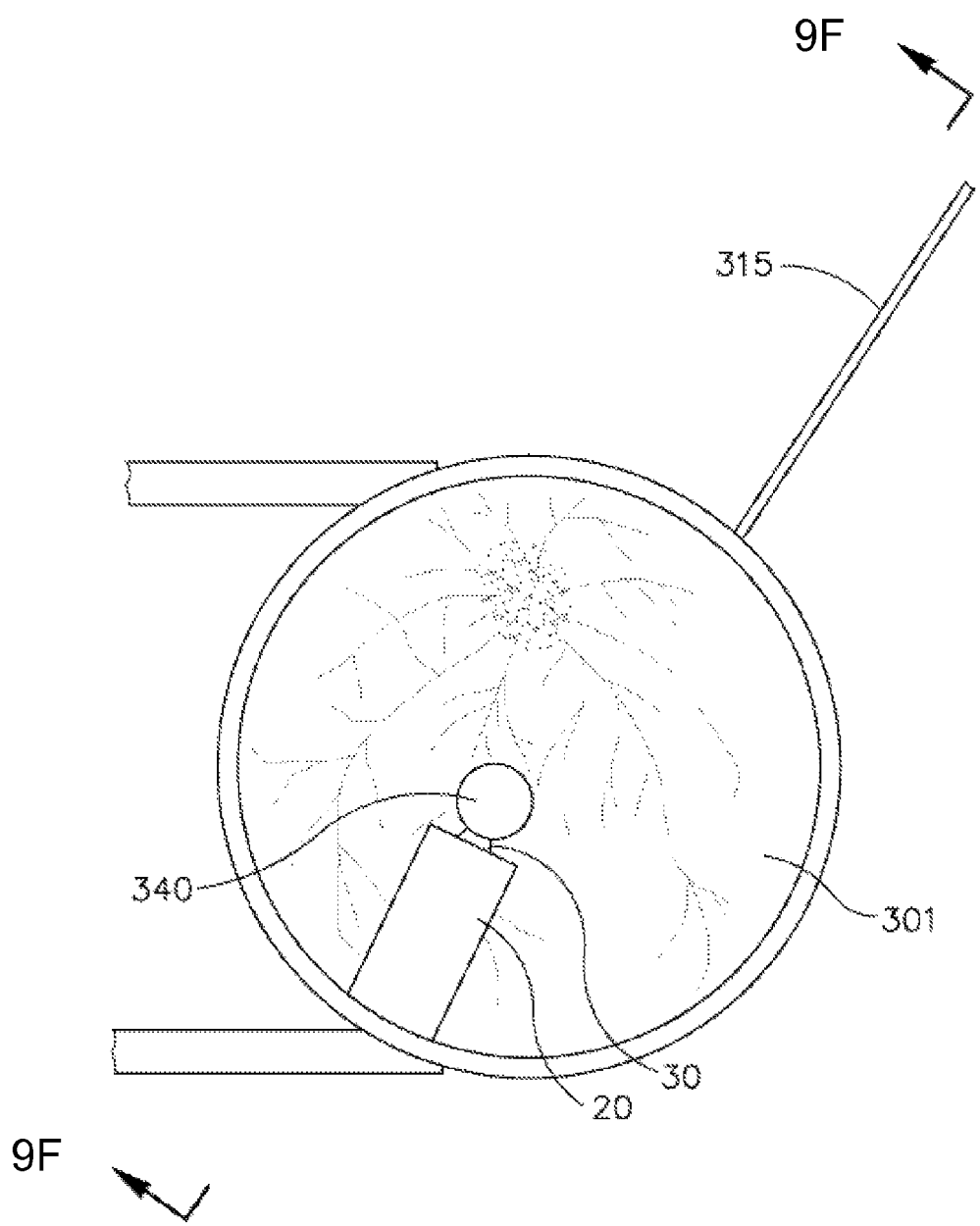
FIG. 8I depicts a top plan view of the eye of FIG. 8A, with the needle dispensing a leading bleb under direct visualization at the back of the eye, the needle between the sclera and choroid, and the leading bleb in the sub retinal space between the choroid and a retina.
Figure 9F:
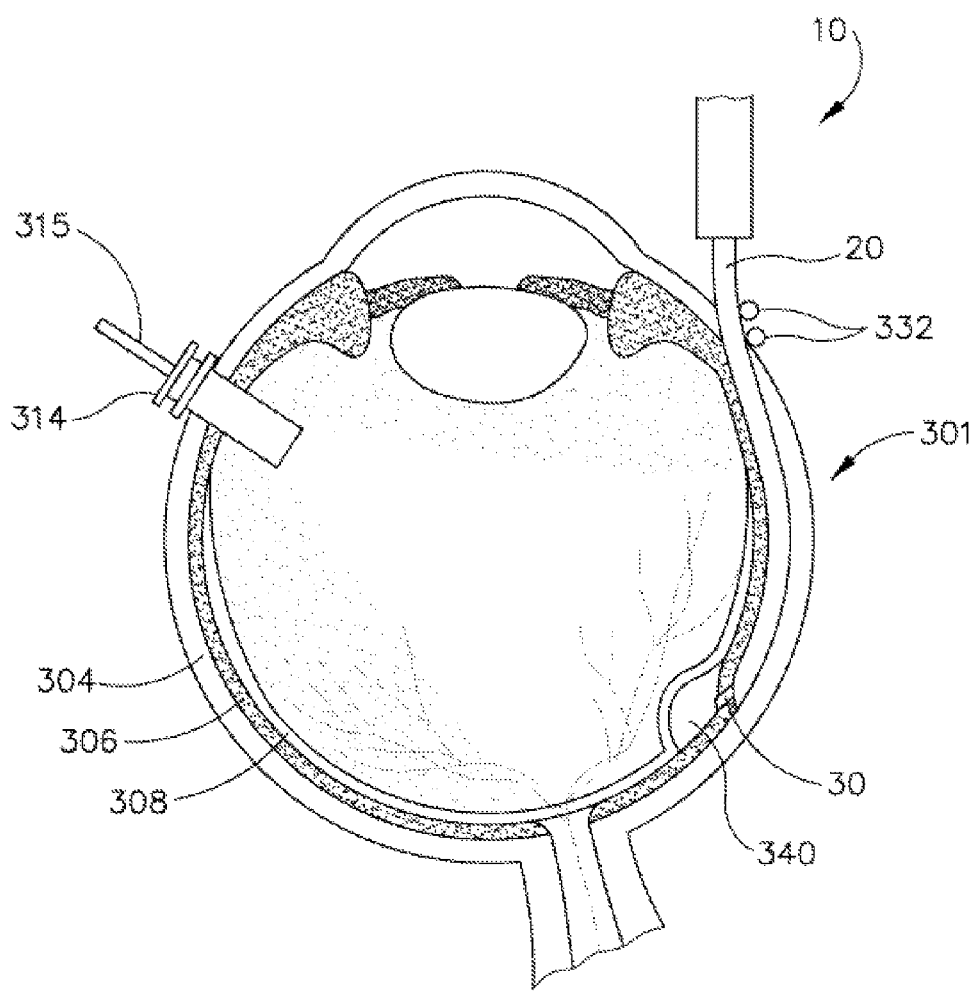
FIG. 9F depicts a cross-sectional view of the eye of FIG. 8A, with the cross-section taken along line 9F-9F of FIG. 8I.
Figure 10B:
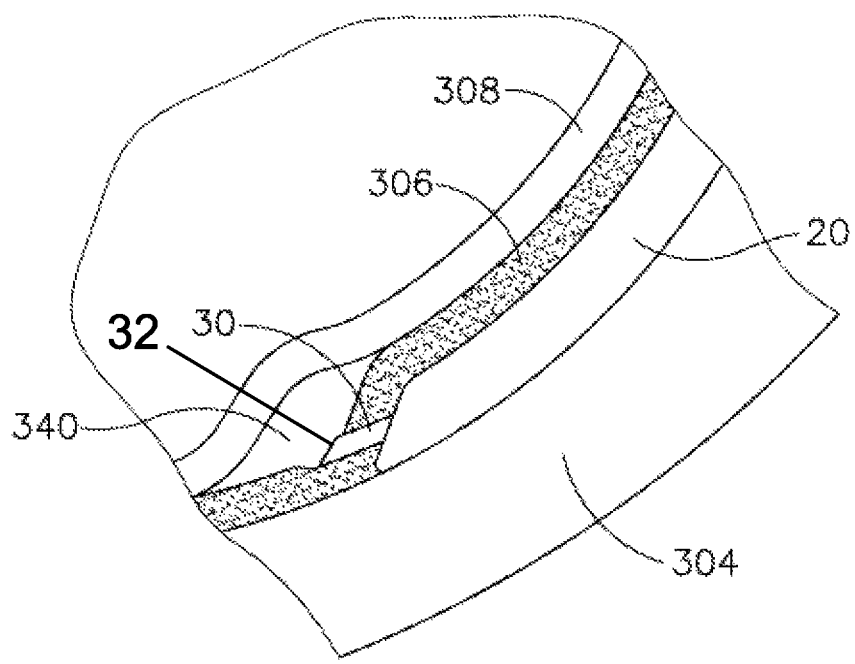
FIG. 10B depicts a detailed cross-sectional view of the eye of FIG. 8A depicted in the state shown in FIG. 9F.

In the present example, after the operator has confirmed that needle (30) has been properly advanced by visualizing the tenting effect described above, the operator infuses a balanced salt solution (BSS) or other similar solution as needle (30) is advanced relative to cannula (20). Such a BSS solution may form a leading bleb (340) ahead of needle (30) as needle (30) is advanced through choroid (306). Leading bleb (340) may be desirable for two reasons. First, as shown in FIGS. 8I, 9F, and 10B, leading bleb (340) may provide a further visual indicator to an operator to indicate when needle (30) is properly positioned at the delivery site. Second, leading bleb (340) may provide a barrier between needle (30) and retina (308) once needle (30) has penetrated choroid (306). Such a barrier may push the retinal wall outwardly (as is best seen in FIGS. 9F and 10B), thereby minimizing the risk of retinal perforation as needle (30) is advanced to the delivery site. In some versions, a foot pedal is actuated in order to drive leading bleb (340) out from needle (30). Alternatively, other suitable features that may be used to drive leading bleb (340) out from needle (30) will be apparent to those of ordinary skill in the art in view of the teachings herein.

Once the operator visualizes leading bleb (340), the operator may cease infusion of BSS, leaving a pocket of fluid as can be seen in FIGS. 8I, 9F, and 10B. Next, a therapeutic agent (341) may be infused by actuating a syringe or other fluid delivery device as described above with respect to instrument (10). The particular therapeutic agent (341) delivered may be any suitable therapeutic agent configured to treat an ocular condition. Some merely exemplary suitable therapeutic agents may include, but are not necessarily limited to, drugs having smaller or large molecules, therapeutic cell solutions, certain gene therapy solutions, and/or any other suitable therapeutic agent as will be apparent to those of ordinary skill in the art in view of the teachings herein. By way of example only, the therapeutic agent (341) may be provided in accordance with at least some of the teachings of U.S. Pat. No. 7,413,734, entitled "Treatment of Retinitis Pigmentosa with Human Umbilical Cord Cells," issued Aug. 19, 2008, the disclosure of which is incorporated by reference herein.

Figure 8J:
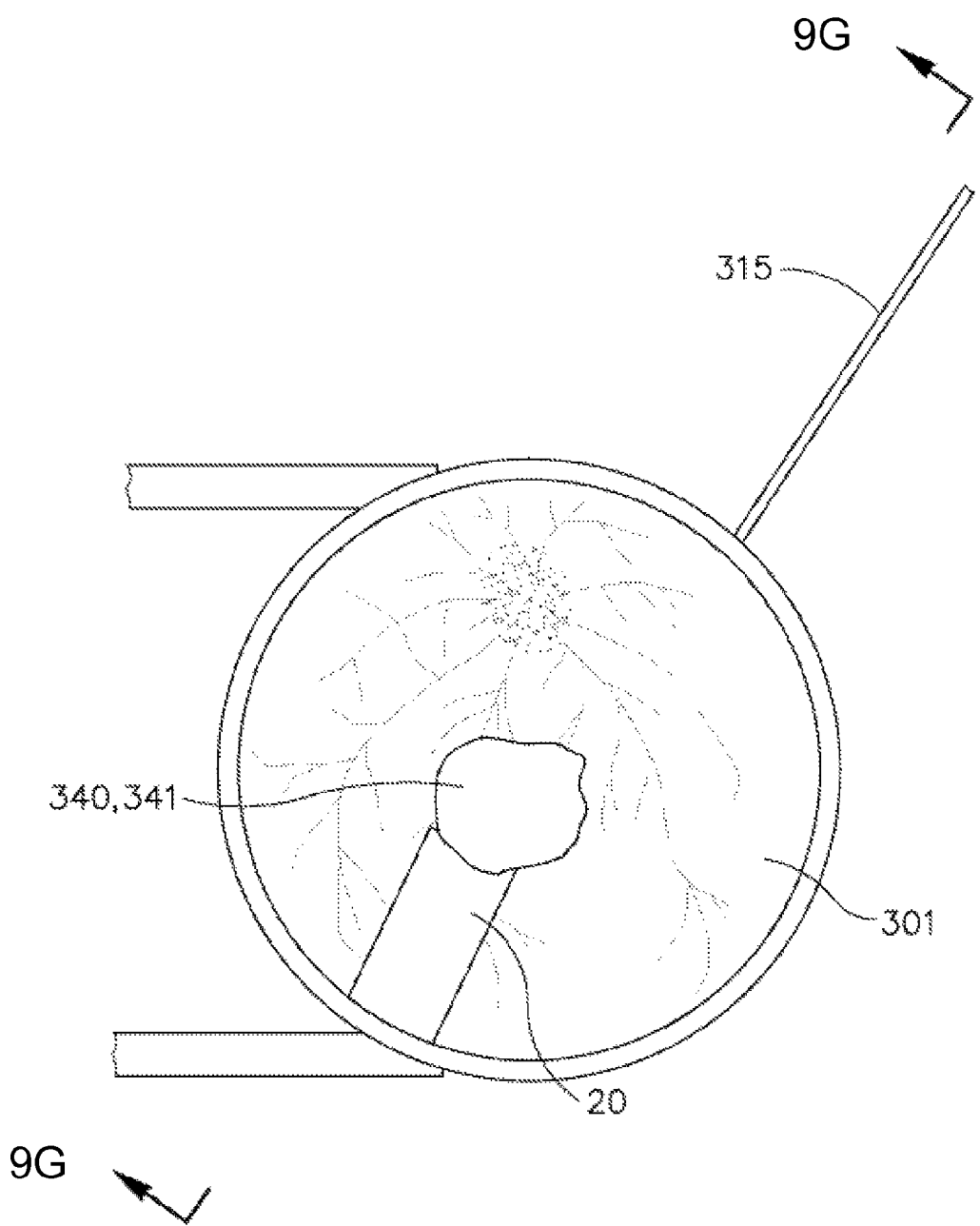
FIG. 8J depicts a top plan view of the eye of FIG. 8A, with the needle dispensing a therapeutic agent to the eye at the back of the eye, between the sclera and choroid.
Figure 9G:
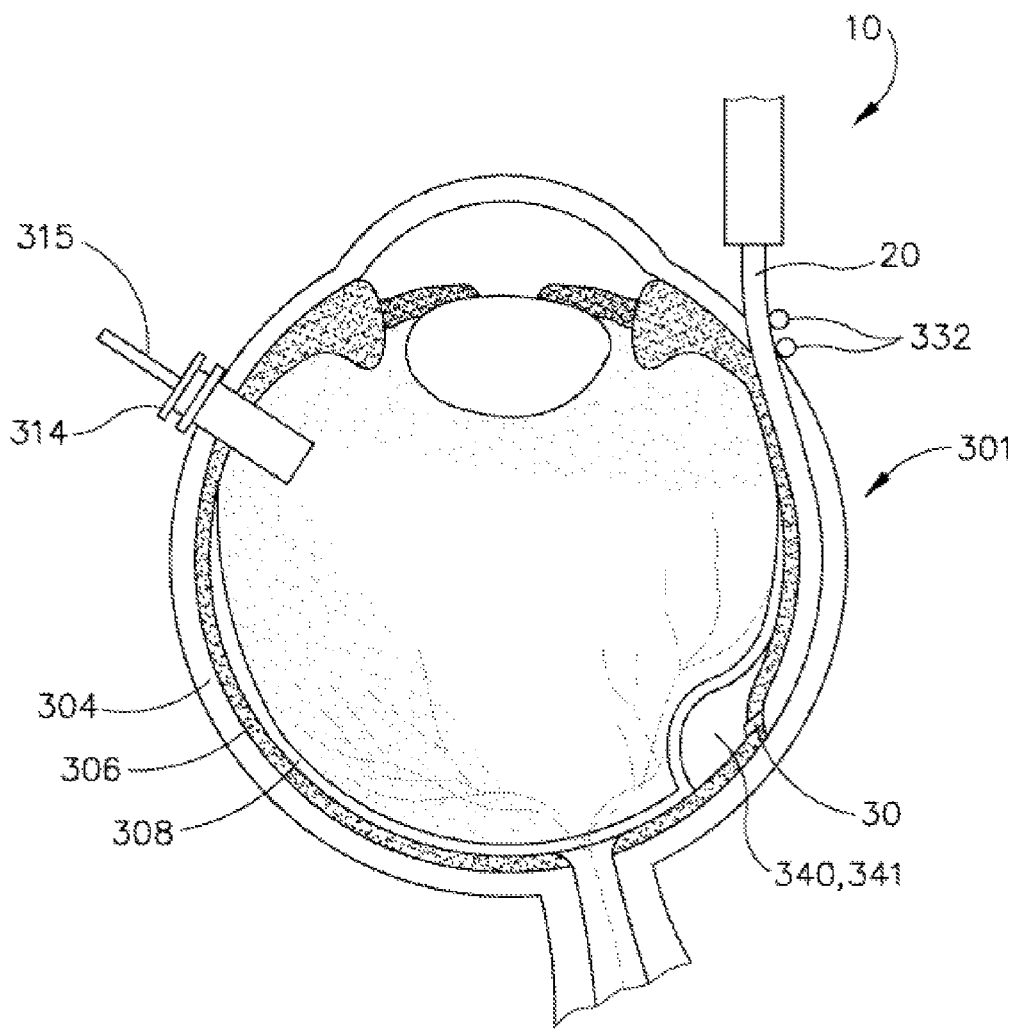
FIG. 9G depicts a cross-sectional view of the eye of FIG. 8A, with the cross-section taken along line 9G-9G of FIG. 8J.
Figure 10C:
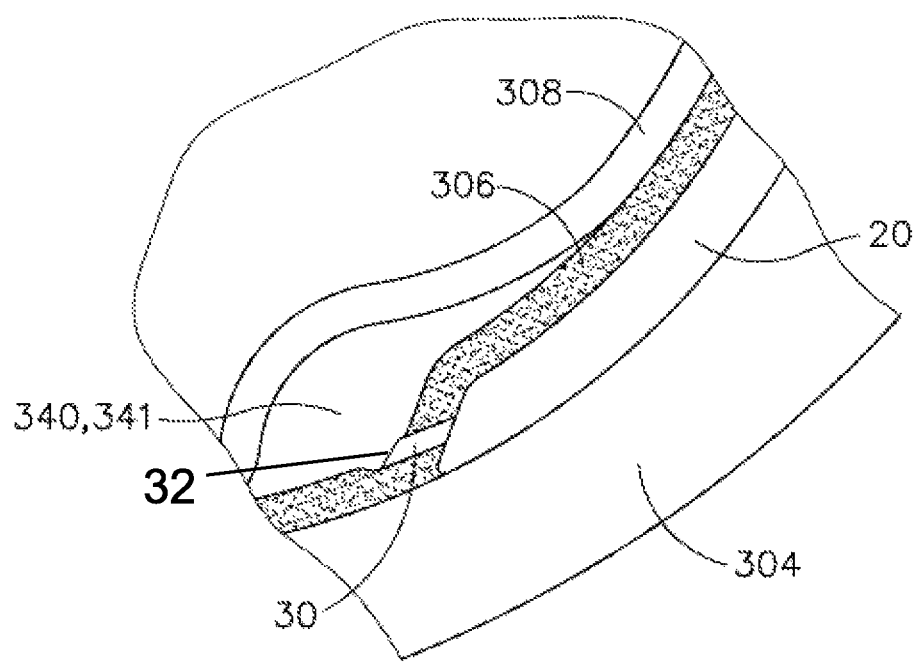
FIG. 10C depicts a detailed cross-sectional view of the eye of FIG. 8A depicted in the state shown in FIG. 9G.

In the present example, the amount of therapeutic agent (341) that is ultimately delivered to the delivery site is approximately 50 µL, although any other suitable amount may be delivered. In some versions, a foot pedal is actuated in order to drive agent (341) out from needle (30). Alternatively, other suitable features that may be used to drive agent (341) out from needle (30) will be apparent to those of ordinary skill in the art in view of the teachings herein. Delivery of therapeutic agent may be visualized by an expansion of the pocket of fluid as can be seen in FIGS. 8J, 9G, and 10C. As shown, therapeutic agent (341) essentially mixes with the fluid of leading bleb (340) as therapeutic agent (341) is injected into the suprachoroidal space.

Once delivery is complete, needle (20) may be retracted by sliding actuation assembly (60) proximally relative to body (40); and cannula (30) may then be withdrawn from eye (301). It should be understood that because of the size of needle (20), the site where needle (20) penetrated through choroid (306) is self sealing, such that no further steps need be taken to seal the delivery site through choroid (306). Suture loop assembly (330) and chandelier (314) may be removed, and incision (316) in the sclera (304) may be closed using any suitable conventional techniques.

As noted above, the foregoing procedure may be carried out to treat a patient having macular degeneration. In some such instances, the therapeutic agent (341) that is delivered by needle (20) may comprise cells that are derived from postpartum umbilicus and placenta. As noted above, and by way of example only, the therapeutic agent (341) may be provided in accordance with at least some of the teachings of U.S. Pat. No. 7,413,734, entitled "Treatment of Retinitis Pigmentosa with Human Umbilical Cord Cells," issued Aug. 19, 2008, the disclosure of which is incorporated by reference herein. Alternatively, needle (20) may be used to deliver any other suitable substance or substances, in addition to or in lieu of those described in U.S. Pat. No. 7,413,734 and/or elsewhere herein. By way of example only, therapeutic agent (341) may comprise various kinds of drugs including but not limited to small molecules, large molecules, cells, and/or gene therapies. It should also be understood that macular degeneration is just one merely illustrative example of a condition that may be treated through the procedure described herein. Other biological conditions that may be addressed using the instruments and procedures described herein will be apparent to those of ordinary skill in the art.

Figure 11:
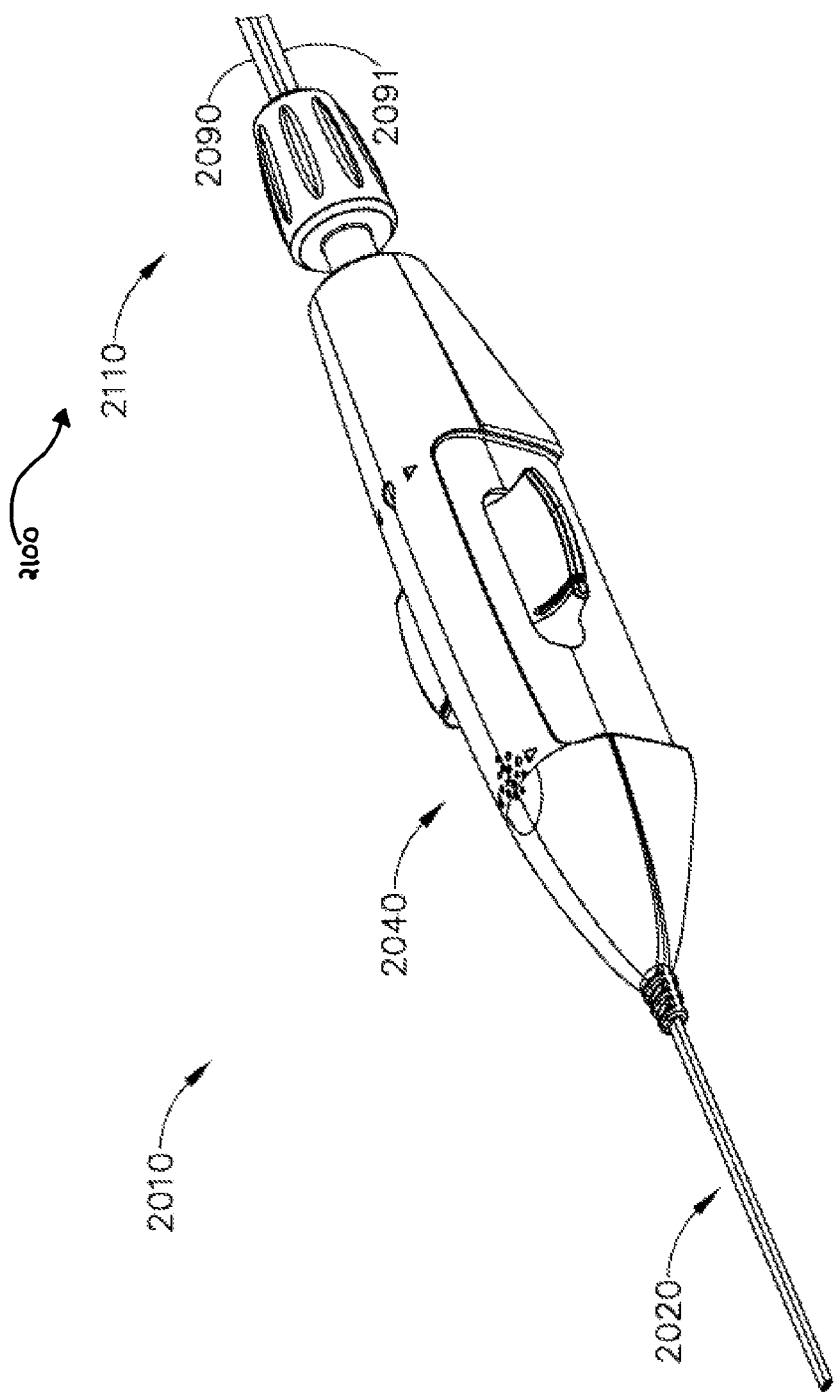
FIG. 11 depicts a perspective view of another exemplary alternative instrument for subretinal administration of a therapeutic agent from a suprachoroidal approach.

IV. Exemplary Therapeutic Agent Delivery Instrument with Rotary Needle Actuation Feature and Valve Assembly In some examples, it may be desirable to vary certain components or features of the instruments described herein. For instance, it may be desirable to utilize instruments similar to instrument (10) with alternative mechanisms to actuate needle (30) and/or a valve assembly to selectively control the flow of leading bleb (340) and therapeutic agent (341). FIG. 11 shows an exemplary alternative instrument (2010) that is similar to instrument (10) described above, except that instrument (2010) of this example includes an alternative assembly (2100) to actuate a needle (2030); and instrument (2010) also includes a valve assembly (2200).

While certain features and operabilities of instrument (2010) are described below, it should be understood that, in addition to or in lieu of the following, instrument (2010) may be configured and/or operable in accordance with any of the teachings of U.S. patent application Ser. No. 14/619,256, entitled "Method and Apparatus for Suprachoroidal Administration of Therapeutic Agent," filed Feb. 11, 2015, published as U.S. Pub. No. 2015/0223977 on Aug. 13, 2015, the disclosure of which is incorporated by reference herein. Like with instrument (10), instrument (2010) of the present example is generally usable in the procedure described herein to administer a therapeutic agent subretially from a suprachoroidal approach. It should therefore be understood that instrument (2010) may be readily used in place of instrument (10) to perform the medical procedure described above with reference to FIGS. 8A-10C. Like instrument (10), instrument (2010) of this example comprises a cannula (2020), a body (2040), and an actuation assembly (2100). Cannula (2020) includes a nitinol needle (2030) extending therethrough. In the present example, cannula (2020) and needle (2030) are substantially identical to cannula (20) and needle (30) described above.

One difference between instrument (10) and instrument (2010) is that actuation assembly (2100) of instrument (2010) is rotatable instead of being slidable. Additionally, instrument (2010) includes a valve assembly (2200) that is operable to change the fluid state of needle (2030). Actuation assembly (2100) is generally operable to translate valve assembly (2200) longitudinally to thereby translate needle (2030) longitudinally relative to cannula (2020) through rotation of a knob member (2110).

When actuation assembly (2100) is in the proximal position, an operator may rotate knob member (2110) in either a counter clockwise or clockwise direction. If knob member (2110) is rotated in the counter clockwise direction, rotation member (2110) will merely rotate freely. To begin advancement of actuation assembly (2100), valve assembly (2200), and needle (2030), the operator may rotate knob member (2110) in the clockwise direction. Clockwise rotation of knob member (2110) will act to translate knob member (2110) distally and will also act to translate valve assembly (2200) and needle (2030) distally. The operator may continue clockwise rotation of knob member (2110) to drive needle (2030) out of the distal end of cannula (2020). Once needle (2030) has been advanced to its furthest distal position relative to the distal end of cannula (2020), further clockwise rotation of knob member (2110) will merely result in free rotation of knob member (2110) due to slipping of clutch features that are integrated into actuation assembly (2100). With needle (2030) in the distal position, the operator may actuate valve assembly (2200) as described below to enable the delivery of leading bleb (430) and therapeutic agent (341) via needle (2030) as described above.

After leading bleb (430) and therapeutic agent (341) have been delivered, the operator may then wish to retract needle (2030). Counter clockwise rotation of knob member (2110) will cause proximal translation of actuation assembly (2100), valve assembly (2200), and needle (2030) relative to body (2040). As actuation assembly (2100) is rotated to actuate valve assembly (2200) and needle (2030), valve assembly and needle (2030) remain substantially rotationally stationary relative to body (2040). It should also be understood that although rotation member (2110) of the present example is described as being manually rotated, rotation member (2110) may be rotated via a motor and/or some other motive source. Thus, it should be understood that translation of needle (2030) may be mechanically/electrically driven via a servomotor. Such a servo control may be manually operated. Additionally or alternatively, such a servo controller may be operated via a computer acting on feedback from instrument (2010) or any other component described herein.

Figure 12:
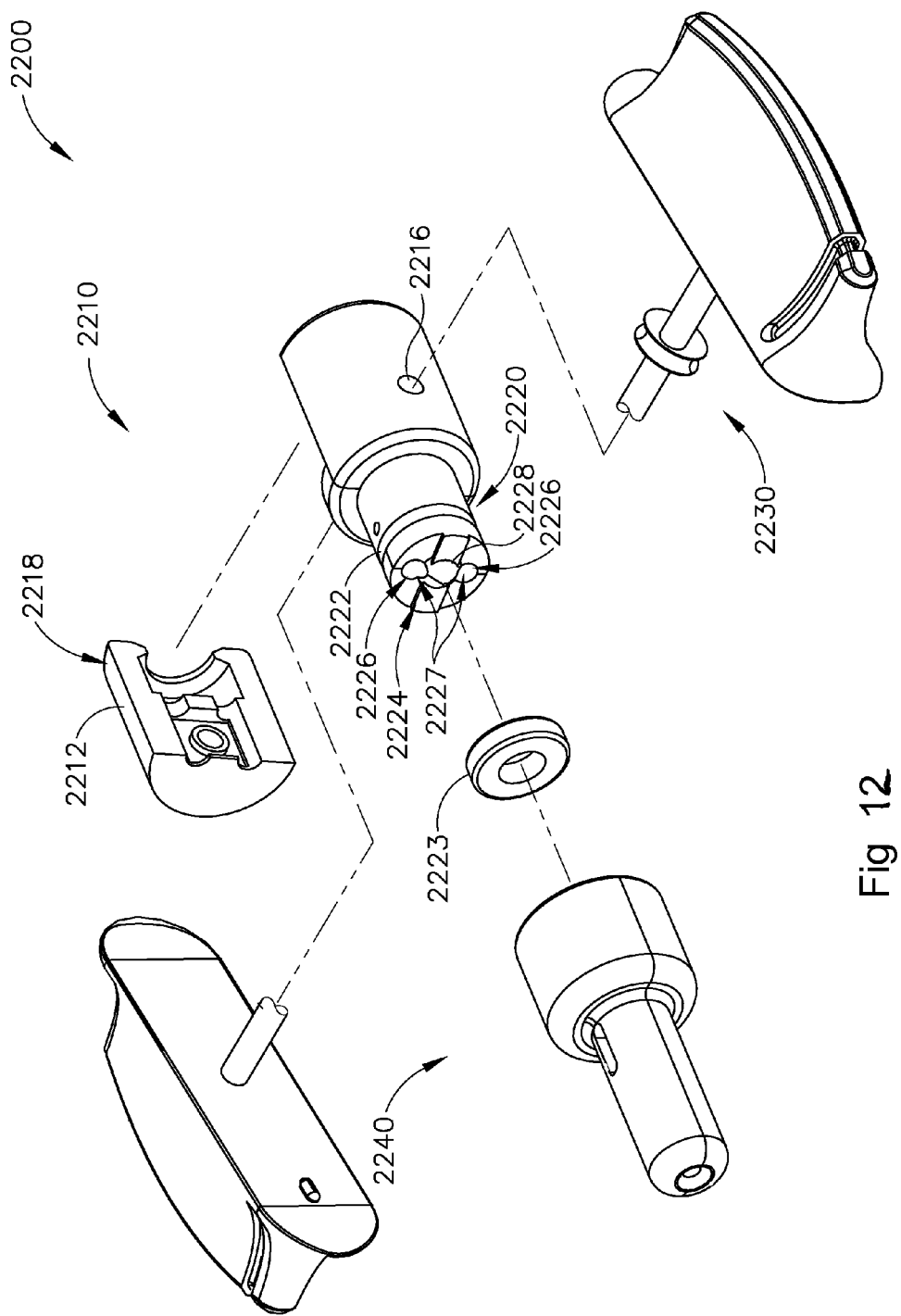
FIG. 12 depicts an exploded perspective view of an exemplary valve assembly of the instrument of FIG. 11.
Figure 13:
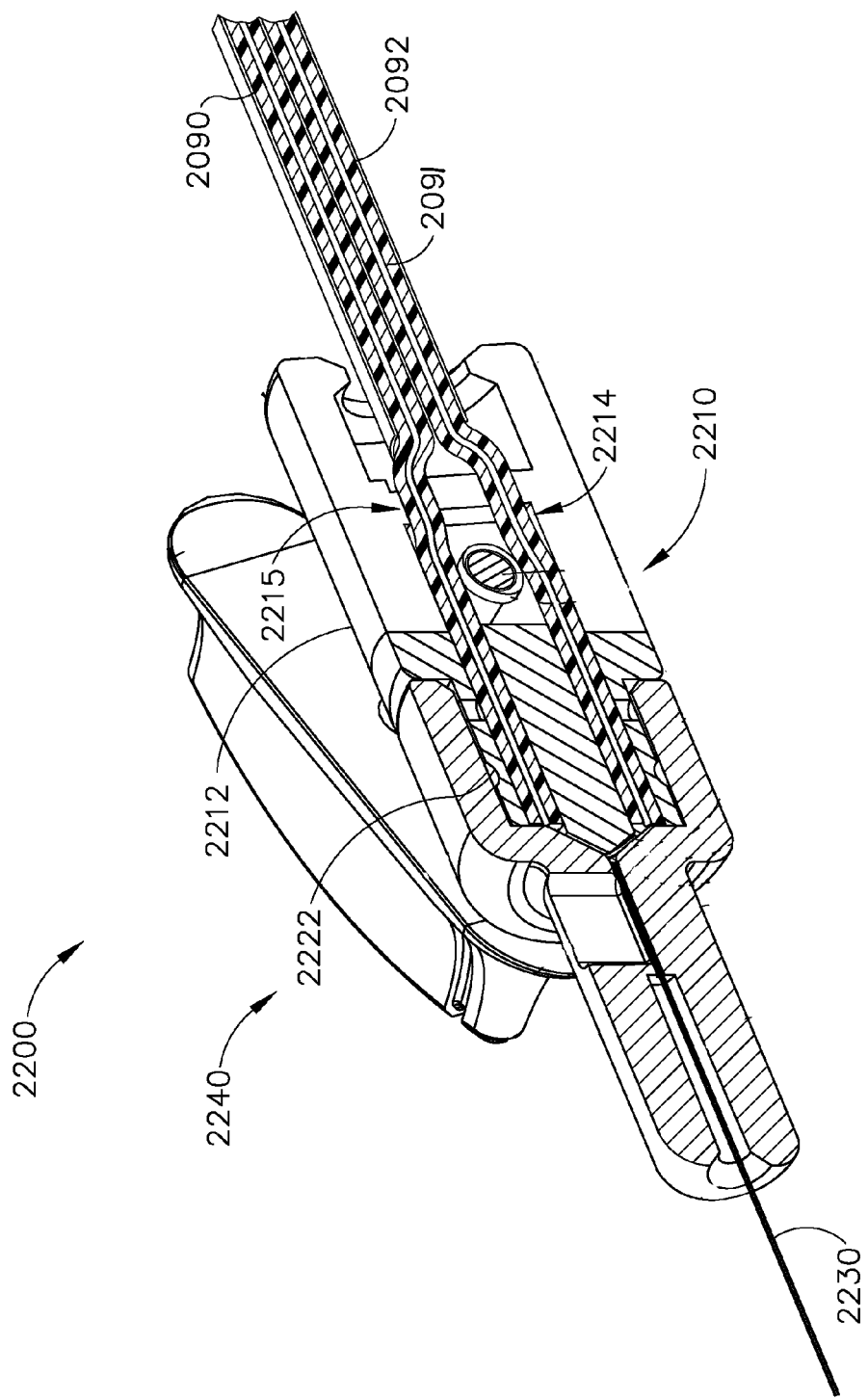
FIG. 13 depicts a perspective cross-sectional view of the valve assembly of FIG. 12 with additional fluid communication features.

As can best be seen in FIGS. 12-13, valve assembly (2200) comprises a valve body (2210), a valve actuator (2230), and a needle coupler (2240). In particular, valve body (2210) comprises a valve housing (2212), a cylindrical attachment member (2218) extending proximally from valve housing (2212), and a coupler insert (2220). Valve housing (2212) is generally cylindrical in shape. As can best be seen in FIG. 13, valve housing (2212) defines a chamber (2214) that is configured to receive a pair of supply tubes (2090, 2091) and valve actuator (2230). Each side of valve housing (2212) includes a pair of actuator openings (2216), which are configured to rotatably receive valve actuator (2230) through valve housing (2212) and into chamber (2214). In the present example, first supply tube (2090) is configured to couple with a source of bleb fluid (340) (e.g., BSS); while second supply tube (2091) is configured to couple with a source of therapeutic agent (341). It should be understood that each fluid supply tube (2090, 2091) may include a conventional luer feature and/or other structures permitting fluid supply tubes (2090, 2091) to be coupled with respective fluid sources.

The proximal end of valve housing (2212) defines a tube opening (2215) that extends into chamber (2214). As can be seen tube opening (2215) is configured to receive a tube (2092) which houses supply tubes (2090, 2091). Tube (2092) surrounds supply tubes (2090, 2091) to prevent inadvertent rotation of supply tubes (2090, 2091) by actuation assembly (2100). In the present example, tube opening (2215) is sized such that tube (2092) is secured to valve housing (2212) by a compression or interference fit. In other examples, tube (2092) may alternatively be secured within tube opening (2215) by adhesive bonding, welding, mechanical fasteners, and/or using any other suitable structures or techniques.

Coupler insert (2220) extends distally from valve housing (2212) and is generally configured for insertion into the proximal end of needle coupler (2240). Coupler insert (2220) is generally cylindrical in shape and comprises an annular recess (2222) and a distal tip (2224). Annular recess (2222) receives a rubber o-ring (2223) or other sealing device. Distal tip (2224) includes a pair of fluid openings (2226) and a conical protrusion (2228). Fluid openings (2226) open to a pair of tube lumens (2227), which extend through coupler insert (2220). Tube lumens (2227) are generally configured to receive supply tubes (2090, 2091) such that fluid may be delivered to needle coupler (2240) via fluid openings (2226). Conical protrusion (2228) is configured to be received by needle coupler (2240) to direct fluid from fluid openings (2226) and into needle (2030). Therefore, either supply tube (2090, 2091) is configured to direct fluid directly into needle (2030) without having to remove needle (2030) from the surgical site. Therefore, bleb fluid (340) can be injected into the subretinal space of a patient and therapeutic agent (341) can be injected immediately afterwards without the need of removing needle (2030). Valve actuator (2230) is rotatable relative to valve body (2210) to selectively pinch and un-pinch supply tubes (2090, 2091), thereby selectively preventing or permitting the flow of bleb fluid (340) and therapeutic agent (341) through tubes (2090, 2091) to reach needle (2030).

V. Exemplary Instrument for Delivery of Therapeutic Agent from Trans-Retinal Approach In some instances, it may be desirable to deliver bleb fluid (340) and therapeutic agent (341) to the subretinal space from a transvitreal, trans-retinal approach. For instance, it may be desirable to deliver bleb fluid (340) and therapeutic agent (341) to the subretinal space through a pars plana transvitreal procedure. It may further be desirable to deliver both bleb fluid (340) and therapeutic agent (341) to the subretinal space from a trans-retinal approach using just one single tip of just one single instrument, such that the subretinal space only needs to be entered one single time. Providing this capability may require the convergence of two or more lumens into a single lumen in the single tip, with bleb fluid (340) being fed through one lumen and therapeutic agent (341) being fed through the other lumen. As noted above, providing leading bleb (340) in the subretinal space could be beneficial to gain separation between the retina and the choroid to create a more forgiving entry portal for therapeutic agent (341) to the subretinal space.

Figure 14:
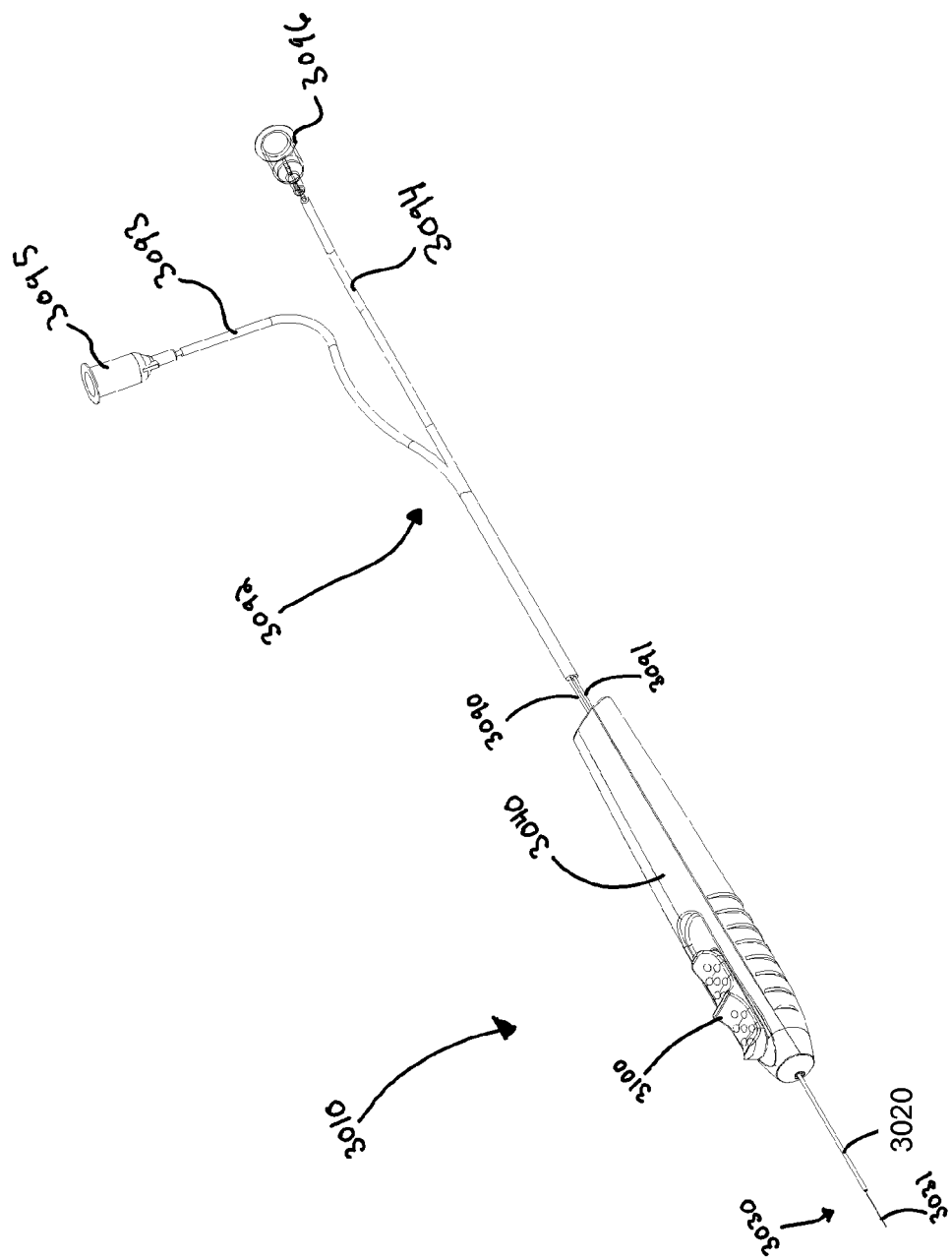
FIG. 14 depicts a perspective view of an exemplary instrument for subretinal administration of a therapeutic agent.

FIGS. 14-22 show an exemplary instrument (3010) that may be used to deliver bleb fluid (340) and therapeutic agent (341) to the subretinal space from a transvitreal, trans-retinal approach via a single lumen in a single tip. As best seen in FIG. 14, instrument (3010) of this example comprises a pair of luer fittings (3095, 3096), a fluid supply guide (3092), supply tubes (3090, 3091) fluidly connected to luer fittings (3095, 3096) respectively, a body (3040), a slider (3100), and a fluid delivery assembly (3030). Luer fittings (3095, 3096) may connect to two different sources of fluid, such as leading bleb (340) fluid and therapeutic fluid (341). Luer fittings (3095, 3096) connect to tubing lines (3093, 3094) respectively, which terminate into fluid supply guide (3092).

While conventional luer fittings (3095, 3096) are used in the present example, any other suitable kind of fittings may be used.

Fluid supply guide (3092) brings together tubing lines (3093, 3094) into a fixed, parallel relationship. Supply tubes (3090, 3091) exit fluid supply guide (3092) and enter body (3040) as will be described in greater detail below. It should be understood that fluid supply guide (3092) provides a dedicated path for fluid communication from tubing line (3093) to supply tube (3090); and from tubing line (3094) to supply tube (3091). Fluid supply guide keeps the path that is associated with tubing line (3093) and supply tube (3090) isolated from the path that is associated with tubing line (3094) and supply tube (3091). The fluid sources that are coupled with luer fittings (3095, 3096) may be pressurized either manually (e.g., such as with a syringe), or automatically (e.g., with a pump). The operator may then choose which fluid source to pressurize to selectively pump fluids (340, 341) to corresponding supply tubes (3090, 3091).

Fluid delivery assembly (3030) comprises an outer cannula (3020) and an inner cannula (3031). Outer cannula (3020) is fixed relative to body (3040). Outer cannula (3020) is sized and configured to pass through a trocar port (318) that is inserted into the eye (301) of a patient Inner cannula (3031) is longitudinally slidable relative to outer cannula (3020) and body (3040). In particular, inner cannula (3031) is longitudinally driven by a slider (3100).

Figure 15A:
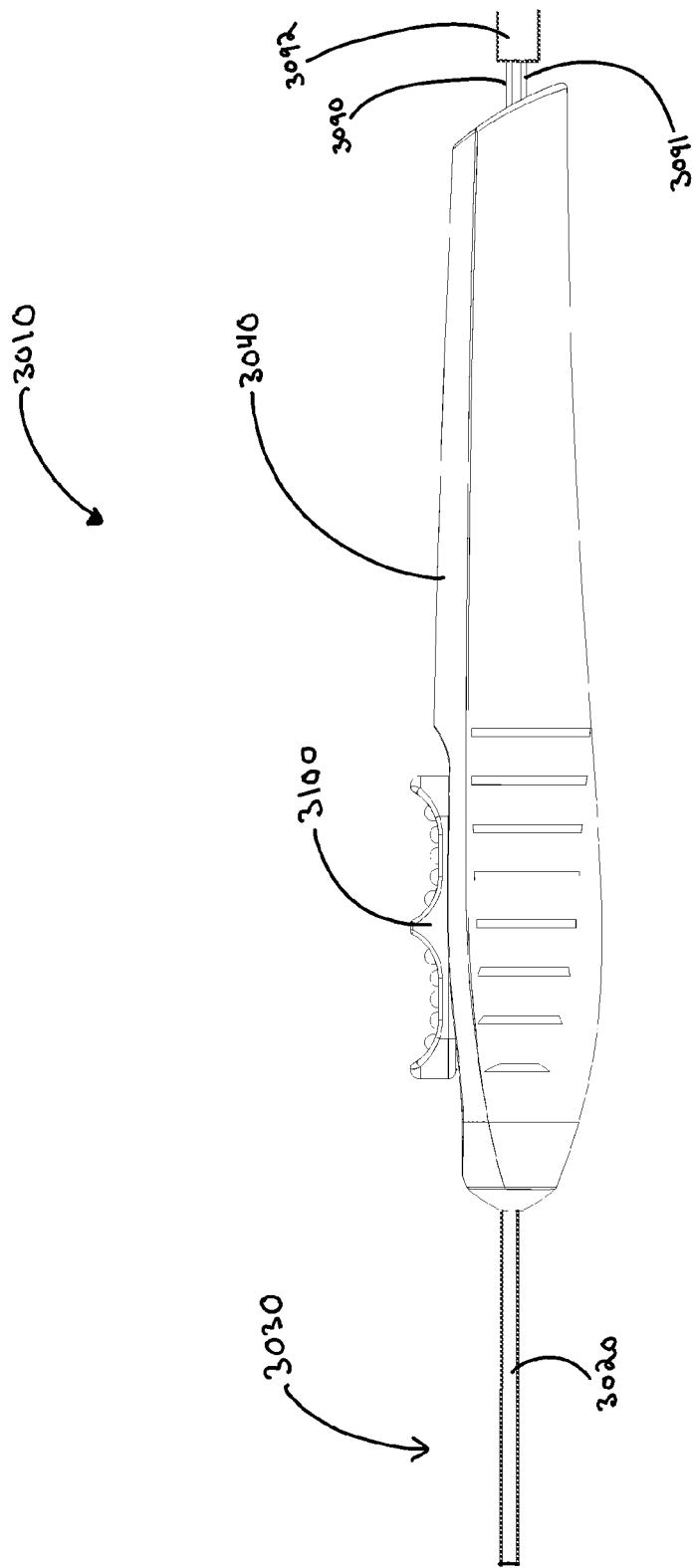
FIG. 15A depicts a side elevational view of the instrument of FIG. 14 with the retinal penetrating element in a retracted position.
Figure 15B:
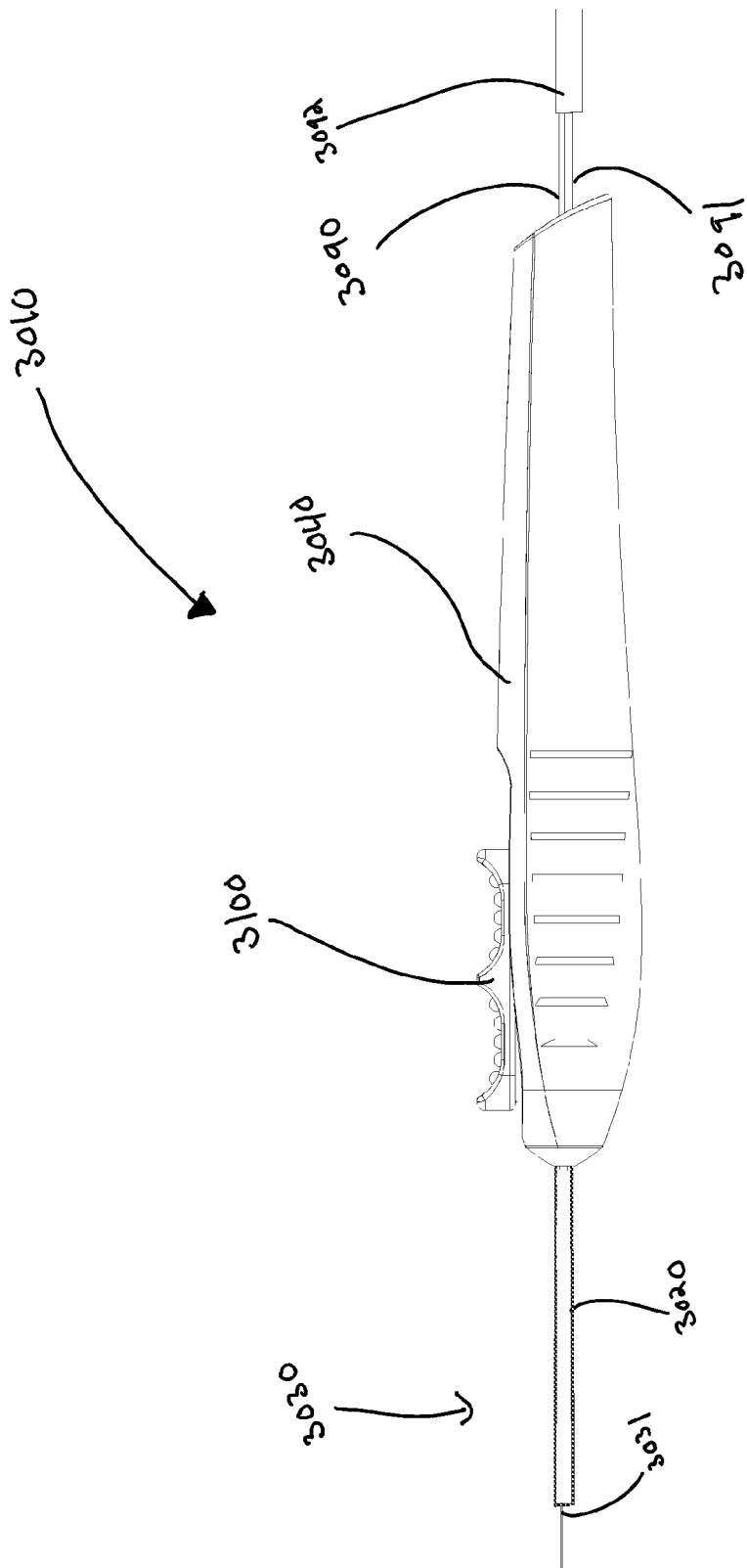
FIG. 15B depicts a side elevational view of the instrument of FIG. 14 with the retinal penetrating element in an extended position.
Figure 16A:
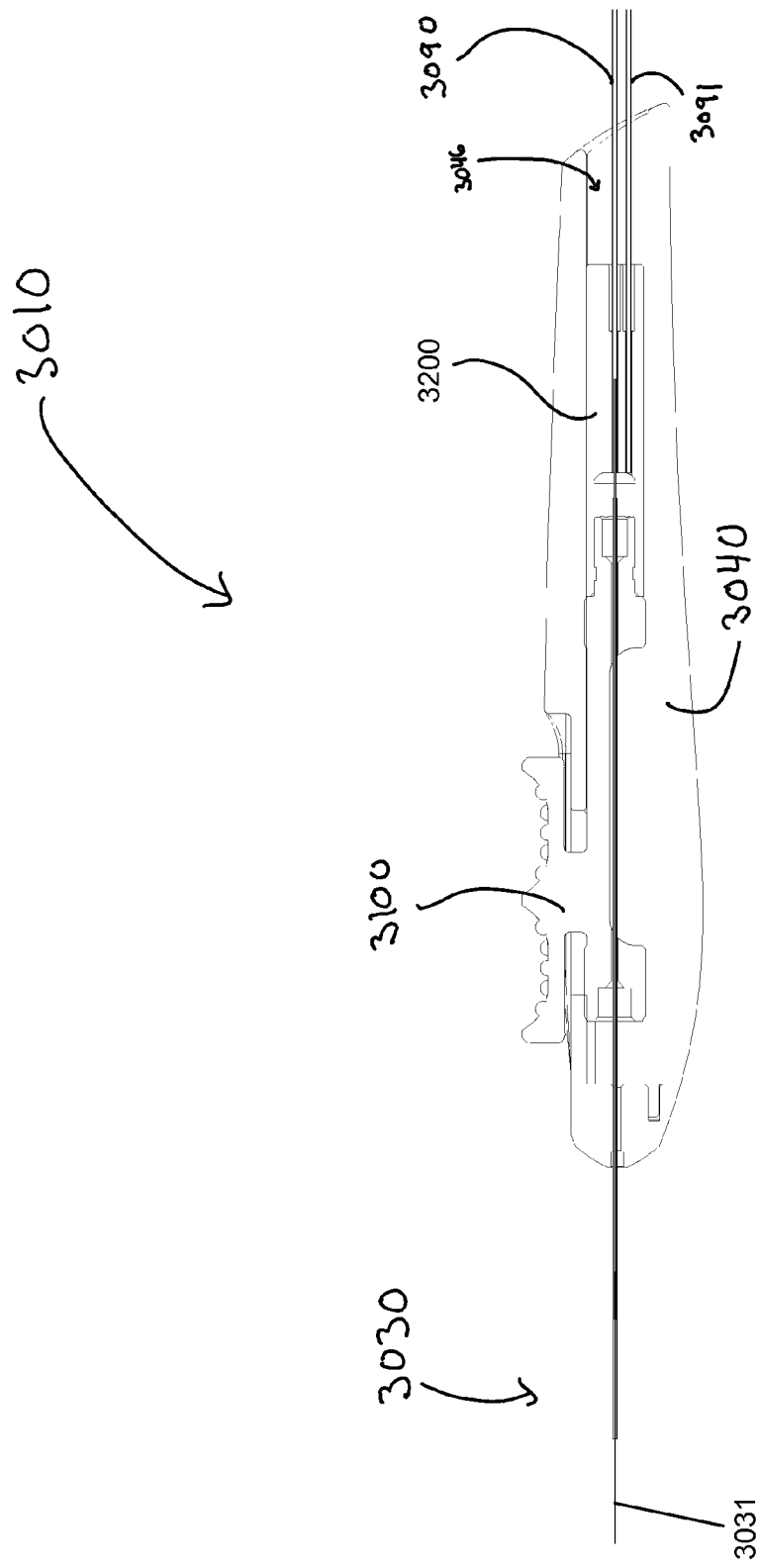
FIG. 16A depicts a side cross-sectional view of the instrument of FIG. 14 with the retinal penetrating element in a retracted position, and with an outer cannula omitted.
Figure 16B:
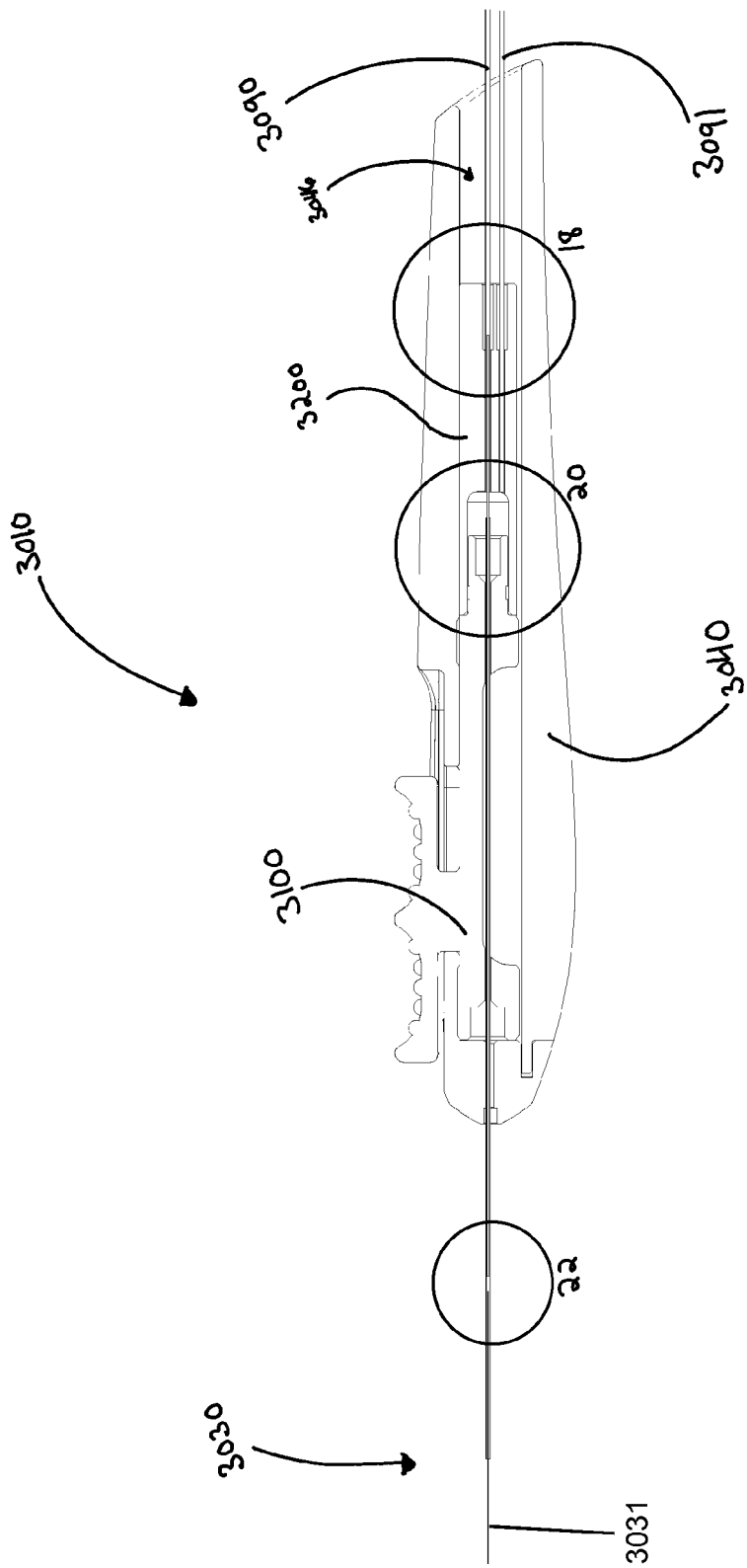
FIG. 16B depicts a side cross-sectional view of the instrument of FIG. 14 with the retinal penetrating element in an extended position, and with an outer cannula omitted.

As best seen in FIGS. 15A-16B, slider (3100) is slidably coupled with body (3040). Slider (3100) is capable of translating from a proximal position, as shown in FIGS. 15A and 16A, to a distal position, as shown in FIGS. 15B and 16B. Translation of slider (3100) translates inner cannula (3031) relative to body (3040) and relative to outer cannula (3020) (which is omitted from FIGS. 16A-16B). In some versions, slider (3100) is operable to slide inner cannula (3031) along a longitudinal distance of up to approximately 10 mm. Alternatively, any other suitable distances may be provided. Inner cannula (3031) is in fluid communication with both supply tubes (3090, 3091) as will be described in greater detail below.

Figure 17:
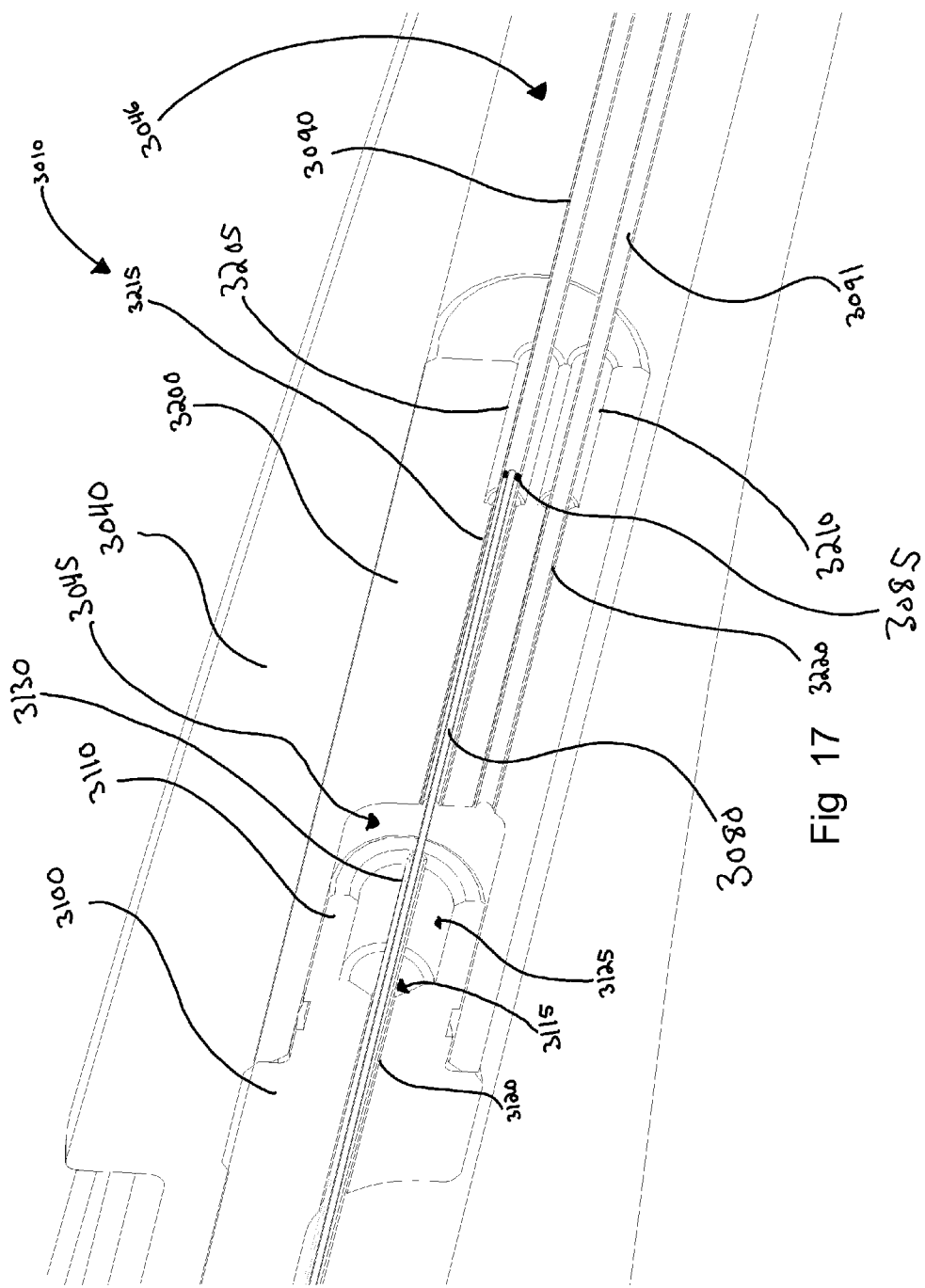
FIG. 17 depicts a perspective cross-sectional view of selected portions of the fluid delivery system of the instrument of FIG. 14.
Figure 19:
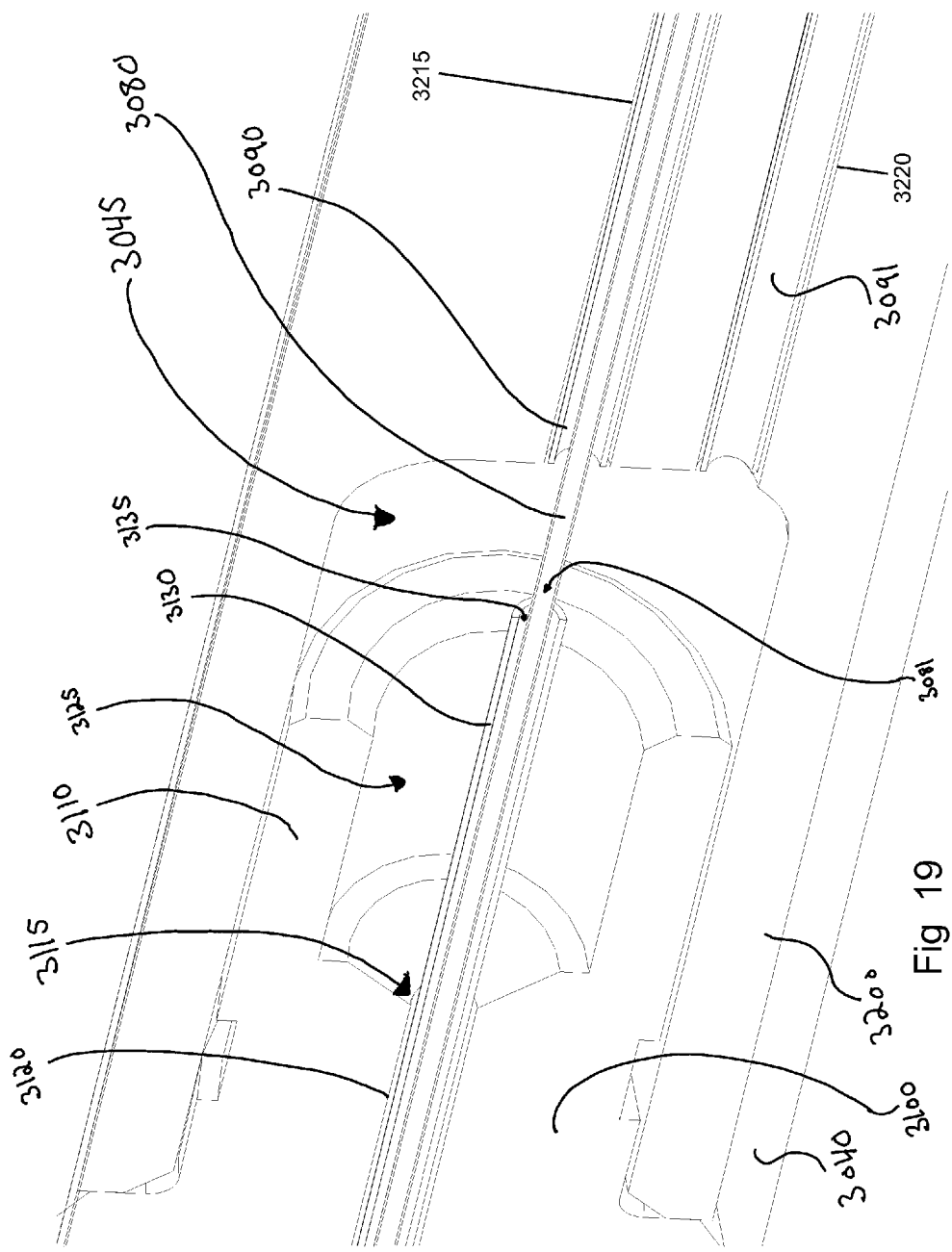
FIG. 19 depicts a perspective cross-sectional view of selected portions of the fluid delivery system of the instrument of FIG. 14.
Figure 20:
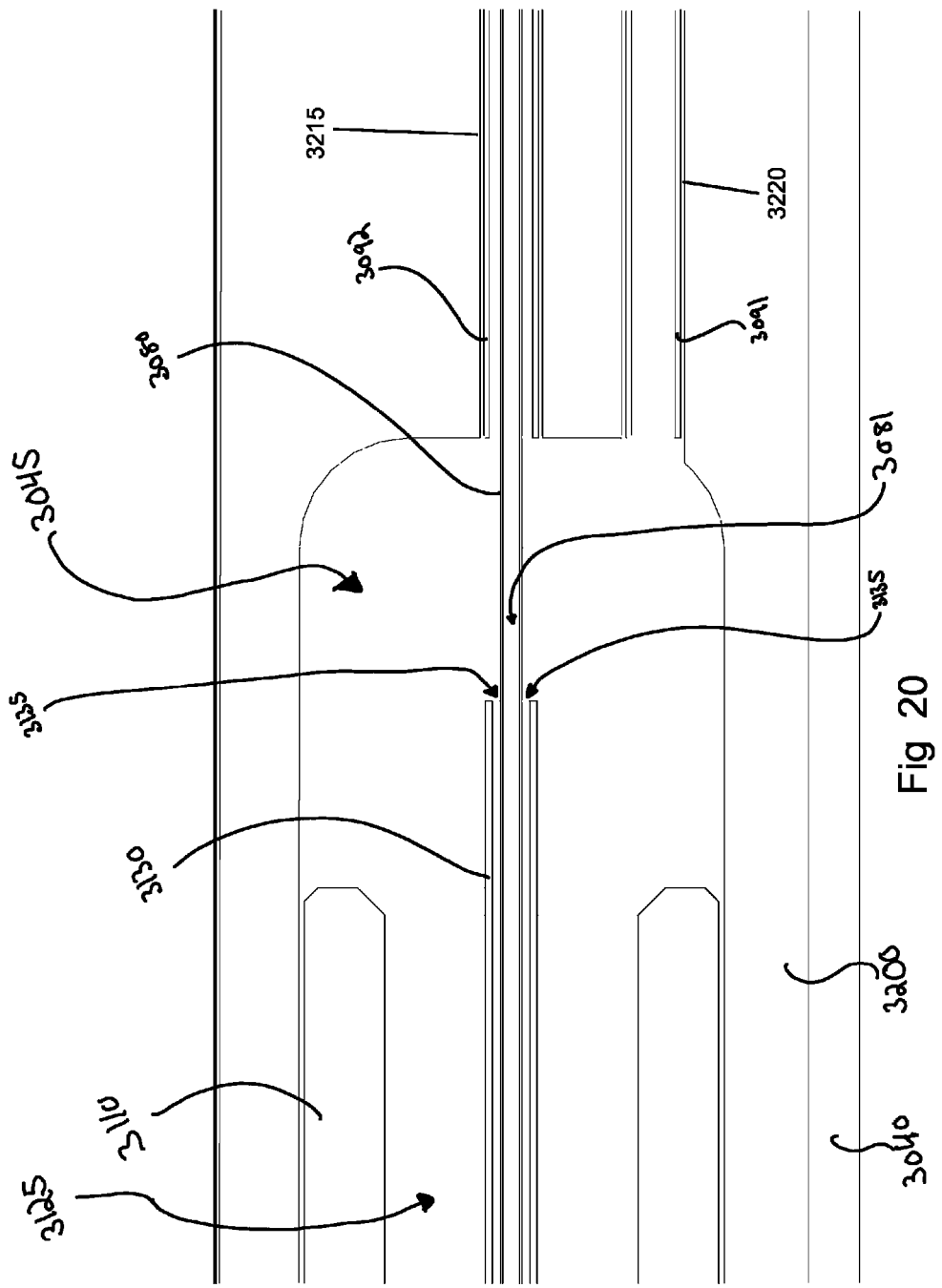
FIG. 20 depicts a side cross-sectional view of selected portions of the fluid delivery system of the instrument of FIG. 14.

As best seen in FIGS. 16A-16B, body (3040) partially houses slider (3100) and completely houses connector member (3200). As best seen in FIGS. 17 and 19-20, slider (3100) comprises a proximal annular end (3110), a fluid seal (3115), and a channel (3120) distal to fluid seal (3115). Proximal annular end (3110) defines a fluid chamber (3125). As also best seen in FIGS. 17 and 19-20, connector member (3200) comprises a fluid chamber (3045), tube passageways (3215, 3220), and tube entry passages (3215, 3210) at the proximal ends of respective tube passageways (3215, 3220).

As best seen in FIGS. 17-20, supply tubes (3090, 3091) enter proximal opening (3046) of body (3040), pass through tube passageways (3215, 3220) and tube entry passages (3215, 3210), and terminate at fluid chamber (3045) of connector member (3200). Tube entry passages (3205, 3210) have a larger inner diameter than tube passageways (3215, 3220) to facilitate insertion of supply tubes (3090, 3091) during assembly of instrument (3010). Tube passageways (3215, 3220) are dimensioned to provide an interference fit with supply tubes (3090, 3091) respectively, such that supply tubes (3090, 3091) are securely retained in tube passageways (3215, 3220). Of course, tube entry passages (3205, 3210), tube passageways (3215, 3220), and supply tubes (3090, 3091) may have any other suitable dimensional relationships. Additionally, supply tubes (3090, 3091) may be secured to connector member (3200) in any other suitable fashion.

Proximal annular end (3110) of slider (3100) is dimensioned to provide a fluid tight interference fit with the distal end of connector member (3200). Connector member (3200) thus travels longitudinally with slider (3100) relative to body (3040). In addition, proximal annular end (3110) of slider (3100) is dimensioned to leave a gap in fluid chamber (3045) of connector member (3200). Thus, fluid chamber (3125) of slider (3100) is in fluid communication with fluid chamber (3045) of connector member (3200). As noted above and as best seen in FIGS. 17 and 19-20, supply tube (3091) terminates at fluid chamber (3045), such that supply tube (3091) is in fluid communication with fluid chamber (3125).

Figure 18:
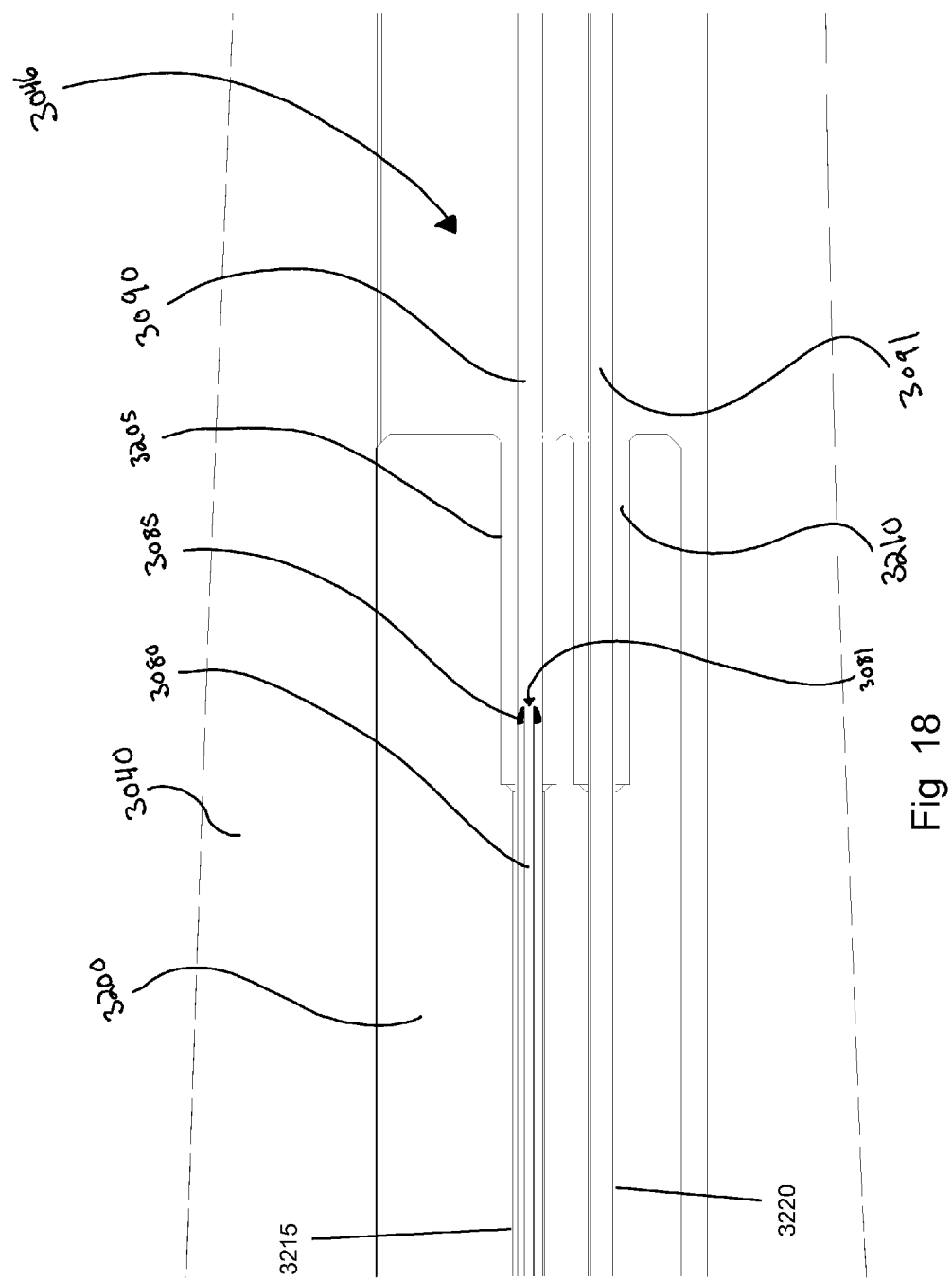
FIG. 18 depicts a side cross-sectional view of selected portions of the fluid delivery system of the instrument of FIG. 14.

As best seen in FIGS. 17-18, the proximal portion of a tube member (3080) is coaxially positioned within supply tube (3090). The proximal end (3085) of tube member (3080) contacts the inner sidewall of supply tube (3090) to provide a fixed, fluid tight seal. Thus, any fluid communicated to supply tube (3090) will be communicated through the inner lumen (3081) defined by tube member (3080). In the present example, tube member (3080) comprises a polyether block amide material such as PEBAX® (by Arkema of Colombes, France). However, it should be understood that any other suitable material(s) may be used (e.g., polyimide, etc.). Also in the present example, tube member (3080) has an inner diameter of approximately 0.0064 inches and an outer diameter of approximately 0.0079 inches. Again, though, any other suitable dimensions may be used.

As best seen in FIGS. 17 and 19-20, tube member (3080) extends past the distal end of supply tube (3090) and into fluid chamber (3045), where tube member (3080) is coaxially received in a sleeve (3130). Sleeve (3130) extends proximally from fluid seal (3115) in such a way that the proximal end of sleeve (3130) is positioned within fluid chamber (3045) and fluid chamber (3125). Sleeve (3130) is tightly disposed in channel (3120) of slider (3100) such that sleeve travels longitudinally with slider (3100) relative to body (3040). Of course, sleeve (3130) may be secured to slider (3100) in any suitable fashion. In addition, fluid seal (3115) prevents liquid from passing over the outer diameter of sleeve (3130) in channel (3120).

As best seen in FIGS. 19-20, tube member (3080) has an outer diameter that is sufficiently smaller than the inner diameter of sleeve (3130) such that a gap (3135) is defined between the outer diameter of tube member (3080) and the inner diameter of sleeve (3130). This gap (3135) is sized to provide fluid communication through sleeve (3130). For instance, when leading bleb (340) fluid is communicated through supply tube (3091) that leading bleb (340) fluid will enter gap (3135) via fluid chamber (3045) and will further travel through sleeve (3130).

It should be understood from the foregoing that supply tube (3091) is in fluid communication with gap (3135), yet not in fluid communication with lumen (3081). Using gap (3135) to communicate leading bleb (340) may have an advantage of saving cross-sectional area compared to running a second inner tube member (3080) within sleeve (3130). Those skilled in the arts will recognize that gap (3135) dimensions are dictated by the outer diameter of tube member (3080) subtracted from the inner diameter of sleeve (3130). Those skilled in the art will recognize that these dimensions can and should be adjusted to provide optimal flow based on the desired viscosity and shear resistance that the fluids can withstand.

Figure 21:
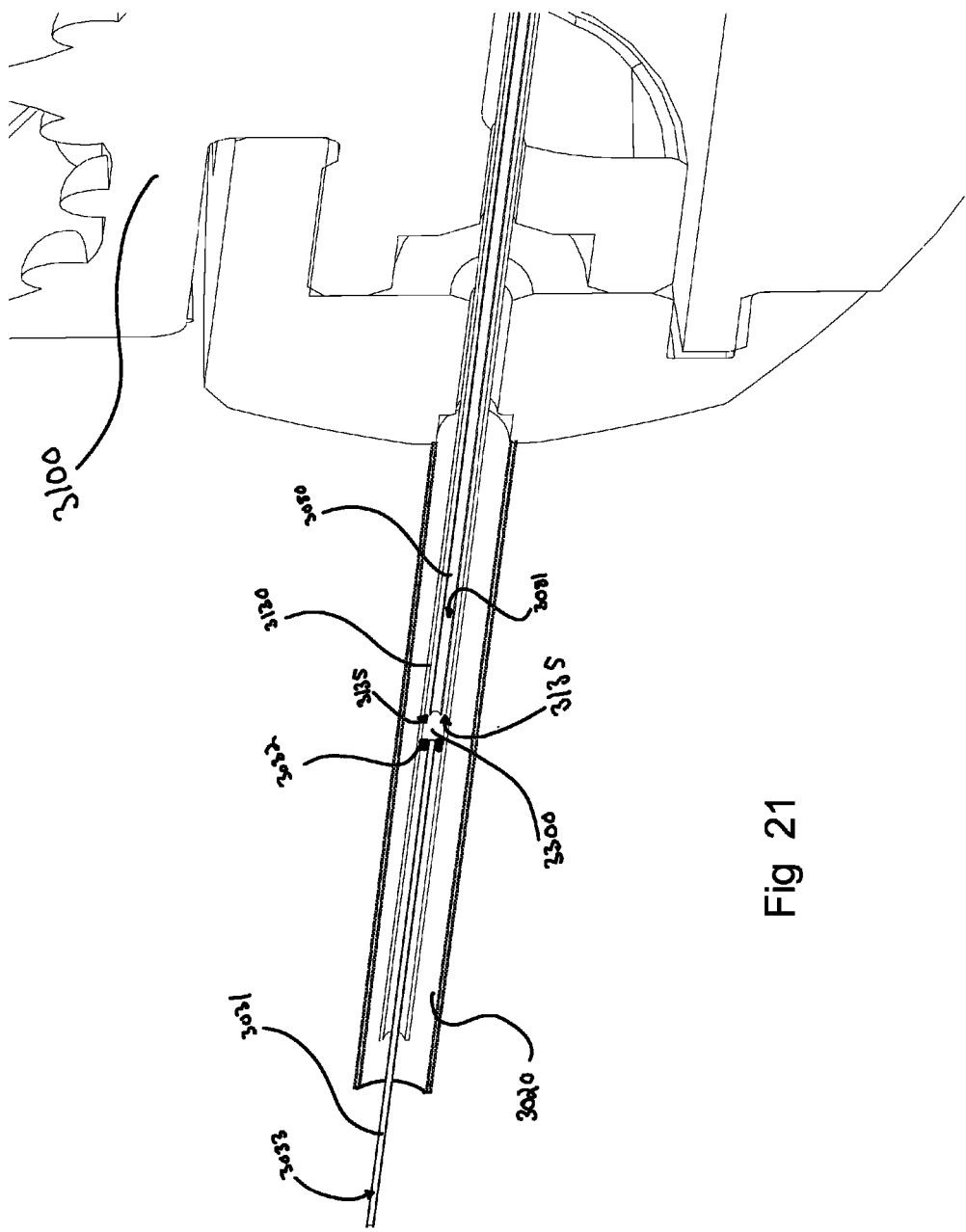
FIG. 21 depicts a perspective cross-sectional view of the distal end of the instrument of FIG. 14.

As best seen in FIG. 21, outer cannula (3020) is fixed to and extends distally from body (3040). Fixed outer cannula (3020) also houses distal ends of tube member (3080) and sleeve (3130) in such a manner that tube member (3080) and sleeve (3130) terminate within outer cannula (3020). Outer cannula (3020) also houses the proximal end (3032) of inner cannula (3031), which is secured to the inner diameter of sleeve (3130). Thus, when slider (3100) is actuated to slide relative to body (3040), sleeve (3130) is also actuated to slide relative to body (3040) due to the fact sleeve (3130) is fixed to slider (3100). In turn, inner cannula (3031) is actuated to slide relative to body (3040) due to the fact inner cannula (3031) is fixed to sleeve (3130). Therefore, inner cannula (3031) is actuated to slide relative to body (3040) by slider (3100).

In the present example, inner cannula (3031) is hollow with a dimension of 38 gauge (e.g., an inner diameter of approximately 0.004 inches and an outer diameter of approximately 0.005 inches). Alternatively, any other suitable dimensions may be used. Also in the present example, inner cannula (3031) is formed of polyimide material. This is because a thermoset of polyimide may be cast/molded in small accurate tube sizes and the polymer is relatively stiff compared to other polymers to give the tip of inner cannula (3031) some column strength as needed to penetrate the retina (308) and enter the subretinal space Inner cannula (3031) is adapted to deliver fluid such as leading bleb (340) and therapeutic agent (341) to the subretinal space as described in greater detail below.

Figure 22:
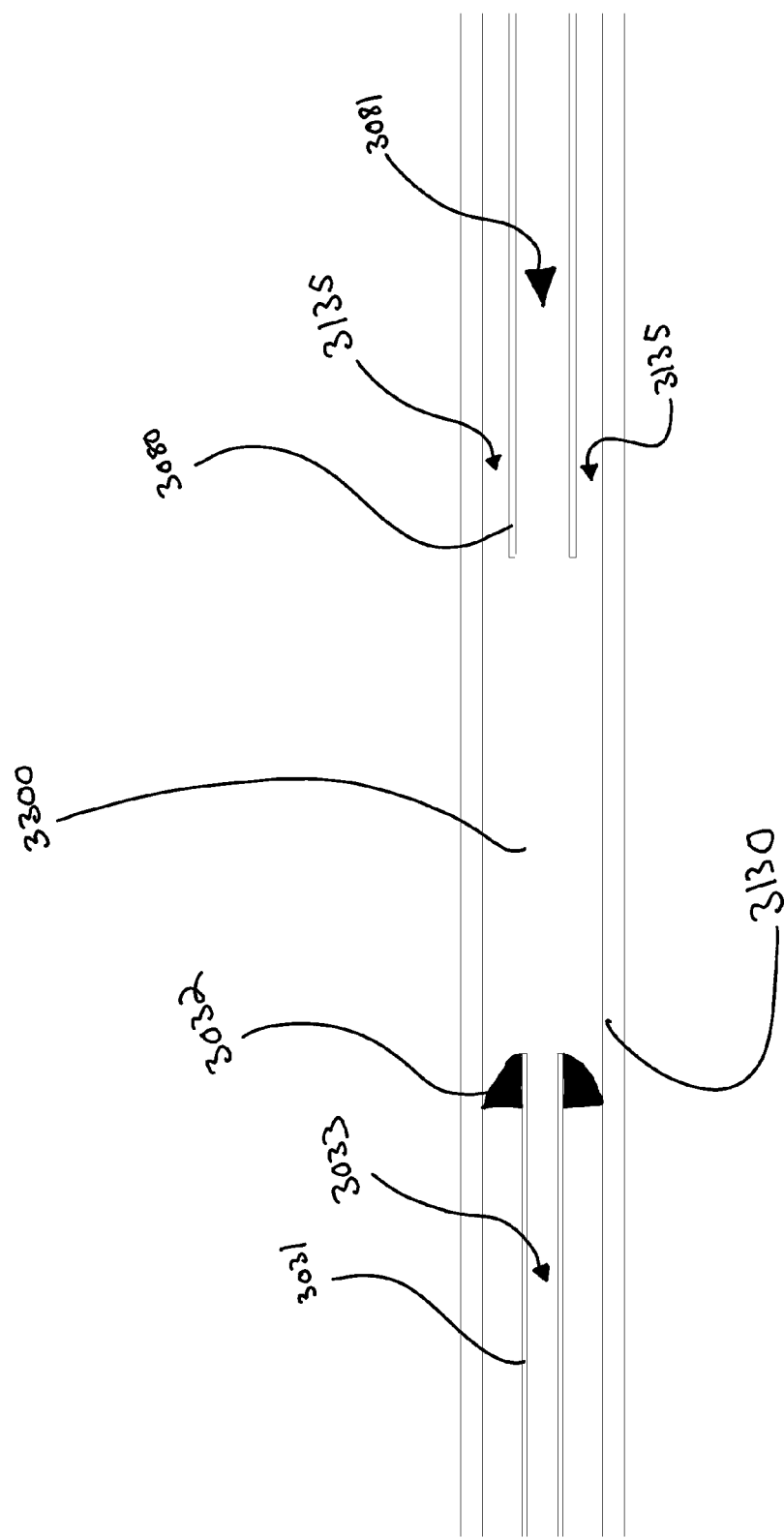
FIG. 22 depicts a side cross-sectional view of the distal end of the fluid delivery system of the instrument of FIG. 14.

As best seen in FIGS. 21-22, tube member (3080) distally within an intermediate region of sleeve (3130) in such a way that the open distal end of tube member (3080) is housed within sleeve (3130). In other words, lumen (3081) and gap (3135) meet at the distal end of tube member (3080) to partially define mutual fluid chamber (3300). Mutual fluid chamber (3300) is bound by both the portion of sleeve (3130) extending distally relative to tube member (3080) and the portion of sleeve (3130) extending proximally relative to the proximal end (3032) of inner cannula (3031). Mutual fluid chamber (3300) will fill with either fluid from gap (3135), fluid from lumen (3081), or fluid from both depending on which fluid source is pressurized.

The proximal end (3032) of inner cannula (3031) is fixed to sleeve (3130) in such a way (e.g., by an adhesive) as to provide a fluid seal against the inner diameter of sleeve (3130) Inner cannula (3031) defines a lumen (3033) that is in fluid communication with mutual fluid chamber (3300). In the present example, the distal end of inner cannula (3031) is flush cut, such that the distal edge of inner cannula extends along a plane that is perpendicular to the longitudinal axis of inner cannula (3031). In other words, the distal end of inner cannula (3031) is not sharp in the present example. Nevertheless, due to the small diameter of inner cannula (3031), the column strength of the material forming inner cannula (3031), and the fragility of the retina (308), the distal end of inner cannula (3031) is capable of penetrating the retina (308) as described below, despite the blunt configuration of the distal end of inner cannula (3031). In some other versions, the distal end of inner cannula (3031) is sharp or has some other configuration.

Inner cannula (3031) is thus capable of passing through the retina (308) to deliver fluid from either supply tube (3090, 3091) to the subretinal space. It should be understood that, by using sleeve (3130) as a fluid conduit for inner cannula (3031), and by having sleeve (3130) project distally relative to body (3040), the length of inner cannula (3031) may be minimized. Minimizing the length of inner cannula (3031) may enable inner cannula (3031) to effectively communicate leading bleb (340) fluid and therapeutic agent (341) through a lumen (3033) having a very small inner diameter (e.g., approximately 0.004 inches) with minimal pressure requirements and minimal shear effects. Minimizing the pressure and shear effects on fluid traveling through lumen (3033) may prevent sensitive bioactive components of therapeutic agent (341) from being damaged during transport through lumen (3033).

An exemplary method of using instrument (3010) in this fashion is described in greater detail below. It should also be understood that a variation of instrument (3010) may also be used in the procedure described above with reference to FIGS. 8A-10C. Other suitable ways in which instrument (3010) may be varied and used will be apparent to those of ordinary skill in the art in view of the teachings herein.

Figure 23:
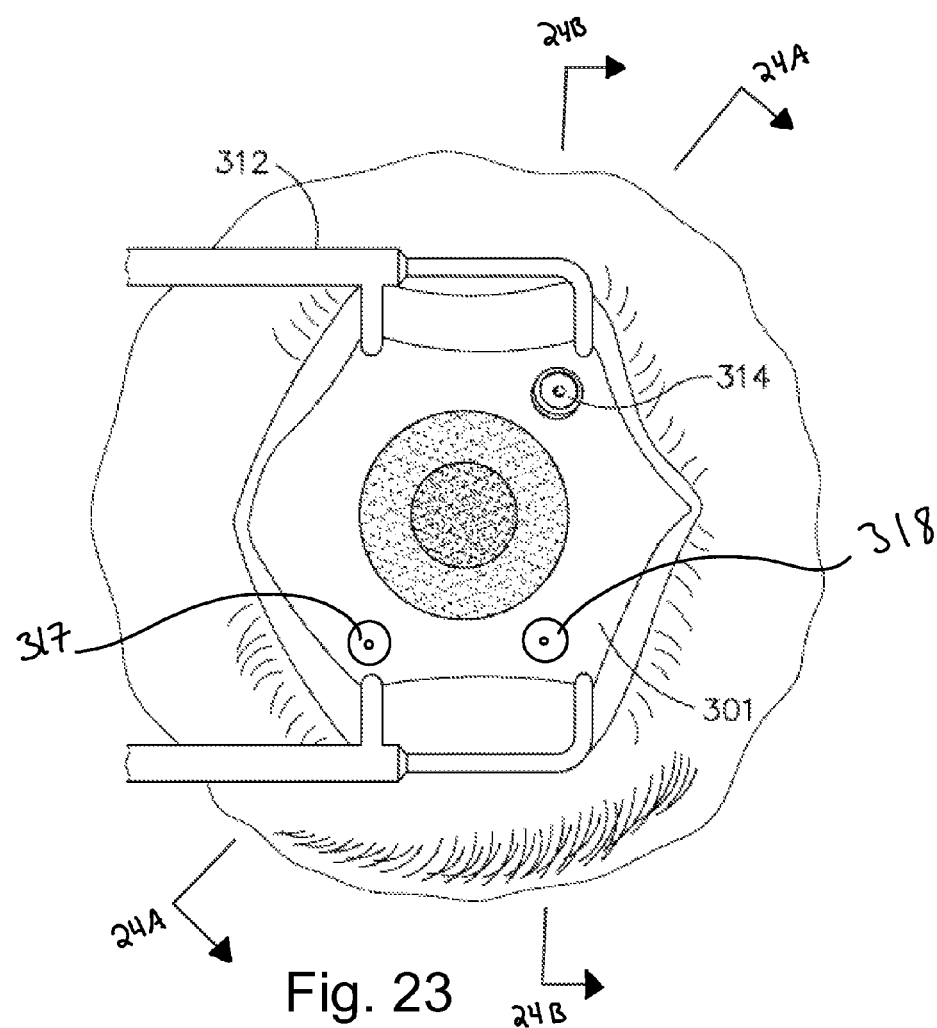
FIG. 23 depicts a top plan view of an eye of a patient, with surrounding structures of the eye immobilized and three ports installed.

VI. Exemplary Method for Delivery of Therapeutic Agent from Trans-Retinal Approach FIGS. 23-24J show a method of using instrument (3010) to provide for an ipsilaterial or transvitreal administration of therapeutic agent (341) to the subretinal space of a patient. While instrument (3010) is used in the depicted version of the method, it should be understood that instruments (10, 2010) may be modified to perform the method shown in FIGS. 23-34J and described below. It should also be understood that instruments (10, 2010) may be readily modified to include at least some of the above described fluid communication features of instrument (3010), even if instruments (10, 2010) are only to be used in a procedure for subretinal administration of a therapeutic agent from a suprachoroidal approach as described above with reference to FIGS. 8A-10C. For instance, needle (30, 2230) may receive leading bleb (340) and therapeutic agent (341) through the same kind of structures through which inner cannula (3031) receives leading bleb (340) and therapeutic agent (341). Other suitable ways in which the teachings herein may be interchanged and combined will be apparent to those of ordinary skill in the art.

As can be seen in FIG. 23, the procedure begins by an operator immobilizing tissue surrounding a patient's eye (301) (e.g., the eyelids) using speculum (312), and/or any other instrument suitable for immobilization. While immobilization is described herein with reference to tissue surrounding eye (301), it should be understood that eye (301) itself may remain free to move. Once the tissue surrounding eye (301) has been immobilized, an eye chandelier port (314) is inserted into eye (301) to provide intraocular illumination when the interior of eye (301) is viewed through the pupil. In the present example, eye chandelier port (314) is positioned in the inferior medial quadrant. Additionally, a vitrectomy port (317) is inserted into eye (301) to provide access to perform a standard three port pars plana core vitrectomy. In the present example, vitrectomy port (317) is positioned in the superior temporal quadrant. Also, third port (318) is inserted into eye (301) to provide access for device to administer therapeutic fluid (341) to the subretinal space of eye (301). In the present example, third port (318) is positioned in the superior medial quadrant. Various suitable forms that ports (314, 317, 318) may take will be apparent to those of ordinary skill in the art in view of the teachings herein.

Figure 24A:
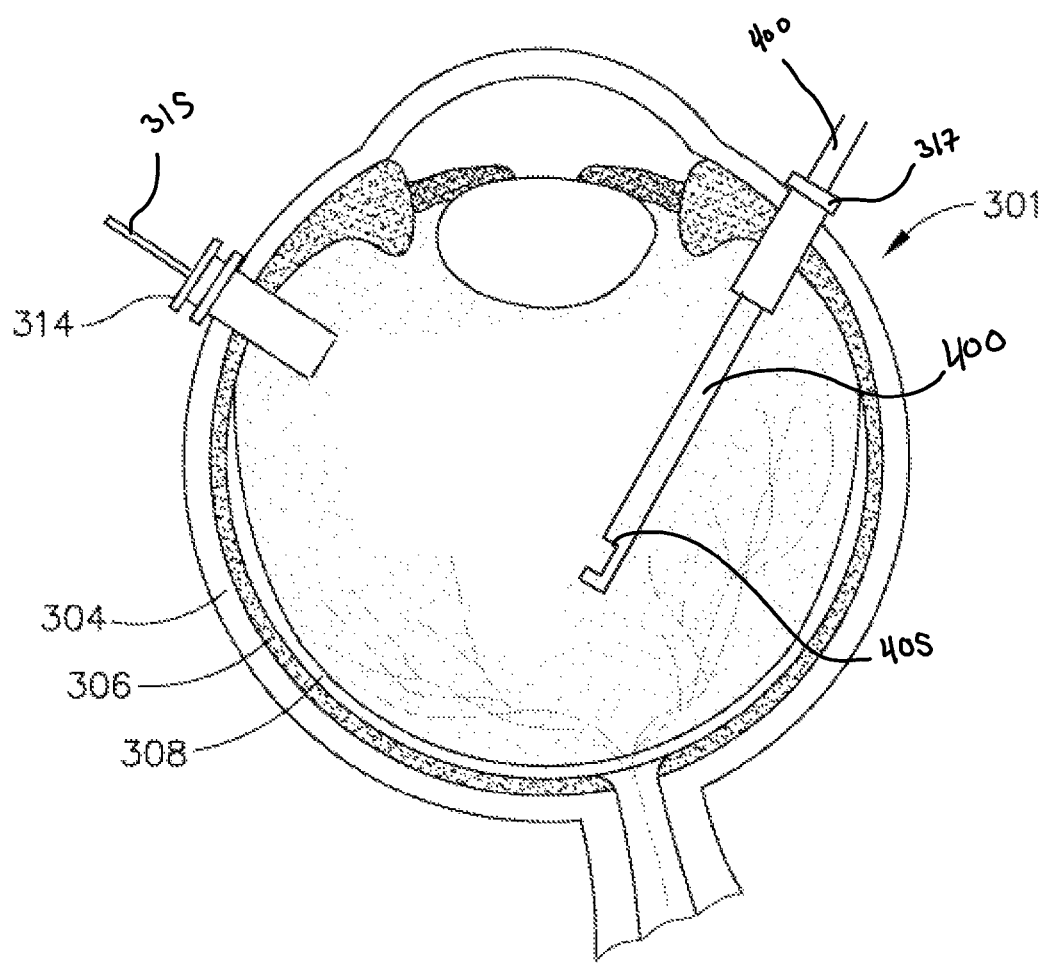
FIG. 24A depicts a cross-sectional view of the eye of FIG. 23, the cross-section taken along line 24A-24A of FIG. 23.

As can be seen in FIG. 24A, eye chandelier port (314) is positioned to direct light onto the interior of eye (314) to illuminate at least a portion of the retina (308) (e.g., including at least a portion of the macula). As will be understood, such illumination corresponds to an area of eye (301) that is being targeted for delivery of therapeutic agent (341). An optical fiber (315) has been inserted into port (314) to provide the illumination. A microscope may optionally be utilized to visually inspect the eye to confirm proper positioning of eye chandelier port (314) relative to the target site. Although FIG. 24A shows a particular positioning of eye chandelier port (314), it should be understood that eye chandelier port (314) may have any other positioning as will be apparent to those of ordinary skill in the art in view of the teachings herein. Additionally, a conventional vitrectomy instrument (400) is inserted through vitrectomy port (317) to perform a conventional three port pars plana core vitrectomy procedure. After completion of a conventional three port pars plana core vitrectomy procedure, vitrectomy instrument (400) is removed.

After or before the conventional three port pars plana core vitrectomy procedure is completed, instrument (3010) may be prepared for subretinal administration of therapeutic fluid (341). By way of example only, the preparation of instrument (3010) may include coupling luer fitting (3095) with a source of therapeutic fluid (341) and coupling luer fitting (3096) with a source leading bleb (340) fluid. Next, the fluid sources may be pressurized to prime the fluid communicating components leading up to and including lumen (3033) of inner cannula (3031) until a drop of leading bleb fluid (340) or therapeutic fluid (341) exits the distal end of inner cannula (3031). In some instances, the source of therapeutic fluid (341) is pressurized first, followed by pressurization of the source of leading bleb (340) fluid. In some other instances, the source of leading bleb (340) fluid is pressurized first, followed by pressurization of the source of therapeutic fluid (341). In some other instances, both fluid sources are pressurized at substantially the same time. It should also be understood that, in some instances, an air gap may be provided between leading bleb (340) and therapeutic fluid (341) to prevent therapeutic fluid (341) from mixing with leading bleb (340). Various suitable ways in which instrument (3010) may be primed with leading bleb (340) fluid, therapeutic fluid (341), and/or an intentional air gap will be apparent to those of ordinary skill in the art in view of the teachings herein.

Figure 24B:
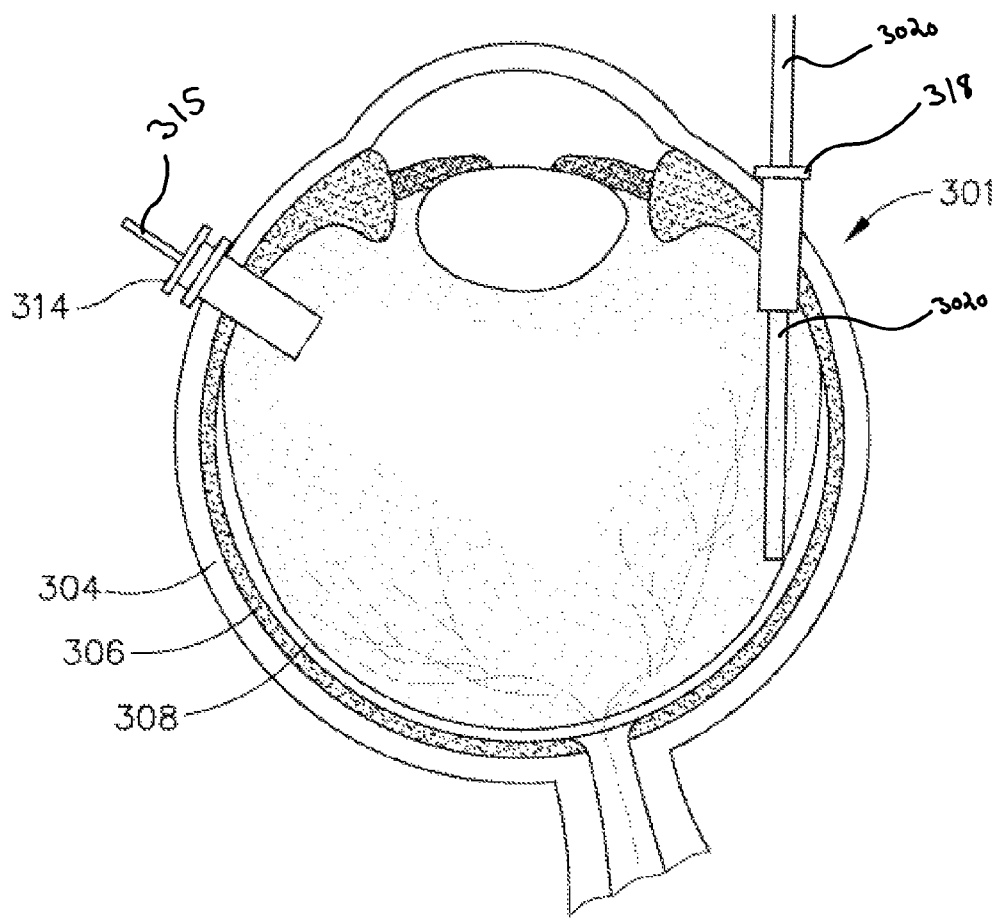
FIG. 24B depicts a cross-sectional view of the eye of FIG. 23, the cross-section taken along line 24B-24B of FIG. 23.

After instrument (3010) has been primed, outer cannula (3020) is inserted into third port (318) as shown in FIG. 24B. When outer cannula (3020) is inserted into third port (318), slider (3100) is in a proximal position as shown in FIGS. 15A and 16A, thereby ensuring that the distal end of inner cannula (3031) is positioned within the interior of outer cannula (3020). Outer cannula (3020) is inserted to the point where the distal end of outer cannula (3020) is positioned adjacent to the interior of retina (308).

Figure 24C:
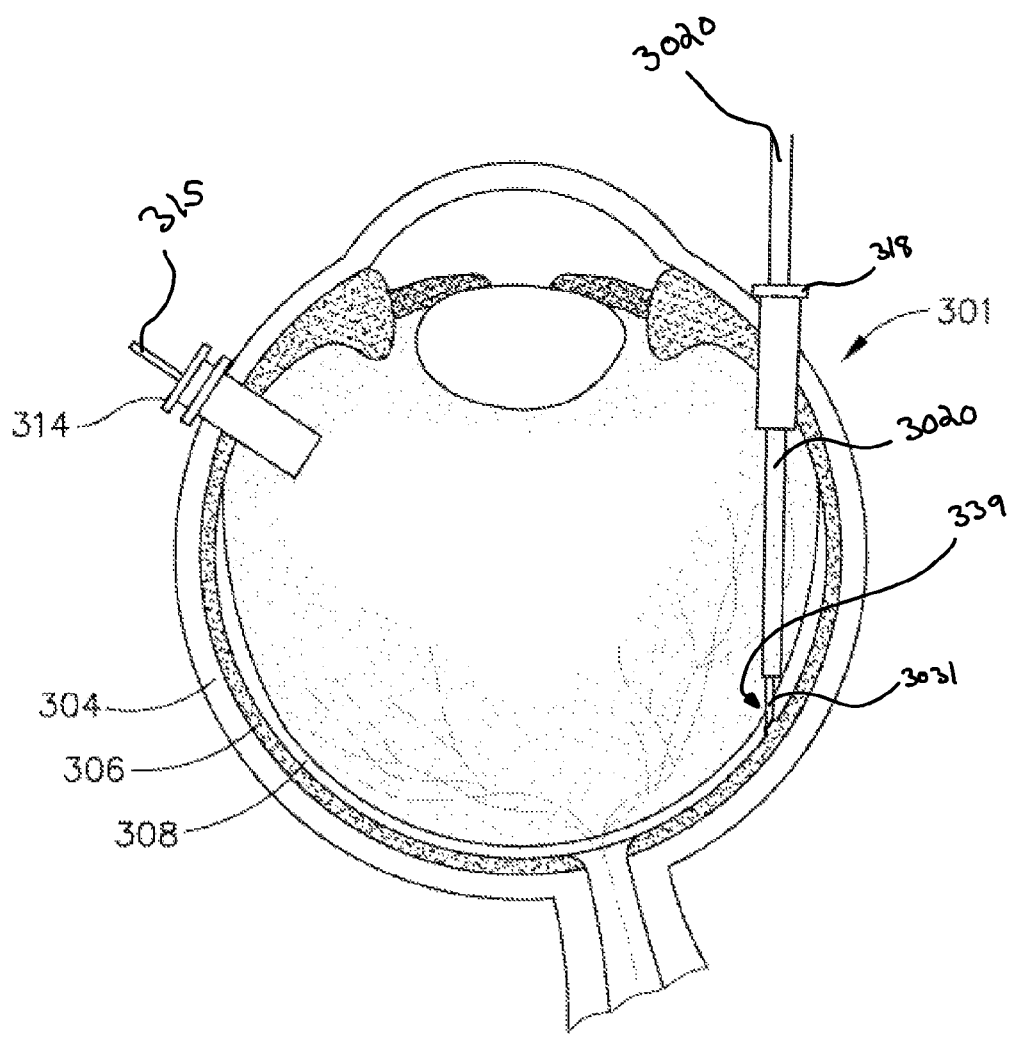
FIG. 24C depicts a cross-sectional view of the eye of FIG. 23, the cross-section taken along line 24B-24B of FIG. 23.

Once the distal end of outer cannula (3020) is positioned adjacent to interior of retina (308), slider (3100) is slid distally such that the distal end of inner cannula (3031) is exposed from the distal end of fixed outer cannula (3020) Inner cannula (3031) thus pierces the retina (308) to define a subretinal entry point (339) as shown in FIG. 24C.

Figure 24D:
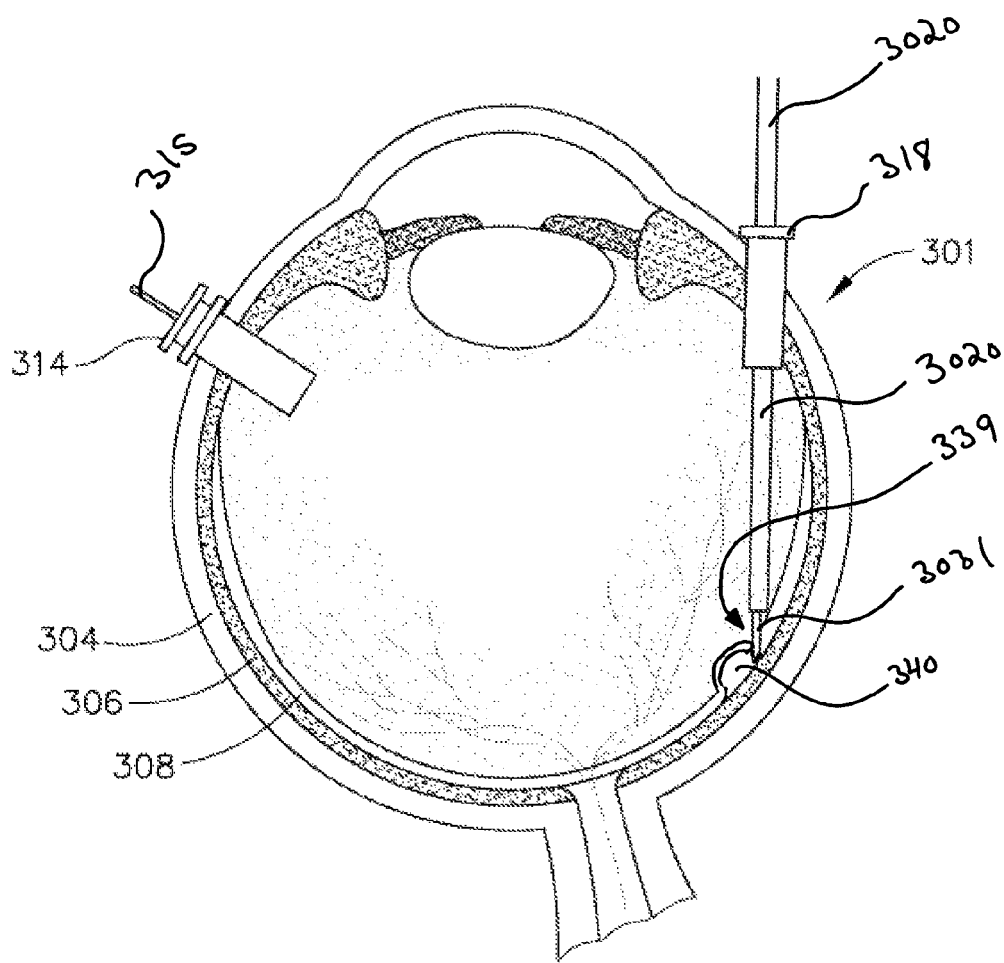
FIG. 24D depicts a cross-sectional view of the eye of FIG. 23, the cross-section taken along line 24B-24B of FIG. 23.

Once the distal end of inner cannula (3031) is positioned at a first location in the subretinal space via the subretinal entry point (339), the fluid source of leading bleb (430) fluid is pressurized. This pressurization drives the fluid through lumen (3033) of inner cannula (3031) to form leading bleb (340) within the subretinal space, between the retina (308) and the choroid (306), as shown in FIG. 24D.

Figure 24E:
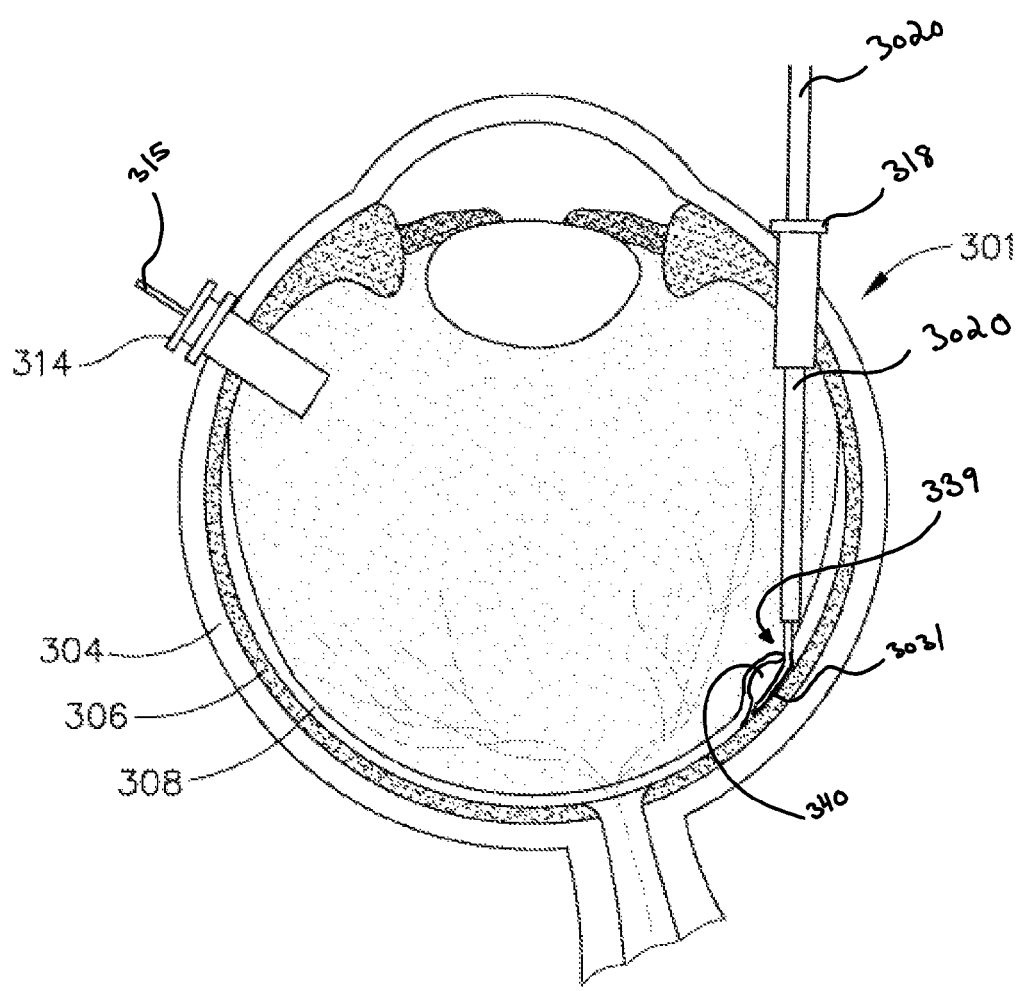
FIG. 24E depicts a cross-sectional view of the eye of FIG. 23, the cross-section taken along line 24B-24B of FIG. 23.
Figure 24F:
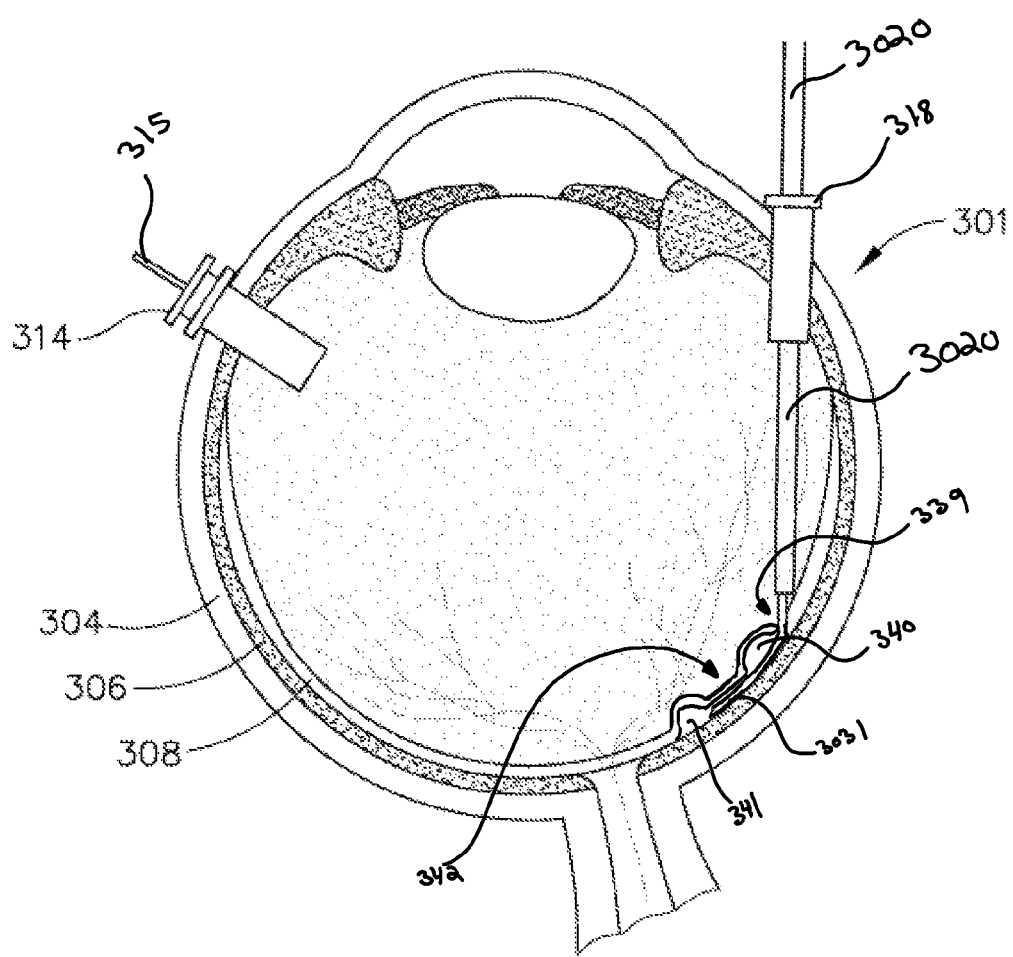
FIG. 24F depicts a cross-sectional view of the eye of FIG. 23, the cross-section taken along line 24B-24B of FIG. 23.

Once leading bleb (340) is formed at the first location in the subretinal space, inner cannula (3031) is advanced further distally via actuation of slider (3100) so that inner cannula (3031) is advanced in an inferior direction along the coronal plane and in a posterior direction along the sagittal plane as shown in FIGS. 24E-24F. In particular, inner cannula (3031) first travels between leading bleb (340) and the choroid (306) (FIG. 24E) and then past leading bleb (340) into the space between the retina (308) and the choroid (306) (FIG. 24F). This advancement of inner cannula (3031) thus defines a pathway (342) between the retina (308) and the choroid (306).

Once inner cannula (3031) reaches a second location in the subretinal space at the end of pathway (342), therapeutic agent (341) is injected in the subretinal area by pressurizing the fluid source of therapeutic agent (341) to drive therapeutic agent (341) distally out through lumen (3033) of inner cannula (3031) as shown in FIG. 24F.

Figure 24G:
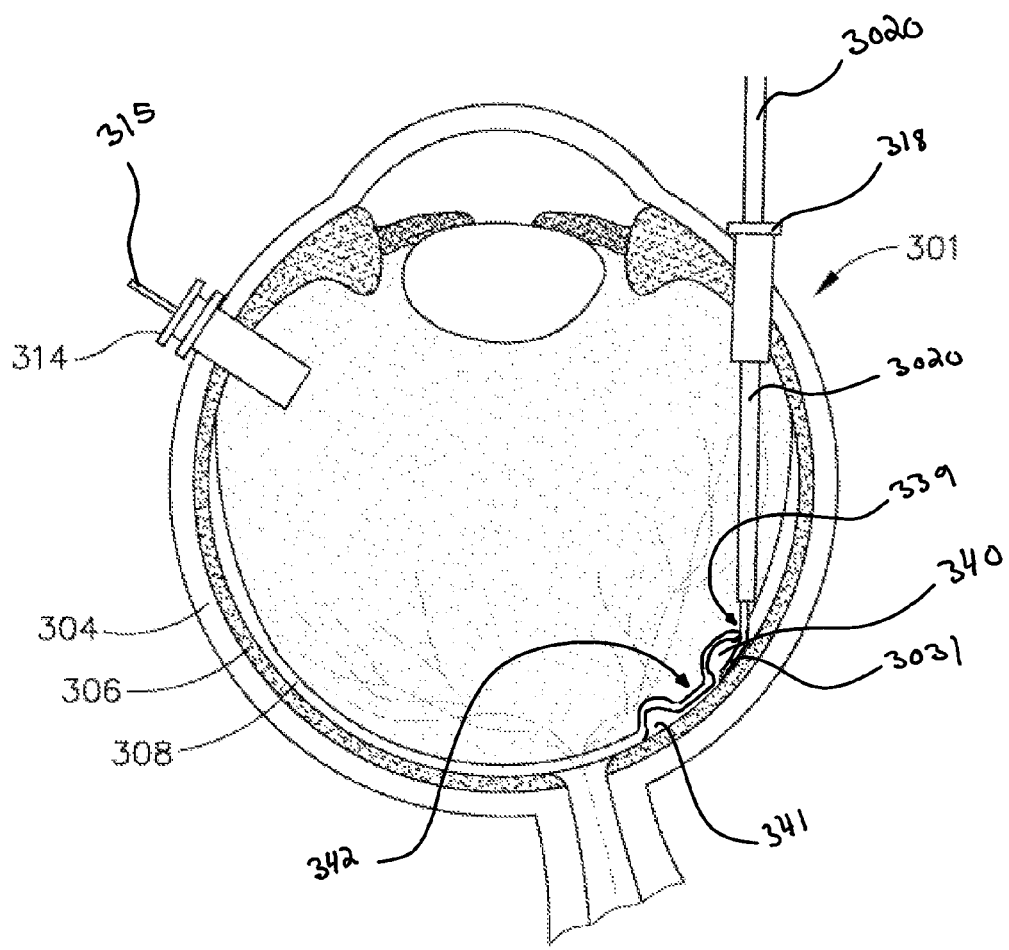
FIG. 24G depicts a cross-sectional view of the eye of FIG. 23, the cross-section taken along line 24B-24B of FIG. 23.

Once the proper amount of therapeutic fluid (341) has been delivered to the second location, slider (3100) is retracted proximally, thereby retracting inner cannula (3031) back to the first location as shown in FIG. 24G. While inner cannula (3031) is being retracted from pathway (342), the leading bleb (340) fluid may again be pressurized to release leading bleb (340) fluid within pathway (342) to help seal in therapeutic fluid (341) at the second location.

Figure 24H:
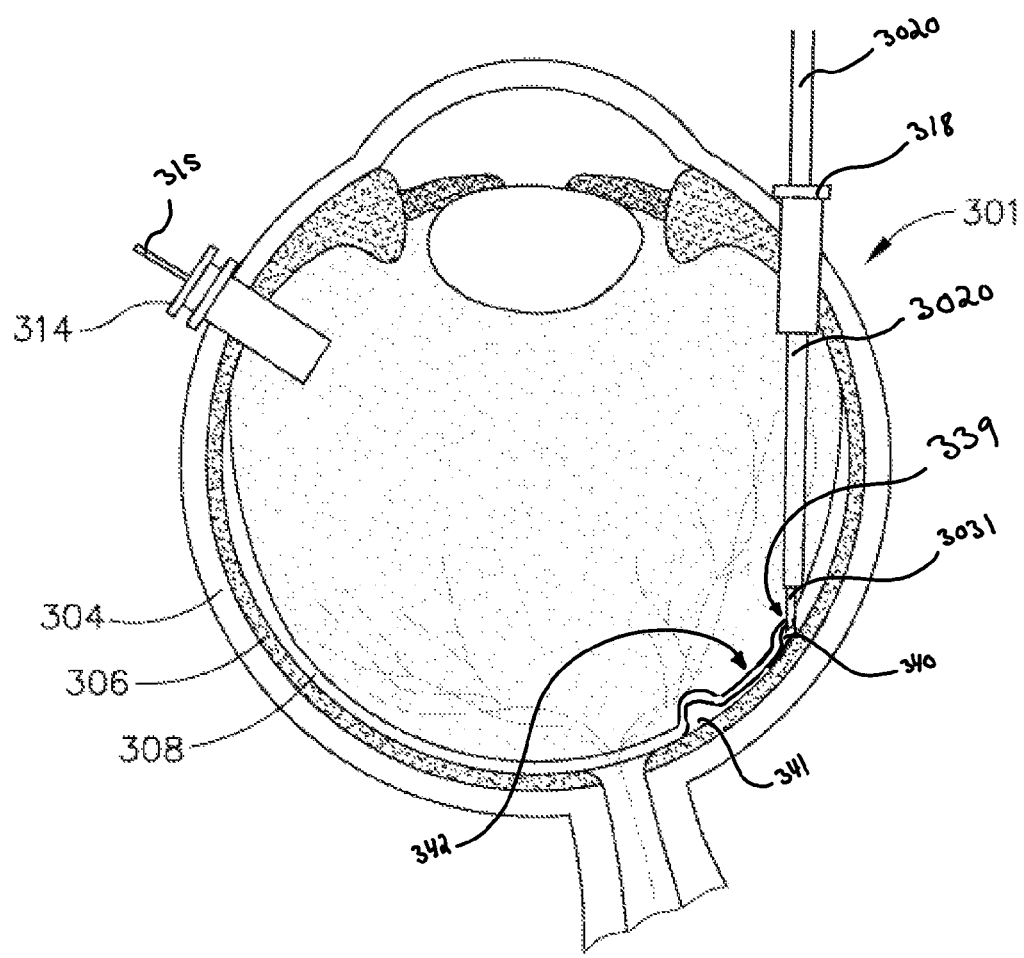
FIG. 24H depicts a cross-sectional view of the eye of FIG. 23, the cross-section taken along line 24B-24B of FIG. 23.

Once inner cannula (3031) has been retracted from pathway (342) as shown in FIG. 24G, negative pressure may be induced through either supply tube (3090, 3091) within inner cannula (3031) to aspirate leading bleb (340) as shown in FIG. 24H. Optionally, negative pressure may be induced to aspirate leading bleb (340) through other known means in the art, such as with a separate flextip inserter (MedOne). The separate flextip inserter or other conventional instrument may be inserted after removing instrument (3010) from the eye (301). In addition to or in lieu of aspirating leading bleb (340), air or other fluid may be used to effectively tamponade the bleb (340) in the subretinal space.

Figure 24I:
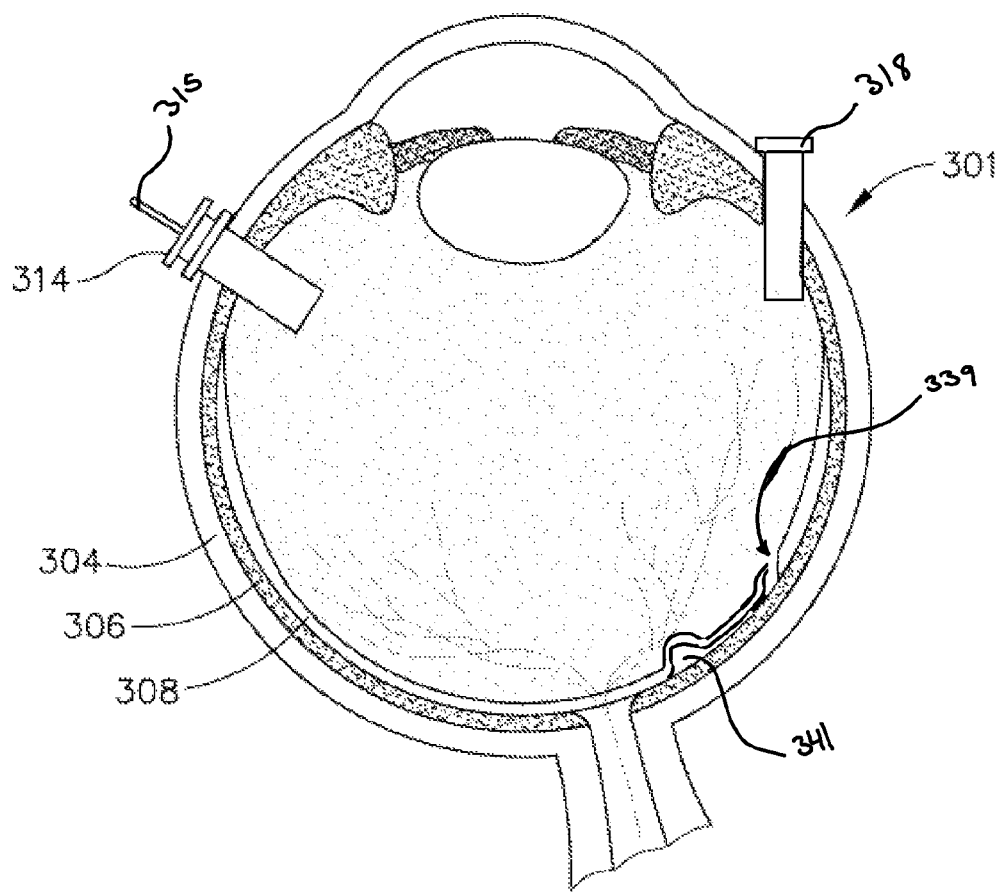
FIG. 24I depicts a cross-sectional view of the eye of FIG. 23, the cross-section taken along line 24B-24B of FIG. 23.
Figure 24J:
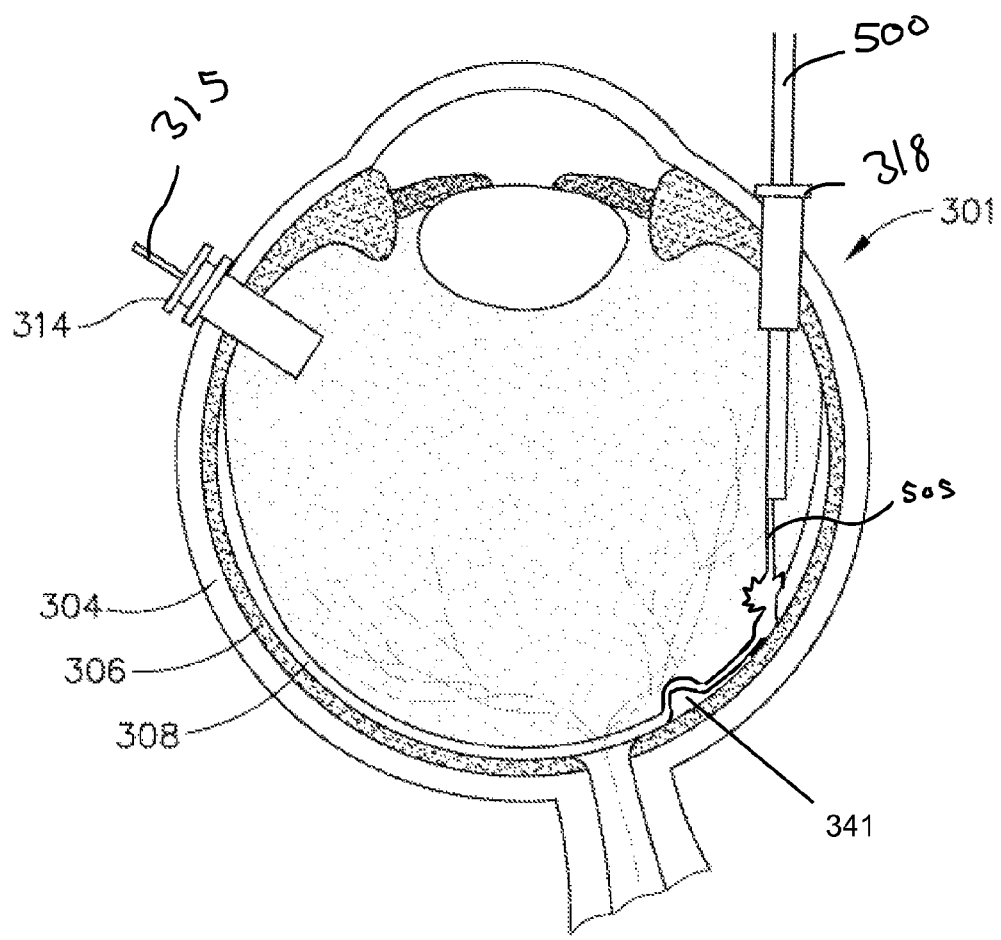
FIG. 24J depicts a cross-sectional view of the eye of FIG. 23, the cross-section taken along line 24B-24B of FIG. 23.

After leading bleb (340) has been aspirated or tamponaded, instrument (3010) is removed from third port (318) as shown in FIG. 24I. Thereafter, as shown in FIG. 24J, a laser retinopexy tool (500) is then inserted into third port (318) and is used to seal the subretinal entry point (339). Alternatively, any other suitable instruments or techniques may be used to seal the subretinal entry point (339).

It should be understood from the foregoing that instrument (3010) may be used to deliver two different kinds of fluids (e.g., leading bleb (340) fluid and therapeutic agent (341)) to the subretinal space without having to withdraw inner cannula (3031) from the subretinal space between the act of delivering the first fluid (e.g., leading bleb (340) fluid) and the second fluid (e.g., therapeutic agent (341)).

VII. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

An apparatus, comprising: (a) a first fluid conduit; (b) a second fluid conduit; (c) a connector member, wherein the connector member comprises: (i) a first passageway, wherein a portion of the first fluid conduit is positioned in the first passageway, and (ii) a second passageway, wherein a portion of the second conduit is positioned in the second passageway; (d) a first tubular member, wherein the first tubular member defines a first tubular member lumen; (e) a second tubular member, wherein at least a portion of the second tubular member is positioned within the first tubular member lumen, wherein the second tubular member defines a second tubular member lumen; and (f) an inner cannula, wherein a proximal portion of the inner cannula is fixedly secured within the first tubular member lumen, wherein the inner cannula defines an inner cannula lumen, wherein the inner cannula lumen is in fluid communication with the first and second fluid conduits via the first tubular member lumen and the second tubular member lumen.

Example 2

The apparatus of Example 1, further comprising a body, wherein the first and second fluid conduits extend proximally from the body, wherein the inner cannula extends distally relative to the body.

Example 3

The apparatus of Example 2, wherein the inner cannula is operable to translate longitudinally relative to the body Example 4

The apparatus of Example 3, wherein the first tubular member and the second tubular member are fixedly secured relative to the inner cannula such that the first tubular member and the second tubular member are operable to translate with the inner cannula relative to the body.

Example 5

The apparatus of Example 3 or Example 4, further comprising a slider coupled with the inner cannula, wherein the slider is slidable relative to the body to thereby translate the inner cannula longitudinally relative to the body.

Example 6

The apparatus of any one of Examples 2 through 5, further comprising an outer cannula, wherein the outer cannula is fixedly secured to the body, wherein the outer cannula extends distally from the body, wherein a portion of the outer cannula is positioned about a portion of the first tubular member.

Example 7

The apparatus of any of the preceding Examples, wherein a proximal portion of the second tubular member is positioned within a distal portion of the first fluid conduit such that the second tubular member lumen is in fluid communication with the first fluid conduit.

Example 8

The apparatus of Example 7, wherein the proximal portion of the second tubular member is fixedly secured to the first fluid conduit.

Example 9

The apparatus of Example 8, wherein a distal portion of the second tubular member terminates in an intermediate region of the first tubular member.

Example 10

The apparatus of any of the preceding Examples, wherein the second tubular member and the first tubular member are sized to define a gap between an outer diameter of the second tubular member and an inner diameter of the first tubular member, wherein the gap is in fluid communication with the second fluid conduit.

Example 11

The apparatus of Example 10, wherein a distal portion of the second tubular member terminates in an intermediate region of the first tubular member such that the first tubular member lumen at the intermediate region is configured to receive both of: (i) fluid from the first fluid conduit via the second tubular member lumen, and (ii) fluid from the second fluid conduit via the gap.

Example 12

The apparatus of any of the preceding Examples, wherein the second tubular member has a distal end positioned in an intermediate region of the first tubular member, wherein the inner cannula has a proximal end positioned in the intermediate region of the first tubular member, wherein the proximal end of the inner cannula is spaced distally from the distal end of the second tubular member.

Example 13

The apparatus of any of the preceding Examples, wherein the first tubular member, the second tubular member, and the inner cannula are all coaxially aligned with each other.

Example 14

The apparatus of any of the preceding Examples, wherein the inner cannula is flexible.

Example 15

The apparatus of any of the preceding Examples, wherein the inner cannula comprises polyether block amide or polyimide.

Example 16

An apparatus, comprising: (a) a first fluid conduit extending along a first axis; (b) a second fluid conduit extending along a second axis, wherein the second axis is offset from the first axis; (c) a first elongate member extending along the first axis, wherein the first fluid elongate member has a distal end, a proximal end, and an outer surface, wherein the first elongate member defines a first lumen, wherein the proximal end of the first elongate member is positioned in the first fluid conduit such that the first lumen is in fluid communication with the first fluid conduit; (d) a second elongate member extending along the first axis, wherein the second elongate member defines second lumen bounded by an inner surface, wherein the distal end of the first elongate member is positioned within the second lumen, wherein the outer surface of the first elongate member and the inner surface of the second elongate member together define a gap in fluid communication with the second fluid conduit; and (e) a third elongate member extending along the first axis, wherein the third elongate member has a proximal end positioned within the second elongate member, wherein the third elongate member defines a third lumen, wherein the proximal end of the third elongate member is positioned in the second lumen at a location distal to the distal end of the second elongate member, wherein the third lumen is in fluid communication with the first and second fluid conduits via the first lumen and via the gap, respectively.

Example 17

A method of delivering a therapeutic agent in an eye of a patient, wherein the eye has a vitreous body, a retina, a subretinal region, the method comprising the steps of: (a) inserting a port in the eye; (b) inserting a portion of an instrument through the port and into the vitreous body of the eye; (c) advancing an inner cannula member of the instrument through the retina of the eye to position a distal tip of the inner cannula member at a first location in the subretinal region of the eye; (d) communicating a first fluid to the first location in the subretinal region of the eye via the inner cannula member; (e) advancing the inner cannula member further distally to position the distal tip at a second location in the subretinal region of the eye; and (f) communicating a second fluid to the second location in the subretinal region of the eye via the inner cannula member; wherein the act of communicating the first fluid to the first location in the subretinal region of the eye and the act of communicating the second fluid to the second location in the subretinal region of the eye are performed without removing the inner cannula from the subretinal region between the act of communicating the first fluid to the first location in the subretinal region of the eye and the act of communicating the second fluid to the second location in the subretinal region.

Example 18

The method of Example 17, wherein the first fluid comprises a biologically inert bleb fluid.

Example 19

The method of Example 18, wherein the second fluid comprises a biologically active therapeutic agent.

Example 20

The method of Example 17, 18, or 19, further comprising aspirating at least a portion of the first fluid from the first location in the subretinal region after communicating the second fluid to the second location in the subretinal region.

VIII. Miscellaneous

It should be understood that any of the versions of the instruments described herein may include various other features in addition to or in lieu of those described above. By way of example only, any of the devices herein may also include one or more of the various features disclosed in any of the various references that are incorporated by reference herein.

It should be understood that any one or more of the teachings, expressions, embodiments, examples, etc.

described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by an operator immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An apparatus, comprising:
   (a) a first fluid conduit;
   (b) a second fluid conduit;
   (c) a connector member, wherein the connector member comprises:
       (i) a first passageway, wherein a portion of the first fluid conduit is positioned in the first passageway, and
       (ii) a second passageway, wherein a portion of the second conduit is positioned in the second passageway;
   (d) a first tubular member, wherein the first tubular member defines a first tubular member lumen;
   (e) a second tubular member, wherein at least a portion of the second tubular member is positioned within the first tubular member lumen, wherein the second tubular member defines a second tubular member lumen;
   (f) an inner cannula, wherein a proximal portion of the inner cannula is fixedly secured within the first tubular member lumen, wherein the inner cannula defines an inner cannula lumen, wherein the inner cannula lumen is in fluid communication with the first and second fluid conduits via the first tubular member lumen and the second tubular member lumen; and
   (g) a body, wherein the first and second fluid conduits extend proximally from the body, wherein the inner cannula extends distally relative to the body, wherein the first tubular member is fixedly secured relative to the inner cannula such that the first tubular member and the inner cannula are operable to translate together relative to the body.

2. The apparatus of claim 1, wherein second tubular member is fixedly secured relative to the inner cannula such that the the second tubular member is operable to translate with the inner cannula and the first tubular member relative to the body.

3. The apparatus of claim 1, further comprising a slider coupled with the inner cannula, wherein the slider is slidable relative to the body to thereby translate the inner cannula longitudinally relative to the body.

4. The apparatus of claim 1, further comprising an outer cannula, wherein the outer cannula is fixedly secured to the body, wherein the outer cannula extends distally from the body, wherein a portion of the outer cannula is positioned about a portion of the first tubular member.

5. The apparatus of claim 1, wherein a proximal portion of the second tubular member is positioned within a distal portion of the first fluid conduit such that the second tubular member lumen is in fluid communication with the first fluid conduit.

6. The apparatus of claim 5, wherein the proximal portion of the second tubular member is fixedly secured to the first fluid conduit.

7. The apparatus of claim 6, wherein a distal portion of the second tubular member terminates in an intermediate region of the first tubular member.

8. The apparatus of claim 1, wherein the second tubular member and the first tubular member are sized to define a gap between an outer diameter of the second tubular member and an inner diameter of the first tubular member, wherein the gap is in fluid communication with the second fluid conduit.

9. The apparatus of claim 8, wherein a distal portion of the second tubular member terminates in an intermediate region of the first tubular member such that the first tubular member lumen at the intermediate region is configured to receive both of:
  (i) fluid from the first fluid conduit via the second tubular member lumen, and
  (ii) fluid from the second fluid conduit via the gap.

10. The apparatus of claim 1, wherein the second tubular member has a distal end positioned in an intermediate region of the first tubular member, wherein the inner cannula has a proximal end positioned in the intermediate region of the first tubular member, wherein the proximal end of the inner cannula is spaced distally from the distal end of the second tubular member.

11. The apparatus of claim 1, wherein the first tubular member, the second tubular member, and the inner cannula are all coaxially aligned with each other.

12. The apparatus of claim 1, wherein the inner cannula is flexible.

13. The apparatus of claim 1, wherein the inner cannula comprises polyether block amide or polyimide.

14. An apparatus, comprising:
  (a) a first fluid conduit extending along a first axis;
  (b) a second fluid conduit extending along a second axis, wherein the second axis is offset from the first axis;
  (c) a first elongate member extending along the first axis, wherein the first elongate member has a distal end, a proximal end, and an outer surface, wherein the first elongate member defines a first lumen, wherein the proximal end of the first elongate member is positioned in the first fluid conduit such that the first lumen is in fluid communication with the first fluid conduit;
  (d) a second elongate member extending along the first axis, wherein the second elongate member defines second lumen bounded by an inner surface, wherein the distal end of the first elongate member is positioned within the second lumen, wherein the outer surface of the first elongate member and the inner surface of the second elongate member together define a gap in fluid communication with the second fluid conduit;
  (e) a third elongate member extending along the first axis, wherein the third elongate member has a proximal end fixed within the second elongate member, wherein the third elongate member defines a third lumen, wherein the proximal end of the third elongate member is positioned in the second lumen at a location distal to the distal end of the second elongate member, wherein the third lumen is in fluid communication with the first and second fluid conduits via the first lumen and via the gap, respectively;
  (f) a first body; and
  (g) a connecting body slidably housed within the first body, wherein the first elongate member and the second elongate member are attached to the connecting body such that the connecting body is configured to actuate the first elongate member, the second elongate member, and the third elongate member relative to the first body.

15. An apparatus, comprising:
  (a) a first fluid conduit;
  (b) a second fluid conduit;
  (c) a connector member, wherein the connector member comprises:
    (i) a first passageway, wherein a portion of the first fluid conduit is positioned in the first passageway, and
    (ii) a second passageway, wherein a portion of the second conduit is positioned in the second passageway;
  (d) a first tubular member, wherein the first tubular member defines a first tubular member lumen;
  (e) a second tubular member, wherein at least a portion of the second tubular member is positioned within the first tubular member lumen, wherein the second tubular member defines a second tubular member lumen;
  (f) an inner cannula, wherein a proximal portion of the inner cannula is fixedly secured within the first tubular member lumen, wherein the inner cannula defines an inner cannula lumen, wherein the inner cannula lumen is in fluid communication with the first and second fluid conduits via the first tubular member lumen and the second tubular member lumen; and
  (g) a body, where the first and second fluid conduits extend proximally from the body, wherein the inner cannula extends distally relative to the body, wherein the inner cannula is operable to translate relative to the body, wherein the first tubular member and the second tubular member are fixedly secured relative to the inner cannula such that the first tubular member and the second tubular member are operable to translate with the inner cannula relative to the body.

* * * * *